(12) United States Patent
Crooke et al.

(10) Patent No.: US 9,139,831 B2
(45) Date of Patent: Sep. 22, 2015

(54) MODULATION OF ANGIOPOIETIN-LIKE 3 EXPRESSION

(71) Applicant: Isis Pharmaceuticals, Inc., Carlsbad, CA (US)

(72) Inventors: Rosanne M. Crooke, Carlsbad, CA (US); Mark J. Graham, San Clemente, CA (US); Richard Lee, Oceanside, CA (US); Kenneth W. Dobie, Del Mar, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 14/149,715

(22) Filed: Jan. 7, 2014

(65) Prior Publication Data

US 2014/0193825 A1 Jul. 10, 2014

Related U.S. Application Data

(62) Division of application No. 13/520,997, filed as application No. PCT/US2011/020606 on Jan. 7, 2011, now Pat. No. 8,653,047.

(60) Provisional application No. 61/293,604, filed on Jan. 8, 2010.

(51) Int. Cl.
*C12N 15/113* (2010.01)
*G01N 33/50* (2006.01)

(52) U.S. Cl.
CPC .......... *C12N 15/113* (2013.01); *C12N 15/1136* (2013.01); *G01N 33/5023* (2013.01); *C12N 2310/11* (2013.01); *C12N 2310/14* (2013.01); *C12N 2310/315* (2013.01); *C12N 2310/321* (2013.01); *C12N 2310/3341* (2013.01); *C12N 2310/341* (2013.01)

(58) Field of Classification Search
USPC .......................................... 536/24.5; 514/44
See application file for complete search history.

(56) References Cited

U.S. PATENT DOCUMENTS

| | | | |
|---|---|---|---|
| 5,801,154 | A | 9/1998 | Baracchini et al. |
| 6,582,908 | B2 | 6/2003 | Fodor et al. |
| 7,267,819 | B2 | 9/2007 | Ferrara et al. |
| 2001/0053519 | A1 | 12/2001 | Fodor et al. |
| 2003/0017488 | A1* | 1/2003 | Koishi et al. ............. 435/6 |
| 2003/0228597 | A1 | 12/2003 | Cowsert et al. |
| 2005/0255487 | A1 | 11/2005 | Khvorova et al. |
| 2007/0031844 | A1 | 2/2007 | Khvorova et al. |
| 2007/0054856 | A1 | 3/2007 | Gerber et al. |
| 2008/0113351 | A1 | 5/2008 | Naito et al. |
| 2008/0177045 | A1 | 7/2008 | Lee et al. |
| 2008/0255030 | A1 | 10/2008 | Yu et al. |
| 2009/0098117 | A1 | 4/2009 | Ferrara et al. |
| 2009/0318536 | A1 | 12/2009 | Freier et al. |
| 2015/0057329 | A1 | 2/2015 | Bhanot et al. |

FOREIGN PATENT DOCUMENTS

| | | |
|---|---|---|
| CA | 2450022 | 12/2002 |
| WO | WO 01/05825 | 1/2001 |
| WO | WO 03/004602 | 1/2003 |
| WO | WO 03/044172 | 5/2003 |
| WO | WO 2008/073300 | 6/2008 |

OTHER PUBLICATIONS

Branch et al., "A good antisense molecule is hard to find," TIBS (1998) 23:45-50.
Browning et al., "Molecular mediators of hepatic steatosis and liver injury" J. Clin. Invest. (2004) 114:147-152.
Camenisch et al., "ANGPTL3 stimulates endothelial cell adhesion and migration via integrin alpha vbeta 3 and induces blood vessel formation in vivo." J. Biol. Chem. (2002) 277(19):17281-17290.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Conklin et al., "Identification of a mammalian angiopoietin-related protein expressed specifically in liver." Genomics (1999) 62(3):477-482.
Crooke et al., "Basic Principles of Antisense Therapeutics" Antisense Research and Application (1998) Chapter 1:1-50.
EMBL Accession No. BG400407, *Homo sapiens* cDNA clone, Mar. 17, 2001, retrieved from the Internet, Apr. 3, 2013 <http://www.ebi.ac.uk/Tools/dbfetch/emblfetch?id=BG400407&Submit=Go>.
Gautschi et al., "Activity of a Novel bcl-2/bcl-xL-Bispecific Antisense Oligonucleotide Against Tumors of Diverse Histologic Origins" J. Natl. Cancer Inst. (2001) 93:463-471.
GenBank Accession No. NM_014495.1. *Homo sapiens* angiopoietin-like 3 (ANGPTL3) mRNA, retrieved from the Internet on Apr. 18, 2013, downloaded from http://www.ncbi.nlm.nih.gov/nuccore/NM_014495.1.
Ishibashi et al., "Hypercholesterolemia in low density lipoprotein receptor knockout mice and its reversal by adenovirus-mediated gene delivery." J. Clin. Invest. (1993) 92(2):883-893.
Inaba et al., "Angiopoietin-like protein 3 mediates hypertriglyceridemia induced by the liver X receptor." J. Biol. Chem. (2003) 278(24):21344-21351.
Inukai et al., "ANGPTL3 is increased in both insulin-deficient and -resistant diabetic states." Biochem. Biophys. Res. Commun. (2004) 317(4):1075-1079.
Kaplan et al., "Regulation of the angiopoietin-like protein 3 gene by LXR " J. Lipid. Res. (2003) 44(1):136-143.
Koishi et al., "Angptl3 regulates lipid metabolism in mice." Nat. Genet. (2002) 30(2):151-157.

(Continued)

*Primary Examiner* — Terra C Gibbs
(74) *Attorney, Agent, or Firm* — Isis Pharmaceuticals, Inc.

(57) ABSTRACT

Provided herein are methods, compounds, and compositions for reducing expression of an ANGPTL3 mRNA and protein in an animal. Also provided herein are methods, compounds, and compositions for reducing plasma lipids, plasma glucose and atherosclerotic plaques in an animal. Such methods, compounds, and compositions are useful to treat, prevent, delay, or ameliorate any one or more of cardiovascular disease or metabolic disease, or a symptom thereof.

29 Claims, No Drawings

(56) References Cited

OTHER PUBLICATIONS

Linton et al., "Transgenic mice expressing high plasma concentrations of human apolipoprotein B100 and lipoprotein(a)." J. Clin. Invest. (1993) 92: 3029-3037.

Maher et al., "Comparative hybrid arrest by tandem antisense oligodeoxyribonucleotides or oligodeoxyriboncleoside methylphosphonates in a cell-free system" Nuc. Acid. Res. (1988) 16:3341-3358.

New England Biolabs 1998/1999 Catalog (cover page and pp. 121 and 284).

Reynolds et al., "Rational siRNA design for RNA interference" Nature Biotechnology (2004) 22(3):326-330.

Sanan et al., "Low density lipoprotein receptor-negative mice expressing human apolipoprotein B-100 develop complex atherosclerotic lesions on a chow diet: No accentuation by apolipoprotein(a)" PNAS (1998) 95:4544-4549.

Sanghvi et al., "Heterocyclic Base Modifications in Nucleic Acids and Their Applications in Antisense Oligonucleotides" Antisense Research and Applications (1993) pp. 273-288.

Shimamura et al., Biochem. Biophys. Res. Commun. (2003) 301:604-609.

Shimamura et al., "Leptin and insulin down-regulate angiopoietin-like protein 3, a plasma triglyceride-increasing factor" Biochem. Biophys. Res. Commun. (2004) 322:1080-1085.

Shimizugawa et al., "ANGPTL3 decreases very low density lipoprotein triglyceride clearance by inhibition of lipoprotein lipase" J. Biol. Chem. (2002) 277:33742-33748.

Sindelka et al., "Association of Obesity, Diabetes, Serum Lipids and Blood Pressure Regulates Insulin Action" Physiol. Res. (2002) 51:85-91.

Valdivielso et al., "Association of moderate and severe hypertriglyceridemia with obesity, diabetes mellitus and vascular disease in the Spanish working population: Results of the ICARIA study" Atherosclerosis (2009) 207(2):573-578.

Willer et al., "Newly identified loci that influence lipid concentrations and risk of coronary artery disease" Nature Genetics (2008) 40(2):161-169.

Woolf et al., "Specificity of antisense oligonucleotides in vivo" PNAS (1992) 89:7305-7309.

Zhang et al., "Spontaneous atherosclerosis in aged lipoprotein lipase-deficient mice with severe hypertriglyceridemia on a normal chow diet." Circ. Res. (2008) 102(2):250-256.

International Search Report for application PCT/US11/20606 dated Jun. 27, 2011.

Lee et al., "Identification of a New Functional Domain in Angiopoietin-like 3 (ANGPTL3) and Angiopoietin-like 4 (ANGPTL4) Involved in Binding and Inhibition of Lipoprotein Lipase (LPL)" Journal of Biological Chemistry (2009) 284(20): 13735-13745.

Lichtenstein et al., "Modulation of plasma TG lipolysis by Angiopoietin-like proteins and GPIHBP1" Biochimica and Biophysica Acta (2010) 1804(4): 415-420.

Sonnenburg et al., "GPIHBP1 stabilizes lipoprotein lipase and prevents its inhibition by angiopoietin-like 3 and angiopoietin-like 4" The Journal of Lipid Research (2009) 50(12): 2421-2429.

European Search Report for application EP 11732249.5 dated Aug. 7, 2014.

Koster et al., "Transgenic angiopoietin-like (angptl)4 overexpression and targeted disruption of angptl4 and angptl3: regulation of triglyceride metabolism" Endocrinology (2005) 146(11): 4943-4950.

Naoumova et al., A new drug target for treatment of dyslipidaemia associated with type 2 diabetes and the metabolic syndrome? Lancet (2002) 359(9325):2215-2216.

Shimamura et al., "Angiopoietin-like protein3 regulates plasma HDL cholesterol through suppression of endothelial lipase" Arterioscler Thromb Vasc Biol. (2007) 27(2):366-372.

Gao et al., "Angiopoietin-like protein 3 regulates the motility and permeability of podocytes by altering nephrin expression in vitro" Biochemical and Biophysical Research Communications (2010) 399: 31-36.

Gao et al., "Angiopoietin-like protein 3 regulates the motility and permeability of podocytes by altering nephrin expression in vitro" Biochemical and Biophysical Research Communications (2010) 399:31-36.

\* cited by examiner

SEQUENCE LISTING

<160> NUMBER OF SEQ ID NOS: 193

<210> SEQ ID NO 1
<211> LENGTH: 833
<212> TYPE: DNA
<213> ORGANISM: Homo sapiens

<400> SEQUENCE: 1

```
attaatttca aaactaaaaa tcgtcagcac agagtatgtg taaaaatctg taatacaaat      60
ttttaaactg atgcttcatt ttgctacaaa ataatttgga gtaaatgttt gatatgattt     120
atttatgaaa cctaatgaag cagaattaaa tactgtatta aaataagttc gctgtcttta     180
aacaaatgga gatgactact aagtcacatt gactttaaca tgaggtatca ctatacctta     240
tttgttaaaa tatatactgt atacatttta tatattttaa cacttaatac tatgaaaaca     300 ataattgta aaggaatctt gtcagattac agtaagaatg aacatatttg tggcatcgag      360
ttaaagttta tatttcccct aaatatgctg tgattctaat acattcgtgt aggttttcaa     420
gtagaaataa acctcgtaac aagttactga acgtttaaac agcctgacaa gcatgtatat     480
atgtttaaaa ttcaataaac aaagacccag tccctaaatt atagaaattt aaattattct     540
tgcatgttta tcgacatcac aacagatccc taaatcccta atccctaaa gattagatac      600 aaattttta ccacagtatc acttgtcaga atttattttt aacatatgat tttttaaaac      660
tgccagtaag aaattttaaa tttaacccat tgttaagga tatagtgccc aagttaattg      720
gtgacctacc tttgtcaata cttagcataa tgtatttcaa aattatccaa tatacctgtc     780
atattaatct attatgtcca cttttttaag atatgtatga cctatgtgaa tct            833
```

<210> SEQ ID NO 2
<211> LENGTH: 795
<212> TYPE: DNA
<213> ORGANISM: Homo sapiens

<400> SEQUENCE: 2

```
ggtctaataa tctggtatta aatccttaag agaaagcttg agaaatagat ttttttatc       60 ttaaagtcac tgtctattta agattaaaca tacaatcaca taaccttaaa gaataccgtt     120
tacatttctc aatcaaaatt cttataatac tatttgtttt aaattttgtg atgtgggaat     180
caattttaga tggtcacaat ctagattata atcaataggt gaacttatta ataactttt      240 ctaaataaaa aatttagaga cttttatttt aaaaggcatc atatgagcta atatcacaac     300
tttcccagtt taaaaaacta gtactcttgt taaaactcta aacttgacta aatacagagg     360
actggtaatt gtacagttct taaatgttgt agtattaatt tcaaaactaa aaatcgtcag     420
cacagagtat gtgtaaaaat ctgtaataca aattttttaaa ctgatgcttc attttgctac    480
aaaataattt ggagtaaatg tttgatatga tttatttatg aaacctaatg aagcagaatt     540
aaatactgta ttaaaataag ttcgctgtct ttaaacaaat ggagatgact actaagtcac     600
attgacttta acatgaggta tcactatacc ttattgttaa acatatatac tgtatacatt     660
ttatatattt taacacttaa tactatgaaa acaataatt gtaaggaatc ttgtcagatt      720
acagtaagaa tgaacatatt tgtggcatcg agttaaagtt tatatttccc ctaaatatg      780 cttgtgattc taata                                                      795
```

<210> SEQ ID NO 3
<211> LENGTH: 743
<212> TYPE: DNA
<213> ORGANISM: Homo sapiens

<400> SEQUENCE: 3

```
atatatagag ttaagaagtc taggtctgct tccagaagaa acagttcca cgttgcttga      60
aattgaaaat caagataaaa atgttcacaa ttaagctcct tcttttatt gttcctctag     120
ttatttcctc cagaattgat caagacaatt catcatttga ttctctatct ccagagccaa    180
aatcaagatt tgctatgtta gacgatgtaa aaattttagc caatggcctc cttcagttgg    240
gacatggtct taaagacttt gtccataaga cgaaggggcc aaatttattg gacatatttc    300
aaaaactcaa catatttgat cagtcttttt atgatctatc gctgcaaacc agtgaaatca    360
aagaagaaga aaaggaactg agaagaacta catataaact acaagtcaaa aatgaagagg    420
taaagaatat gtcacttgaa ctcaactcaa aacttgaaag cctcctagaa gaaaaaattc    480
tacttcaaca aaaagtgaaa tatttagaag agcaactaac taacttaatt caacaatcaa    540
cctgaaactc cagaacaccc agaagtaact tcacttaaaa ctttgtagaa aaacaagata    600
atagcatcaa agaccttctc cagaccgtgg aagaccaata taaacaatta aaccaacagc    660
aaaaaacaaa caatcacaca cacacacaca ccaacacaac tcttttggc gccccattgc    720
cctccaaaaa aattttaaa cac                                             743
```

<210> SEQ ID NO 4
<211> LENGTH: 1496
<212> TYPE: DNA
<213> ORGANISM: Homo sapiens
<220> FEATURE:
<221> NAME/KEY: CDS
<222> LOCATION: (25)..(1407)

<400> SEQUENCE: 4

```
ggcacgagga aaatcaagat aaaa atg ttc aca att aag ctc ctt ctt ttt       51
                              Met Phe Thr Ile Lys Leu Leu Leu Phe
                               1               5 att gtt cct cta gtt att tcc tcc aga att gat caa gac aat tca tca     99
Ile Val Pro Leu Val Ile Ser Ser Arg Ile Asp Gln Asp Asn Ser Ser
 10              15                  20                  25 ttt gat tct cta tct cca gag cca aaa tca aga ttt gct atg tta gac    147
Phe Asp Ser Leu Ser Pro Glu Pro Lys Ser Arg Phe Ala Met Leu Asp
                 30                  35                  40 gat gta aaa att tta gcc aat ggc ctc ctt cag ttg gga cat ggt ctt    195
Asp Val Lys Ile Leu Ala Asn Gly Leu Leu Gln Leu Gly His Gly Leu
             45                  50                  55 aaa gac ttt gtc cat aag acg aag ggc caa att aat gac ata ttt caa    243
Lys Asp Phe Val His Lys Thr Lys Gly Gln Ile Asn Asp Ile Phe Gln
         60                  65                  70 aaa ctc aac ata ttt gat cag tct ttt tat gat cta tcg ctg caa acc    291
Lys Leu Asn Ile Phe Asp Gln Ser Phe Tyr Asp Leu Ser Leu Gln Thr
     75                  80                  85 agt gaa atc aaa gaa gaa gaa aag gaa ctg aga aga act aca tat aaa    339
Ser Glu Ile Lys Glu Glu Glu Lys Glu Leu Arg Arg Thr Thr Tyr Lys
 90                  95                 100                 105 cta caa gtc aaa aat gaa gag gta aag aat atg tca ctt gaa ctc aac    387
Leu Gln Val Lys Asn Glu Glu Val Lys Asn Met Ser Leu Glu Leu Asn
                110                 115                 120 tca aaa ctt gaa agc ctc cta gaa gaa aaa att cta ctt caa caa aaa    435
Ser Lys Leu Glu Ser Leu Leu Glu Glu Lys Ile Leu Leu Gln Gln Lys
            125                 130                 135 gtg aaa tat tta gaa gag caa cta act aac tta att caa aat caa cct    483
Val Lys Tyr Leu Glu Glu Gln Leu Thr Asn Leu Ile Gln Asn Gln Pro
        140                 145                 150
```

-continued

```
gaa act cca gaa cac cca gaa gta act tca ctt aaa act ttt gta gaa    531
Glu Thr Pro Glu His Pro Glu Val Thr Ser Leu Lys Thr Phe Val Glu
        155                 160                 165 aaa caa gat aat agc atc aaa gac ctt ctc cag acc gtg gaa gac caa    579
Lys Gln Asp Asn Ser Ile Lys Asp Leu Leu Gln Thr Val Glu Asp Gln
170                 175                 180                 185 tat aaa caa tta aac caa cag cat agt caa ata aaa gaa ata gaa aat    627
Tyr Lys Gln Leu Asn Gln Gln His Ser Gln Ile Lys Glu Ile Glu Asn
                190                 195                 200 cag ctc aga agg act agt att caa gaa ccc aca gaa att tct cta tct    675
Gln Leu Arg Arg Thr Ser Ile Gln Glu Pro Thr Glu Ile Ser Leu Ser
            205                 210                 215 tcc aag cca aga gca cca aga act act ccc ttt ctt cag ttg aat gaa    723
Ser Lys Pro Arg Ala Pro Arg Thr Thr Pro Phe Leu Gln Leu Asn Glu
        220                 225                 230 ata aga aat gta aaa cat gat ggc att cct gct gaa tgt acc acc att    771
Ile Arg Asn Val Lys His Asp Gly Ile Pro Ala Glu Cys Thr Thr Ile
235                 240                 245 tat aac aga ggt gaa cat aca agt ggc atg tat gcc atc aga ccc agc    819
Tyr Asn Arg Gly Glu His Thr Ser Gly Met Tyr Ala Ile Arg Pro Ser
250                 255                 260                 265 aac tct caa gtt ttt cat gtc tac tgt gat gtt ata tca ggt agt cca    867
Asn Ser Gln Val Phe His Val Tyr Cys Asp Val Ile Ser Gly Ser Pro
                270                 275                 280 tgg aca tta att caa cat cga ata gat gga tca caa aac ttc aat gaa    915
Trp Thr Leu Ile Gln His Arg Ile Asp Gly Ser Gln Asn Phe Asn Glu
            285                 290                 295 acg tgg gag aac tac aaa tat ggt ttt ggg agg ctt gat gga gaa ttt    963
Thr Trp Glu Asn Tyr Lys Tyr Gly Phe Gly Arg Leu Asp Gly Glu Phe
        300                 305                 310 tgg ttg ggc cta gag aag ata tac tcc ata gtg aag caa tct aat tat   1011
Trp Leu Gly Leu Glu Lys Ile Tyr Ser Ile Val Lys Gln Ser Asn Tyr
        315                 320                 325 gtt tta cga att gag ttg gaa gac tgg aaa gac aac aaa cat tat att   1059
Val Leu Arg Ile Glu Leu Glu Asp Trp Lys Asp Asn Lys His Tyr Ile
330                 335                 340                 345 gaa tat tct ttt tac ttg gga aat cac gaa acc aac tat acg cta cat   1107
Glu Tyr Ser Phe Tyr Leu Gly Asn His Glu Thr Asn Tyr Thr Leu His
                350                 355                 360 cta gtt gcg att act ggc aat gtc ccc aat gca atc ccg gaa aac aaa   1155
Leu Val Ala Ile Thr Gly Asn Val Pro Asn Ala Ile Pro Glu Asn Lys
            365                 370                 375 gat ttg gtg ttt tct act tgg gat cac aaa gca aaa gga cac ttc aac   1203
Asp Leu Val Phe Ser Thr Trp Asp His Lys Ala Lys Gly His Phe Asn
        380                 385                 390 tgt cca gag ggt tat tca gga ggc tgg tgg cat gat gag tgt gga       1251
Cys Pro Glu Gly Tyr Ser Gly Gly Trp Trp His Asp Glu Cys Gly
395                 400                 405 gaa aac aac cta aat ggt aaa tat aac aaa cca aga gca aaa tct aag   1299
Glu Asn Asn Leu Asn Gly Lys Tyr Asn Lys Pro Arg Ala Lys Ser Lys
410                 415                 420                 425 cca gag agg aga aga gga tta tct tgg aag tct caa aat gga agg tta   1347
Pro Glu Arg Arg Arg Gly Leu Ser Trp Lys Ser Gln Asn Gly Arg Leu
                430                 435                 440 tac tct ata aaa tca acc aaa atg ttg atc cat cca aca gat tca gaa   1395
Tyr Ser Ile Lys Ser Thr Lys Met Leu Ile His Pro Thr Asp Ser Glu
            445                 450                 455 agc ttt gaa tga actgaggcaa atttaaaagg caataattta aacattaacc       1447
Ser Phe Glu
```

```
                                    460
tcattccaag ttaatgtggt ctaataatct ggtattaaat ccttaagag          1496

<210> SEQ ID NO 5
<211> LENGTH: 9381
<212> TYPE: DNA
<213> ORGANISM: Homo sapiens

<400> SEQUENCE: 5
ttccaaaaga actaaagtac agtttgagaa atgcatactt aattcattac ttttttcccc     60
tcaactttaa taataaattt acccaacaaa aaagtttatt tttgacttgt aaatctctta    120
aaatcataaa aaagtaaaat tagcttttaa aaacaggtag tcaccatagc attgaatgtg    180
tagtttataa tacagcaaag ttaaatacaa tttcaaatta cctattaagt tagttgctca    240
tttctttgat ttcatttagc attgatctaa ctcaatgtgg aagaaggtta cattcgtgca    300
agttaacacg gcttaatgat taactatgtt cacctaccaa ccttaccttt tctgggcaaa    360
tattggtata tatagagtta agaagtctag gtctgcttcc agaagaaaac agttccacgt    420
tgcttgaaat tgaaaatcaa gataaaaatg ttcacaatta agctccttct ttttattgtt    480
cctctagtta tttcctccag aattgatcaa gacaattcat catttgattc tctatctcca    540
gagccaaaat caagatttgc tatgttagac gatgtaaaaa ttttagccaa tggcctcctt    600
cagttgggac atggtcttaa agactttgtc cataagacga agggccaaat taatgacata    660
tttcaaaaac tcaacatatt tgatcagtct ttttatgatc tatcgctgca aaccagtgaa    720
atcaaagaag aagaaaagga actgagaaga actacaatata aactacaagt caaaaatgaa    780
gaggtaaaga atatgtcact tgaactcaac tcaaaacttg aaagcctcct agaagaaaaa    840
attctacttc aacaaaaagt gaaatattta gaagagcaac taactaactt aattcaaaat    900
caacctgaaa ctccagaaca cccagaagta acttcactta agtaagtag aaaataaaga    960 gggttcatgt ttatgttttc aatgtggatc ttttaaaaaa atatttcta aggcatgcca   1020 tttgaaatac tttgttgcat tgttgaaata cttttttttc caagaaaaat aatctccaga   1080
aaataaaatt tcctattata atttcaagtt agttttttgt ttccctaatg ttatatatga   1140
aaacactgaa aatttgcatt ttatatgaaa attacaaatc ggttaaatta tacaatctag   1200
aacactatgt cattcactta ttgtaaatta ctgaaggtaa gtaaaaagtt aaaaaaaatt   1260
taaaactatt ctccagtgtt taaaacagat taaataatac agtaaatgga aaagatttat   1320
tcatatgaaa atatgctggg cttttttcttt taattgaagt tcagaaaatc aaattttaga   1380
gatagtacaa tttaaataaa atgttaagga caaaaatatg tgctatttga agaagcata    1440 caaggggaag gaattgccaa tattcatttt tcaaatccat tattagttta aaaatttaga   1500
ttatgatagt gttacaggaa attaatagaa agaaagagg aaagcaactt ataaccaacc    1560
tactctctat atccagactt ttgtagaaaa acaagataat agcatcaaag accttctcca   1620
gaccgtggaa gaccaatata aacaattaaa ccaacagcat agtcaaataa agaaatagaa   1680
aaatcaggta agtcagtatt ttaatggtat gtcccatctt tcacacaggt ctgtaaaaac   1740
actgaatcct aaaattattt acaagcttta actggatcat gagtaaaatt atcacatcag   1800
cataactgtt aaaattgcag gctctgaagc taataaacta cctgcattta aaccatggct   1860
ctaaaacttt gtgtgaccct gaataaaatta cttcacccct ttatctctca gtttcctcac   1920
atatactaca aagataataa cagaacttat aggattattg taagaaaaaa aattaattca   1980
tagcagccaa tgtcatctta ctaaaattca aattagatca tgtttctctt tgctcaaaac   2040
```

```
cacacaatag ctttccattt cactcatatt ggctctttag accaagatta cccaacccett   2100
cgtcatctca ctgacttcac ctcctctact ctagttattc tgaccgcttt accagtattc   2160
aaacacatca aacatactgc cacctcaaag cctttgccct tgttgtttcc tctaactgga   2220
acgctcttct gccctggtat ctacgtggcc cactctctga tttcccttag ggtcgttatc   2280
aaacaaaaaa ttcccaatga agacttacaa ggtcacttaa ccaaaaatca caaccgcctg   2340
gtcccatccc tgaaaacttc tacttcctta gctacttttc tcctgcacac tcacctttat   2400
ttaacataac ataaattta gttatttatc tcttctattc ctgcactaaa atgtaagctc    2460
tgtgaataca gggattttt ccattatctt catattttcc attatttgta tatactccag   2520
aatatagaat actgtatggc acacagtagg catttctgtt gaattaataa atgtaatgtc   2580
atattcacac agaagcgtgt gctatgatta ttattacttg gattactaga aatagtgtgc   2640
ctcataatta aaggtcaaca ttcaacaatg taattaatct acaatgtaaa catctggtga   2700
agtgacagag ggaagcactt gtttagaaaa aagctatgtc agaatccatg tattctaata   2760
tgcagtacaa tagtttaaaa atattaataa tactctcaaa cagctattca agaggattca   2820
aaaaacataa tataaactca gagaaactgg taaacaaaat cattttcaag agatataaaa   2880
caaatattat taccaatttc cactaaacaa acataatgtt agtagtgctg ctaaaaggtt   2940
ttttatcaac tactttggt ttccatactt tccttcttat gatgttatta ttctaaattc    3000
ttttcaatta tatcttttac tatgattaaa tgaacctgct ccccaaagca aatgttact    3060
atagtaatat acattgtgtc taaaaataaa aatgtgtgaa gaaaccaaaa caatgaattt   3120
ctgagttgga agaagagtta gatcatttaa ctttctcata tttaaattaa aaaaacaaaa   3180
ctctaaaaat ttaagtaact ttaagatcac atagttactt agtagaaaag agtaatacccc  3240
agcaagcaaa ctttacaata gatccttta aataaggtcc taggaaatat cattcatgcc    3300
agcatcaaaa aactaacact aataatgcaa gatattatat attctgcttt tcttactgtc   3360
aatgagaaaa actatcattc aataaattgc aaacccaaca cacttaaata aaaataaaat   3420
gttactgcta aactaacgat aaactactga atatatagaa agtaagcaaa caaacttgcc   3480
aacctgccaa catctacaga tatgtttaca ggtcaaaaat tatcaaatta tcaagaaagc   3540
ctggttcaaa ttatgtatta tgtctttatc acaggtctga agatcagtaa gacctaaaac   3600
tgaaaattat taaacttaaa atctgaacag aatatcaaat atattttatt catataaata   3660
aaagaataca ttacaatatt ctaagcaaag cagtctctac ttttggcctt gctctgtttt   3720
ccgaccaatg tctgcttttt tgccttgctt tattttttta tcttattaaa taatgtccct   3780
gattaaaatat tttgagaaca ggtaatctgt acaatctgaa taacactgtt tatctaaata  3840
tcaaacaccg ttataacatt atgaactgaa agacaaactg tacttctgac atccttactc   3900
agatttcccc taattgtata ttcagtatca ttttaaaaaa cagatttata ttcttttatc   3960
agctcagaag gactagtatt caagaaccca cagaaatttc tctatcttcc aagccaagag   4020
caccaagaac tactcccttt cttcagttga atgaaataag aaatgtaaaa catgatggta   4080
agacactttg gtgggtttcc ttcttgaagc tattattatc aaattcccta ttcttaggac   4140
ttgttctaga ctaaaagata gttaagagat atccatcaaa tacaatgtat caacctaaac   4200
tggatgctgg ggttcttttt acaccctata aaagacatac ctaagacaat cagagaaata   4260
caaatatgga cttgattatt agataatata gaaggtttat taattttctt agatgtgatc   4320
atggtattgc agttttaaag gagaacaatc tcctgtttaa gagatacatg ctgaaatatt   4380
```

```
tacggagtta aaggtcactg gactccagac tggtgataga acaagactct gtctctaaaa    4440
aataattaat tttttaaaag aaaatagttt ggtaagatga ttcttacatt cttaaataac    4500
acgccatcta agaaaaatgc tttaacataa acattactga aaaaatgcta catttgccac    4560
aacttcataa aatgtcaagt gaaatctcaa gctccaaaga tattattcct attactaaat    4620
ctgatgtaat aacattttat tgattctagg cattcctgct gaatgtacca ccatttataa    4680
cagaggtgaa catacaagtg gcatgtatgc catcagaccc agcaactctc aagtttttca    4740
tgtctactgt gatgttatat caggtaaaac ctgtctaagg agaatagaca gtagttagtt    4800
caacttactc attacgtatt aggaagatta acctggttat cattgtttta tacatatata    4860
tatgaaatat atatgagtat tcgtataaat ataaactttt accttgtttt atgtatttac    4920
tcaatattct ccttttcctc taaaataatc tgaagtgact attatcaata agttactat     4980 gccaaaattc attaattgcc tttcacttaa cttttgggac cataataaat aataaaatgt    5040
attgccataa cattaataaa ctaccttaca aaaccaccaa ttaaaatcaa acaaacaaaa    5100
aagtgttatt tacatctgtc aacataaatc tactaaaaat acatgatttc attcattata    5160
ttcaggtagt ccatggacat taattcaaca tcgaatagat ggatcacaaa acttcaatga    5220
aacgtgggag aactacaaat atggttttgg gaggcttgat ggtaagggga ctacattcaa    5280
tcattcattc acttgctaat ctacaaatat ttactgagaa cctcttatgg accaggtatt    5340
aggaaaagta gtaacgaacg agaagcagtc tcagccttca tataatttat tatcaaacaa    5400
ttacacattt gttagtaaat tacacttatt acaactgtta ttatttgaat tatatttatc    5460
acaattacat gtctgttctt aaatatactt atcacaattt aattccacgg cttacaatga    5520
tcataactat aattattaaa gacaattttg attaaatgtt atgtcataag tagtaactgt    5580
tacaaataag ctgtgaaaag aaccactcct agcattagtc actctattct ctcattaacg    5640
ttttacatat caattaattg gaagttaaaa ggaccaggaa actcagacat acagtataca    5700
ttttaaaatt tcaattattt aaatataata tatagaatgt atggcttata atgaattagt    5760
taactcaatg caaattattc tattttgatt acaaatagta aaataagcaa gataaaataa    5820
cagatgttta aaatccaaaa agcacataca aaaatccatg aatgatgtct aagtactcac    5880
ttataaagta gaagacattc attattatat caaattttta aatgctcagt actatttgac    5940
catttaaaaa ttttgtattc aaactaccag tgaaagccct acctagaagg tatactcagt    6000
gataagtttt gtagctccaa atcttctaat agtgagtgta accccaaaat aaaaggctga    6060
caggtaagtc gagaatactc acttaattct ggtaagaaag caacccattt gtacttgtat    6120
ttaccagcaa tccttaaaat gaagcttcct actaactcaa tagcaataag acaatagtga    6180
atgtttaatg aaaacagtat tttataaata cttaataaaa aaggattgtg atgaagaaca    6240
atctatttat atttgttatt tgttttttaat tccaataaaa ataattttta aaattacaga    6300
aaaaagttat taagaaccat gcttttaaat ttaaaatgat ttttttaaatt tattcctgtc    6360 tttttctaca aagaaagcat acattaagca aataccaaag gccaggttta catttgaaga    6420
aagtgacatt attattactc aagtctctag gaatacttaa cacatctctt gactgtatat    6480
ggatgttaat aaatagctga cagtaaagtt tatccatata aagacttgca atattcctc     6540 taccaatgac gagactttaa aatatctata ataatgtaac acatttcact ggtgaaacat    6600
gtcttgtcat atgcattata gaaaggataa tcagactttc agttatatta atattttaa     6660 catttttgtg cacatagcta tcttcaataa aattgttta aaaggtatta ttttaagata     6720
cactaaaatg atcaagggat tcaagactaa acaactcaat tagttgcacc aataaaaaac    6780
```

```
acttaaaaaa actgtcagtg tccaacctgt acttaataac tcacagattt ttaaaacttt    6840
tcttttcagg agaattttgg ttgggcctag agaagatata ctccatagtg aagcaatcta    6900
attatgtttt acgaattgag ttggaagact ggaaagacaa caaacattat attgaatatt    6960 cttttttactt gggaaatcac gaaaccaact atacgctaca tctagttgcg attactggca    7020
atgtccccaa tgcaatcccg gaaaacaaag atttggtgtt ttctacttgg gatcacaaag    7080
caaaaggaca cttcaactgt ccagagggtt attcaggtat cttttttctga taccaatact    7140 ttattttcat atcttcaaag tatcttccca cattattagc tattatctgc aatgacaact    7200
tttaaaaatc cgaatcccaa ataagcgttt tctctctaga cgaaaacctc ttaactataa    7260
tgaaagtgtt cattctagtt caatcaggta ttttacctct aatcttcctc agattttcta    7320 tttttttggta gtgtatagat tatttataca gattatttaa aattgggact tatacagatt    7380
atttaaaact gggatacatg catctaaaac actgtaatat ttataagaaa ggaagataaa    7440
cttacgggga aatacagtaa cagtaactac atacgagtct gtacccatta aattgcatat    7500
ctatctcctt taggaggctg gtggtggcat gatgagtgtg gagaaaacaa cctaaatggt    7560
aaatataaca aaccaagagc aaaatctaag ccagagagga gaagaggatt atcttggaag    7620
tctcaaaatg gaaggttata ctctataaaa tcaaccaaaa tgttgatcca tccaacagat    7680
tcagaaagct ttgaatgaac tgaggcaaat ttaaaaggca ataatttaaa cattaacctc    7740
attccaagtt aatgtggtct aataatctgg tattaaatcc ttaagagaaa gcttgagaaa    7800 tagattttttt ttatcttaaa gtcactgtct atttaagatt aaacatacaa tcacataacc    7860
ttaaagaata ccgtttacat ttctcaatca aaattcttat aatactattt gttttaaatt    7920
ttgtgatgtg ggaatcaatt ttagatggtc acaatctaga ttataatcaa taggtgaact    7980
tattaaataa cttttctaaa taaaaaattt agagactttt atttttaaaag gcatcatatg    8040 agctaatatc acaactttcc cagtttaaaa aactagtact cttgttaaaa ctctaaactt    8100
gactaaatac agaggactgg taattgtaca gttcttaaat gttgtagtat taatttcaaa    8160
actaaaaatc gtcagcacag agtatgtgta aaaatctgta atacaaattt ttaaactgat    8220
gcttcatttt gctacaaaat aatttggagt aaatgtttga tatgatttat ttatgaaacc    8280
taatgaagca gaattaaata ctgtattaaa ataagttcgc tgtctttaaa caaatggaga    8340
tgactactaa gtcacattga cttaacatg aggtatcact ataccttatt tgttaaaata    8400
tatactgtat acattttata tattttaaca cttaatacta tgaaaacaaa taattgtaaa    8460
ggaatcttgt cagattacag taagaatgaa catatttgtg gcatcgagtt aaagtttata    8520
tttcccctaa atatgctgtg attctaatac attcgtgtag gttttcaagt agaaataaac    8580
ctcgtaacaa gttactgaac gtttaaacag cctgacaagc atgtatatat gtttaaaatt    8640
caataaacaa agacccagtc cctaaattat agaaatttaa attattcttg catgtttatc    8700
gacatcacaa cagatcccta aatccctaaa tccctaaaga ttagatacaa attttttacc    8760
acagtatcac ttgtcagaat ttatttttaa atatgatttt ttaaaactgc cagtaagaaa    8820
ttttaaatta aacccatttg ttaaaggata tagtgcccaa gttatatggt gacctacctt    8880
tgtcaatact tagcattatg tatttcaaat tatccaatat acatgtcata tatattttta    8940
tatgtcacat atataaaaga tatgtatgat ctatgtgaat cctaagtaaa tattttgttc    9000
cagaaaagta caaaataata aaggtaaaaa taatctataa ttttcaggac cacagactaa    9060
gctgtcgaaa ttaacgctga tttttttagg gccagaatac caaaatggct cctctcttcc    9120
```

```
cccaaaattg acaatttca aatgcaaaat aattcattat ttaatatatg agttgcttcc    9180
tctatttggt ttccttaaaa aaaaaaaaaa ctctcatagg acatgtttca ttttgttcct    9240
ttcaggagta gtaaattaga cgttttcccc atataaagct tttttctacc agaaagatac    9300
ttctggtaga agaagagaaa ggagctcttt atggttcaca cgactgtctc ctgtcctaac    9360
tactttgctt aaagtgctca a                                             9381

<210> SEQ ID NO 6
<211> LENGTH: 1449
<212> TYPE: DNA
<213> ORGANISM: Mus musculus
<220> FEATURE:
<221> NAME/KEY: CDS
<222> LOCATION: (19)..(1386)

<400> SEQUENCE: 6
aataattgag acaaaaaa atg cac aca att aaa tta ttc ctt ttt gtt gtt           51
                   Met His Thr Ile Lys Leu Phe Leu Phe Val Val
                    1               5                  10 cct tta gta att gca tcc aga gtg gat cca gac ctt tca tca ttt gat          99
Pro Leu Val Ile Ala Ser Arg Val Asp Pro Asp Leu Ser Ser Phe Asp
             15                  20                  25 tct gca cct tca gag cca aaa tca aga ttt gct atg ttg gat gat gtc         147
Ser Ala Pro Ser Glu Pro Lys Ser Arg Phe Ala Met Leu Asp Asp Val
         30                  35                  40 aaa att tta gcg aat ggc ctc ctg cag ctg ggt cat gga ctt aaa gat         195
Lys Ile Leu Ala Asn Gly Leu Leu Gln Leu Gly His Gly Leu Lys Asp
     45                  50                  55 ttt gtc cat aag act aag gga caa att aac gac ata ttt cag aag ctc         243
Phe Val His Lys Thr Lys Gly Gln Ile Asn Asp Ile Phe Gln Lys Leu
 60                  65                  70                  75 aac ata ttt gat cag tct ttt tat gac cta tca ctt cga acc aat gaa         291
Asn Ile Phe Asp Gln Ser Phe Tyr Asp Leu Ser Leu Arg Thr Asn Glu
                 80                  85                  90 atc aaa gaa gag gaa aag gag cta aga aga act aca tct aca cta caa         339
Ile Lys Glu Glu Glu Lys Glu Leu Arg Arg Thr Thr Ser Thr Leu Gln
             95                 100                 105 gtt aaa aac gag gag gtg aag aac atg tca gta gaa ctg aac tca aag         387
Val Lys Asn Glu Glu Val Lys Asn Met Ser Val Glu Leu Asn Ser Lys
        110                 115                 120 ctt gag agt ctg ctg gaa gag aag aca gcc ctt caa cac aag gtc agg         435
Leu Glu Ser Leu Leu Glu Glu Lys Thr Ala Leu Gln His Lys Val Arg
    125                 130                 135 gct ttg gag gag cag cta acc aac tta att cta agc cca gct ggg gct         483
Ala Leu Glu Glu Gln Leu Thr Asn Leu Ile Leu Ser Pro Ala Gly Ala
140                 145                 150                 155 cag gag cac cca gaa gta aca tca ctc aaa agt ttt gta gaa cag caa         531
Gln Glu His Pro Glu Val Thr Ser Leu Lys Ser Phe Val Glu Gln Gln
                160                 165                 170 gac aac agc ata aga gaa ctc ctc cag agt gtg gaa gaa cag tat aaa         579
Asp Asn Ser Ile Arg Glu Leu Leu Gln Ser Val Glu Glu Gln Tyr Lys
            175                 180                 185 caa tta agt caa cag cac atg cag ata aaa gaa ata gaa aag cag ctc         627
Gln Leu Ser Gln Gln His Met Gln Ile Lys Glu Ile Glu Lys Gln Leu
        190                 195                 200 aga aag act ggt att caa gaa ccc tca gaa aat tct ctt tct tct aaa         675
Arg Lys Thr Gly Ile Gln Glu Pro Ser Glu Asn Ser Leu Ser Ser Lys
    205                 210                 215 tca aga gca cca aga act act ccc cct ctt caa ctg aac gaa aca gaa         723
Ser Arg Ala Pro Arg Thr Thr Pro Pro Leu Gln Leu Asn Glu Thr Glu
```

|  |  |  |  |  |  |  |  |  |  |  |  |  |  |  |
|---|---|---|---|---|---|---|---|---|---|---|---|---|---|---|
| 220 |  |  |  |  | 225 |  |  |  |  | 230 |  |  |  | 235 |

```
aat aca gaa caa gat gac ctt cct gcc gac tgc tct gcc gtt tat aac       771
Asn Thr Glu Gln Asp Asp Leu Pro Ala Asp Cys Ser Ala Val Tyr Asn
                240                 245                 250 aga ggc gaa cat aca agt ggc gtg tac act att aaa cca aga aac tcc       819
Arg Gly Glu His Thr Ser Gly Val Tyr Thr Ile Lys Pro Arg Asn Ser
            255                 260                 265 caa ggg ttt aat gtc tac tgt gat acc caa tca ggc agt cca tgg aca       867
Gln Gly Phe Asn Val Tyr Cys Asp Thr Gln Ser Gly Ser Pro Trp Thr
        270                 275                 280 tta att caa cac cgg aaa gat ggc tca cag gac ttc aac gaa aca tgg       915
Leu Ile Gln His Arg Lys Asp Gly Ser Gln Asp Phe Asn Glu Thr Trp
    285                 290                 295 gaa aac tac gaa aag ggc ttt ggg agg ctc gat gga gaa ttt tgg ttg       963
Glu Asn Tyr Glu Lys Gly Phe Gly Arg Leu Asp Gly Glu Phe Trp Leu
300                 305                 310                 315 ggc cta gag aag atc tat gct ata gtc caa cag tct aac tac att tta      1011
Gly Leu Glu Lys Ile Tyr Ala Ile Val Gln Gln Ser Asn Tyr Ile Leu
                320                 325                 330 cga ctc gag cta caa gac tgg aaa gac agc aag cac tac gtt gaa tac      1059
Arg Leu Glu Leu Gln Asp Trp Lys Asp Ser Lys His Tyr Val Glu Tyr
            335                 340                 345 tcc ttt cac ctg ggc agt cac gaa acc aac tac acg cta cat gtg gct      1107
Ser Phe His Leu Gly Ser His Glu Thr Asn Tyr Thr Leu His Val Ala
        350                 355                 360 gag att gct ggc aat atc cct ggg gcc ctc cca gag cac aca gac ctg      1155
Glu Ile Ala Gly Asn Ile Pro Gly Ala Leu Pro Glu His Thr Asp Leu
    365                 370                 375 atg ttt tct aca tgg aat cac aga gca aag gga cag ctc tac tgt cca      1203
Met Phe Ser Thr Trp Asn His Arg Ala Lys Gly Gln Leu Tyr Cys Pro
380                 385                 390                 395 gaa agt tac tca ggt ggc tgg tgg tgg aat gac ata tgt gga gaa aac      1251
Glu Ser Tyr Ser Gly Gly Trp Trp Trp Asn Asp Ile Cys Gly Glu Asn
                400                 405                 410 aac cta aat gga aaa tac aac aaa ccc aga acc aaa tcc aga cca gag      1299
Asn Leu Asn Gly Lys Tyr Asn Lys Pro Arg Thr Lys Ser Arg Pro Glu
            415                 420                 425 aga aga aga ggg atc tac tgg aga cct cag agc aga aag ctc tat gct      1347
Arg Arg Arg Gly Ile Tyr Trp Arg Pro Gln Ser Arg Lys Leu Tyr Ala
        430                 435                 440 atc aaa tca tcc aaa atg atg ctc cag ccc acc acc taa gaagcttcaa      1396
Ile Lys Ser Ser Lys Met Met Leu Gln Pro Thr Thr
    445                 450                 455 ctgaactgag acaaaataaa agatcaataa attaaatatt aaagtcctcc cga           1449

<210> SEQ ID NO 7
<211> LENGTH: 510
<212> TYPE: DNA
<213> ORGANISM: Mus musculus
<220> FEATURE:
<221> NAME/KEY: CDS
<222> LOCATION: (67)..(510)

<400> SEQUENCE: 7
tgttggccta ctggacagga gggagaagtt ccaaattgct taaaattgaa taattgagac     60 aaaaaa tgc aca caa tta aat tat tcc ttt ttg ttg ttc ctt tag taa        108
       Cys Thr Gln Leu Asn Tyr Ser Phe Leu Leu Phe Leu
         1               5                  10 ttg cat cca gag tgg atc cag acc ttt cat cat ttg att ctg cac ctt       156
Leu His Pro Glu Trp Ile Gln Thr Phe His His Leu Ile Leu His Leu
```

```
                 15                  20                  25
cag agc caa aat caa gat ttg cta tgt tgg atg atg tca aaa ttt tag       204
Gln Ser Gln Asn Gln Asp Leu Leu Cys Trp Met Met Ser Lys Phe
            30                  35                  40 cga atg gcc tcc tgc agc tgg gtc atg gac tta aag att ttg tcc ata       252
Arg Met Ala Ser Cys Ser Trp Val Met Asp Leu Lys Ile Leu Ser Ile
    45                  50                  55 aga cta agg gac aaa tta acg aca tat ttc aga agc tca aca tat ttg       300
Arg Leu Arg Asp Lys Leu Thr Thr Tyr Phe Arg Ser Ser Thr Tyr Leu
60                  65                  70                  75 atc agt ctt ttt atg acc tat cac ttc gaa cca atg aaa tca aag aag       348
Ile Ser Leu Phe Met Thr Tyr His Phe Glu Pro Met Lys Ser Lys Lys
                80                  85                  90 agg aaa agg agc taa gaa gaa cta cat cta cac tac aag tta aaa acg       396
Arg Lys Arg Ser     Glu Glu Leu His Leu His Tyr Lys Leu Lys Thr
            95                 100                 105 agg agg tga aga aca ctt cag tag aac tga act caa agc ttg aga gtc       444
Arg Arg     Arg Thr Leu Gln     Asn     Thr Gln Ser Leu Arg Val
110 tgc tgg aag aga aga cag ccc ttc aac aca agg tca ggg ctt tgg agg       492
Cys Trp Lys Arg Arg Gln Pro Phe Asn Thr Arg Ser Gly Leu Trp Arg
120                 125                 130                 135 agc agc taa cca act taa                                               510
Ser Ser     Pro Thr <210> SEQ ID NO 8
<211> LENGTH: 271
<212> TYPE: DNA
<213> ORGANISM: Mus musculus

<400> SEQUENCE: 8
gagggatcta ctggagacct cagagcagaa agctctatgc tatcaaatca tccaaattga    60
tgctccaccc caccacctaa gaagcttcaa ctgaactgag acaaaataaa agatcaataa   120
attaaatatt aaattcctcc cgatcactgt agtaatctgg tattaaaatt ttaatggaaa   180
gcttgagaat tgaatttcaa ttaggtttaa actcattgtt aagatcagat atcaccgaat   240
caacgtaaac aaaatttatc tttttcaatc t                                   271

<210> SEQ ID NO 9

<400> SEQUENCE: 9

000

<210> SEQ ID NO 10

<400> SEQUENCE: 10

000

<210> SEQ ID NO 11
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 11
ctcttactgt gctgtggaca                                                 20

<210> SEQ ID NO 12
```

```
<211> LENGTH: 20
<212> TYPE: DNA
<213> ORGANISM: Artificial sequence
<220> FEATURE:
<223> OTHER INFORMATION: Primer

<400> SEQUENCE: 12
tgcagggcta catggaacaa                                                    20

<210> SEQ ID NO 13
<211> LENGTH: 20
<212> TYPE: DNA
<213> ORGANISM: Artificial sequence
<220> FEATURE:
<223> OTHER INFORMATION: Primer

<400> SEQUENCE: 13
cggactcctg cacgctactt                                                    20

<210> SEQ ID NO 14
<211> LENGTH: 23
<212> TYPE: DNA
<213> ORGANISM: Artificial sequence
<220> FEATURE:
<223> OTHER INFORMATION: Probe

<400> SEQUENCE: 14
ctccaagacg gtccaggatg cgc                                                23

<210> SEQ ID NO 15
<211> LENGTH: 21
<212> TYPE: DNA
<213> ORGANISM: Artificial sequence
<220> FEATURE:
<223> OTHER INFORMATION: Primer

<400> SEQUENCE: 15
caacggattt ggtcgtattg g                                                  21

<210> SEQ ID NO 16
<211> LENGTH: 26
<212> TYPE: DNA
<213> ORGANISM: Artificial sequence
<220> FEATURE:
<223> OTHER INFORMATION: Primer

<400> SEQUENCE: 16
ggcaacaata tccactttac cagagt                                             26

<210> SEQ ID NO 17
<211> LENGTH: 21
<212> TYPE: DNA
<213> ORGANISM: Artificial sequence
<220> FEATURE:
<223> OTHER INFORMATION: Probe

<400> SEQUENCE: 17
cgcctggtca ccagggctgc t                                                  21

<210> SEQ ID NO 18
<211> LENGTH: 19
<212> TYPE: DNA
<213> ORGANISM: Artificial sequence
<220> FEATURE:
<223> OTHER INFORMATION: Primer

<400> SEQUENCE: 18
```

```
gaaggtgaag gtcggagtc                                              19

<210> SEQ ID NO 19
<211> LENGTH: 20
<212> TYPE: DNA
<213> ORGANISM: Artificial sequence
<220> FEATURE:
<223> OTHER INFORMATION: Primer

<400> SEQUENCE: 19
gaagatggtg atgggatttc                                             20

<210> SEQ ID NO 20
<211> LENGTH: 20
<212> TYPE: DNA
<213> ORGANISM: Artificial sequence
<220> FEATURE:
<223> OTHER INFORMATION: Probe

<400> SEQUENCE: 20
caagcttccc gttctcagcc                                             20

<210> SEQ ID NO 21
<211> LENGTH: 20
<212> TYPE: DNA
<213> ORGANISM: Artificial sequence
<220> FEATURE:
<223> OTHER INFORMATION: Probe

<400> SEQUENCE: 21
tggaatcata ttggaacatg                                             20

<210> SEQ ID NO 22
<211> LENGTH: 20
<212> TYPE: DNA
<213> ORGANISM: Artificial sequence
<220> FEATURE:
<223> OTHER INFORMATION: Primer

<400> SEQUENCE: 22
ggcaaattca acggcacagt                                             20

<210> SEQ ID NO 23
<211> LENGTH: 20
<212> TYPE: DNA
<213> ORGANISM: Artificial sequence
<220> FEATURE:
<223> OTHER INFORMATION: Primer

<400> SEQUENCE: 23
gggtctcgct cctggaagat                                             20

<210> SEQ ID NO 24
<211> LENGTH: 27
<212> TYPE: DNA
<213> ORGANISM: Artificial sequence
<220> FEATURE:
<223> OTHER INFORMATION: Probe

<400> SEQUENCE: 24
aaggccgaga atgggaagct tgtcatc                                     27

<210> SEQ ID NO 25
<211> LENGTH: 23
<212> TYPE: DNA
```

```
<213> ORGANISM: Artificial sequence
<220> FEATURE:
<223> OTHER INFORMATION: Primer

<400> SEQUENCE: 25
tgttctagag acagccgcat ctt                                              23

<210> SEQ ID NO 26
<211> LENGTH: 21
<212> TYPE: DNA
<213> ORGANISM: Artificial sequence
<220> FEATURE:
<223> OTHER INFORMATION: Primer

<400> SEQUENCE: 26
caccgacctt caccatcttg t                                                21

<210> SEQ ID NO 27
<211> LENGTH: 24
<212> TYPE: DNA
<213> ORGANISM: Artificial sequence
<220> FEATURE:
<223> OTHER INFORMATION: Probe

<400> SEQUENCE: 27
ttgtgcagtg ccagcctcgt ctca                                             24

<210> SEQ ID NO 28
<211> LENGTH: 23
<212> TYPE: DNA
<213> ORGANISM: Artificial sequence
<220> FEATURE:
<223> OTHER INFORMATION: Primer

<400> SEQUENCE: 28
cttcaatgaa acgtgggaga act                                              23

<210> SEQ ID NO 29
<211> LENGTH: 22
<212> TYPE: DNA
<213> ORGANISM: Artificial sequence
<220> FEATURE:
<223> OTHER INFORMATION: Primer

<400> SEQUENCE: 29
tctctaggcc caaccaaaat tc                                               22

<210> SEQ ID NO 30
<211> LENGTH: 24
<212> TYPE: DNA
<213> ORGANISM: Artificial sequence
<220> FEATURE:
<223> OTHER INFORMATION: Probe

<400> SEQUENCE: 30
aaatatggtt ttgggaggct tgat                                             24

<210> SEQ ID NO 31
<211> LENGTH: 30
<212> TYPE: DNA
<213> ORGANISM: Artificial sequence
<220> FEATURE:
<223> OTHER INFORMATION: Primer

<400> SEQUENCE: 31
cagaagtaac atcactcaaa agttttgtag                                       30
```

<210> SEQ ID NO 32
<211> LENGTH: 31
<212> TYPE: DNA
<213> ORGANISM: Artificial sequence
<220> FEATURE:
<223> OTHER INFORMATION: Primer

<400> SEQUENCE: 32
gacttaattg tttatactgt tcttccacac t                                      31

<210> SEQ ID NO 33
<211> LENGTH: 32
<212> TYPE: DNA
<213> ORGANISM: Artificial sequence
<220> FEATURE:
<223> OTHER INFORMATION: Probe

<400> SEQUENCE: 33
cagcaagaca acagcataag agaactcctc ca                                     32

<210> SEQ ID NO 34
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 34
atctgttgtg atgtcgataa                                                   20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 35
gtatttagtc aagtttagag                                                   20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 36
tattacagat ttttacacat                                                   20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 37
cgtggaactg ttttcttctg                                                   20

<210> SEQ ID NO 38
<211> LENGTH: 20
<212> TYPE: DNA
<213> ORGANISM: Artificial sequence
<220> FEATURE:

<223> OTHER INFORMATION: Synthetic oligonuclotide

<400> SEQUENCE: 38
agcttaattg tgaacatttt                                          20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 39
attctggagg aaataactag                                          20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 40
aaatcttgat tttggctctg                                          20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 41
atagcaaatc ttgattttgg                                          20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 42
ctaacatagc aaatcttgat                                          20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 43
atcgtctaac atagcaaatc                                          20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 44
aggccattgg ctaaaatttt                                          20

```
<210> SEQ ID NO 45
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 45
catgtcccaa ctgaaggagg                                               20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 46
ctttaagacc atgtcccaac                                               20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 47
gcccttcgtc ttatggacaa                                               20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 48
tcattaattt ggcccttcgt                                               20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 49
tgaaatatgt cattaatttg                                               20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 50
gactgatcaa atatgttgag                                               20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonuclotide
```

<400> SEQUENCE: 51
gtttgcagcg atagatcata                                           20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 52
tcactggttt gcagcgatag                                           20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 53
agttcaagtg acatattctt                                           20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 54
agtgaagtta cttctgggtg                                           20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 55
gttttaagtg aagttacttc                                           20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 56
ctacaaaagt tttaagtgaa                                           20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 57
ggtcttccac ggtctggaga                                           20

<210> SEQ ID NO 58
<211> LENGTH: 20

```
<212> TYPE: DNA
<213> ORGANISM: Artificial sequence
<220> FEATURE:
<223> OTHER INFORMATION: Synthetic oligonuclotide

<400> SEQUENCE: 58
tagtccttct gagctgattt                                               20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 59
ggttcttgaa tactagtcct                                               20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 60
aaatttctgt gggttcttga                                               20

<210> SEQ ID NO 61
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 61
tggcttggaa gatagagaaa                                               20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 62
agtagttctt ggtgctcttg                                               20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 63
tgaagaaagg gagtagttct                                               20

<210> SEQ ID NO 64
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 64
```
attcaactga agaaagggag    20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 65
tcttatttca ttcaactgaa    20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 66
aggaatgcca tcatgtttta    20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 67
ctctgttata aatggtggta    20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 68
ttcacctctg ttataaatgg    20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 69
gtatgttcac ctctgttata    20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 70
cacttgtatg ttcacctctg    20

<210> SEQ ID NO 71
<211> LENGTH: 20
<212> TYPE: DNA
<213> ORGANISM: Artificial sequence

```
<220> FEATURE:
<223> OTHER INFORMATION: Synthetic oligonuclotide

<400> SEQUENCE: 71
catgccactt gtatgttcac                                               20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 72
agagttgctg ggtctgatgg                                               20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 73
ctgatataac atcacagtag                                               20

<210> SEQ ID NO 74
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 74
catggactac ctgatataac                                               20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 75
tgaattaatg tccatggact                                               20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 76
tctattcgat gttgaattaa                                               20

<210> SEQ ID NO 77
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 77
agttctccca cgtttcattg                                               20
```

```
<210> SEQ ID NO 78
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 78
catatttgta gttctcccac                                               20

<210> SEQ ID NO 79
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 79
aaaaccatat ttgtagttct                                               20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 80
gcctcccaaa accatatttg                                               20

<210> SEQ ID NO 81
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 81
gcccaaccaa aattctccat                                               20

<210> SEQ ID NO 82
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 82
ctctaggccc aaccaaaatt                                               20

<210> SEQ ID NO 83
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 83
atcttctcta ggcccaacca                                               20

<210> SEQ ID NO 84
<211> LENGTH: 20
<212> TYPE: DNA
<213> ORGANISM: Artificial sequence
<220> FEATURE:
<223> OTHER INFORMATION: Synthetic oligonuclotide
```

<400> SEQUENCE: 84
aacataatta gattgcttca                                                    20

<210> SEQ ID NO 85
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 85
gtcttccaac tcaattcgta                                                    20

<210> SEQ ID NO 86
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 86
ctttccagtc ttccaactca                                                    20

<210> SEQ ID NO 87
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 87
aactagatgt agcgtatagt                                                    20

<210> SEQ ID NO 88
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 88
tgatcccaag tagaaaacac                                                    20

<210> SEQ ID NO 89
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 89
caccagcctc ctgaataacc                                                    20

<210> SEQ ID NO 90
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 90
ttaggttgtt ttctccacac                                                    20

<210> SEQ ID NO 91

```
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 91
taatcctctt ctcctctctg                                               20

<210> SEQ ID NO 92
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 92
tgagacttcc aagataatcc                                               20

<210> SEQ ID NO 93
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 93
cattttgaga cttccaagat                                               20

<210> SEQ ID NO 94
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 94
gagtataacc ttccattttg                                               20

<210> SEQ ID NO 95
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 95
tggatggatc aacattttgg                                               20

<210> SEQ ID NO 96
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 96
ttcaaagctt tctgaatctg                                               20

<210> SEQ ID NO 97
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 97
```
tgcctcagtt cattcaaagc                                               20

<210> SEQ ID NO 98
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 98
tgccttttaa atttgcctca                                               20

<210> SEQ ID NO 99
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 99
attaacttgg aatgaggtta                                               20

<210> SEQ ID NO 100
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 100
agaccacatt aacttggaat                                               20

<210> SEQ ID NO 101
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 101
agattattag accacattaa                                               20

<210> SEQ ID NO 102
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 102
ataccagatt attagaccac                                               20

<210> SEQ ID NO 103
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 103
ggatttaata ccagattatt                                               20

<210> SEQ ID NO 104
<211> LENGTH: 20
<212> TYPE: DNA

```
<213> ORGANISM: Artificial sequence
<220> FEATURE:
<223> OTHER INFORMATION: Synthetic oligonuclotide

<400> SEQUENCE: 104
actgacttac ctgattttct                                               20

<210> SEQ ID NO 105
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 105
accttgtaag tcttcattgg                                               20

<210> SEQ ID NO 106
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 106
cagtgttatt cagattgtac                                               20

<210> SEQ ID NO 107
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 107
agtgtcttac catcatgttt                                               20

<210> SEQ ID NO 108
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 108
acagatgtaa ataacacttt                                               20

<210> SEQ ID NO 109
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 109
gtccccttac catcaagcct                                               20

<210> SEQ ID NO 110
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 110
gggaagatac tttgaagata                                               20
```

<210> SEQ ID NO 111
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 111
caccagcctc ctaaaggaga                                              20

<210> SEQ ID NO 112
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 112
aataatttaa ttgtgtgcat                                              20

<210> SEQ ID NO 113
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 113
cactctggat gcaattacta                                              20

<210> SEQ ID NO 114
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 114
aaggtctgga tccactctgg                                              20

<210> SEQ ID NO 115
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 115
tttggctctg aaggtgcaga                                              20

<210> SEQ ID NO 116
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 116
tcatccaaca tagcaaatct                                              20

<210> SEQ ID NO 117
<211> LENGTH: 20
<212> TYPE: DNA
<213> ORGANISM: Artificial sequence
<220> FEATURE:

<223> OTHER INFORMATION: Synthetic oligonuclotide

<400> SEQUENCE: 117
tgacatcatc caacatagca                                              20

<210> SEQ ID NO 118
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 118
aattttgaca tcatccaaca                                              20

<210> SEQ ID NO 119
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 119
gctaaaattt tgacatcatc                                              20

<210> SEQ ID NO 120
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 120
aggccattcg ctaaaatttt                                              20

<210> SEQ ID NO 121
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 121
cccagctgca ggaggccatt                                              20

<210> SEQ ID NO 122
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 122
catgacccag ctgcaggagg                                              20

<210> SEQ ID NO 123
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 123
ttaagtccat gacccagctg                                              20

```
<210> SEQ ID NO 124
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 124
gacaaaatct ttaagtccat                                               20

<210> SEQ ID NO 125
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 125
ttatggacaa aatctttaag                                               20

<210> SEQ ID NO 126
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 126
ttgagcttct gaaatatgtc                                               20

<210> SEQ ID NO 127
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 127
atatgttgag cttctgaaat                                               20

<210> SEQ ID NO 128
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 128
atcaaatatg ttgagcttct                                               20

<210> SEQ ID NO 129
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 129
ggttcgaagt gataggtcat                                               20

<210> SEQ ID NO 130
<211> LENGTH: 20
<212> TYPE: DNA
<213> ORGANISM: Artificial sequence
<220> FEATURE:
<223> OTHER INFORMATION: Synthetic oligonuclotide
```

<400> SEQUENCE: 130
tagtgtagat gtagttcttc 20

<210> SEQ ID NO 131
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 131
gacatgttct tcacctcctc 20

<210> SEQ ID NO 132
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 132
tgagttcagt tctactgaca 20

<210> SEQ ID NO 133
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 133
tcaagctttg agttcagttc 20

<210> SEQ ID NO 134
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 134
gtcttctctt ccagcagact 20

<210> SEQ ID NO 135
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 135
gttgaagggc tgtcttctct 20

<210> SEQ ID NO 136
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 136
ctgaccttgt gttgaagggc 20

<210> SEQ ID NO 137
<211> LENGTH: 20

```
<212> TYPE: DNA
<213> ORGANISM: Artificial sequence
<220> FEATURE:
<223> OTHER INFORMATION: Synthetic oligonuclotide

<400> SEQUENCE: 137
ccaaagccct gaccttgtgt                                              20

<210> SEQ ID NO 138
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 138
ttagctgctc ctccaaagcc                                              20

<210> SEQ ID NO 139
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 139
cttagaatta agttggttag                                              20

<210> SEQ ID NO 140
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 140
ggtgctcctg agccccagct                                              20

<210> SEQ ID NO 141
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 141
tgatgttact tctgggtgct                                              20

<210> SEQ ID NO 142
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 142
tgctgttcta caaaactttt                                              20

<210> SEQ ID NO 143
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 143
```
aggagttctc ttatgctgtt                                              20

<210> SEQ ID NO 144
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 144
tctggaggag ttctcttatg                                              20

<210> SEQ ID NO 145
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 145
cacactctgg aggagttctc                                              20

<210> SEQ ID NO 146
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 146
gggttcttga ataccagtct                                              20

<210> SEQ ID NO 147
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 147
gaaagagaat tttctgaggg                                              20

<210> SEQ ID NO 148
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 148
gcaggaaggt catcttgttc                                              20

<210> SEQ ID NO 149
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 149
gagcagtcgg caggaaggtc                                              20

<210> SEQ ID NO 150
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 150
tacacgccac ttgtatgttc                                        20

<210> SEQ ID NO 151
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 151
ttaatagtgt acacgccact                                        20

<210> SEQ ID NO 152
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 152
agacattaaa cccttgggag                                        20

<210> SEQ ID NO 153
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 153
ctgcctgatt gggtatcaca                                        20

<210> SEQ ID NO 154
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 154
ccatctttcc ggtgttgaat                                        20

<210> SEQ ID NO 155
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 155
gaagtcctgt gagccatctt                                        20

<210> SEQ ID NO 156
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 156
ttctccatcg agcctcccaa                                        20

<210> SEQ ID NO 157
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 157
gttggactat agcatagatc                                              20

<210> SEQ ID NO 158
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 158
atgtagttag actgttggac                                              20

<210> SEQ ID NO 159
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 159
acgtagtgct tgctgtcttt                                              20

<210> SEQ ID NO 160
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 160
gcccaggtga aaggagtatt                                              20

<210> SEQ ID NO 161
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 161
tgtagcgtgt agttggtttc                                              20

<210> SEQ ID NO 162
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 162
ccacatgtag cgtgtagttg                                              20

<210> SEQ ID NO 163
<211> LENGTH: 20
<212> TYPE: DNA
<213> ORGANISM: Artificial sequence
<220> FEATURE:
<223> OTHER INFORMATION: Synthetic oligonuclotide

```
<400> SEQUENCE: 163
ctcagccaca tgtagcgtgt                                              20

<210> SEQ ID NO 164
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 164
gcaatctcag ccacatgtag                                              20

<210> SEQ ID NO 165
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 165
atcaggtctg tgtgctctgg                                              20

<210> SEQ ID NO 166
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 166
atgtagaaaa catcaggtct                                              20

<210> SEQ ID NO 167
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 167
tctgtgattc catgtagaaa                                              20

<210> SEQ ID NO 168
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 168
tctggacagt agagctgtcc                                              20

<210> SEQ ID NO 169
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 169
aactttctgg acagtagagc                                              20

<210> SEQ ID NO 170
```

```
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 170
accaccagcc acctgagtaa                                              20

<210> SEQ ID NO 171
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 171
ttctccacat atgtcattcc                                              20

<210> SEQ ID NO 172
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 172
ggttgttttc tccacatatg                                              20

<210> SEQ ID NO 173
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 173
tggtctggat ttggttctgg                                              20

<210> SEQ ID NO 174
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 174
tctctctggt ctggatttgg                                              20

<210> SEQ ID NO 175
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 175
tagagctttc tgctctgagg                                              20

<210> SEQ ID NO 176
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 176
```
gtggtgggct ggagcatcat                                              20

<210> SEQ ID NO 177
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 177
tgaagcttct taggtggtgg                                              20

<210> SEQ ID NO 178
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 178
tgtctcagtt cagttgaagc                                              20

<210> SEQ ID NO 179
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 179
tcgggaggac tttaatattt                                              20

<210> SEQ ID NO 180
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 180
ggaacttctc cctcctgtcc                                              20

<210> SEQ ID NO 181
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 181
taacaatgag tttaaaccta                                              20

<210> SEQ ID NO 182
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 182
tctgatctta acaatgagtt                                              20

<210> SEQ ID NO 183
<211> LENGTH: 19
<212> TYPE: DNA

```
<213> ORGANISM: Artificial sequence
<220> FEATURE:
<223> OTHER INFORMATION: Synthetic oligonuclotide

<400> SEQUENCE: 183
cgagaggcgg acgggaccg                                                    19

<210> SEQ ID NO 184
<211> LENGTH: 21
<212> TYPE: DNA
<213> ORGANISM: Artificial sequence
<220> FEATURE:
<223> OTHER INFORMATION: Synthetic oligonuclotide

<400> SEQUENCE: 184
cgagaggcgg acgggaccgt t                                                 21

<210> SEQ ID NO 185
<211> LENGTH: 21
<212> TYPE: DNA
<213> ORGANISM: Artificial sequence
<220> FEATURE:
<223> OTHER INFORMATION: Synthetic oligonuclotide

<400> SEQUENCE: 185
ttgctctccg cctgccctgg c                                                 21

<210> SEQ ID NO 186
<211> LENGTH: 19
<212> TYPE: DNA
<213> ORGANISM: Artificial sequence
<220> FEATURE:
<223> OTHER INFORMATION: Synthetic oligonuclotide

<400> SEQUENCE: 186
gctctccgcc tgccctggc                                                    19

<210> SEQ ID NO 187
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 187
ccttccctga aggttcctcc                                                   20

<210> SEQ ID NO 188
<211> LENGTH: 19
<212> TYPE: DNA
<213> ORGANISM: Artificial sequence
<220> FEATURE:
<223> OTHER INFORMATION: Primer

<400> SEQUENCE: 188
cacctgggca gtcacgaaa                                                    19

<210> SEQ ID NO 189
<211> LENGTH: 18
<212> TYPE: DNA
<213> ORGANISM: Artificial sequence
<220> FEATURE:
<223> OTHER INFORMATION: Primer

<400> SEQUENCE: 189
ggagggcccc aggatat                                                      18
```

<210> SEQ ID NO 190
<211> LENGTH: 27
<212> TYPE: DNA
<213> ORGANISM: Artificial sequence
<220> FEATURE:
<223> OTHER INFORMATION: Probe

<400> SEQUENCE: 190
cacgctacat gtggctgaga ttcgtgg                                27

<210> SEQ ID NO 191
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 191
gtgacatatt cttcacctct                                       20

<210> SEQ ID NO 192
<211> LENGTH: 20
<212> TYPE: DNA
<213> ORGANISM: Artificial sequence
<220> FEATURE:
<223> OTHER INFORMATION: Synthetic oligonuclotide

<400> SEQUENCE: 192
tttaagtgac gttacctctg                                       20

<210> SEQ ID NO 193
<211> LENGTH: 1272
<212> TYPE: DNA
<213> ORGANISM: Rattus norvegicus
<220> FEATURE:
<221> NAME/KEY: CDS
<222> LOCATION: (1)..(1272)

<400> SEQUENCE: 193

```
atg cac aca att aag ctg ctc ctt ttt gtt gtt cct cta gta att tcg     48
Met His Thr Ile Lys Leu Leu Leu Phe Val Val Pro Leu Val Ile Ser
1               5                   10                  15 tcc aga gtt gat cca gac ctt tcg cca ttt gat tct gta ccg tca gag     96
Ser Arg Val Asp Pro Asp Leu Ser Pro Phe Asp Ser Val Pro Ser Glu
            20                  25                  30 cca aaa tca aga ttt gct atg ttg gat gat gtc aaa att tta gcc aat    144
Pro Lys Ser Arg Phe Ala Met Leu Asp Asp Val Lys Ile Leu Ala Asn
        35                  40                  45 ggc ctc ctg cag ctg ggt cat ggt ctt aaa gat ttt gtc cat aag aca    192
Gly Leu Leu Gln Leu Gly His Gly Leu Lys Asp Phe Val His Lys Thr
    50                  55                  60 aag gga caa att aat gac ata ttt cag aag ctc aac ata ttt gat cag    240
Lys Gly Gln Ile Asn Asp Ile Phe Gln Lys Leu Asn Ile Phe Asp Gln
65                  70                  75                  80 tgt ttt tat gac cta tca ctt caa acc aat gaa atc aaa gaa gag gaa    288
Cys Phe Tyr Asp Leu Ser Leu Gln Thr Asn Glu Ile Lys Glu Glu Glu
                85                  90                  95 aag gag cta aga aga acc aca tct aaa cta caa gtt aaa aac gaa gag    336
Lys Glu Leu Arg Arg Thr Thr Ser Lys Leu Gln Val Lys Asn Glu Glu
            100                 105                 110 gtg aag aat atg tca ctt gaa ctg aac tca aag ctt gaa agt cta ctg    384
Val Lys Asn Met Ser Leu Glu Leu Asn Ser Lys Leu Glu Ser Leu Leu
        115                 120                 125
```

```
gag gag aag atg gcg ctc caa cac aga gtc agg gct ttg gag gaa cag     432
Glu Glu Lys Met Ala Leu Gln His Arg Val Arg Ala Leu Glu Glu Gln
        130                 135                 140 ctg acc agc ttg gtt cag aac ccg cct ggg gct cgg gag cac cca gag     480
Leu Thr Ser Leu Val Gln Asn Pro Pro Gly Ala Arg Glu His Pro Glu
145                 150                 155                 160 gta acg tca ctt aaa agt ttt gta gaa cag caa gat aac agc ata aga     528
Val Thr Ser Leu Lys Ser Phe Val Glu Gln Gln Asp Asn Ser Ile Arg
                165                 170                 175 gaa ctc ctc cag agt gtg gaa gaa caa tat aaa caa cta agt caa cag     576
Glu Leu Leu Gln Ser Val Glu Glu Gln Tyr Lys Gln Leu Ser Gln Gln
            180                 185                 190 cac att cag ata aaa gaa ata gaa aat cag ctc aga aag act ggc att     624
His Ile Gln Ile Lys Glu Ile Glu Asn Gln Leu Arg Lys Thr Gly Ile
        195                 200                 205 caa gaa ccc act gaa aat tct ctt tat tct aaa cca aga gca cca aga     672
Gln Glu Pro Thr Glu Asn Ser Leu Tyr Ser Lys Pro Arg Ala Pro Arg
    210                 215                 220 act act ccc cct ctt cat ctg aag gaa gca aaa aat ata gaa caa gat     720
Thr Thr Pro Pro Leu His Leu Lys Glu Ala Lys Asn Ile Glu Gln Asp
225                 230                 235                 240 gat ctg cct gct gac tgc tct gcc att tat aac aga ggt gaa cat aca     768
Asp Leu Pro Ala Asp Cys Ser Ala Ile Tyr Asn Arg Gly Glu His Thr
                245                 250                 255 agt ggc gtg tat act att aga cca agc agc tct caa gtg ttt aat gtc     816
Ser Gly Val Tyr Thr Ile Arg Pro Ser Ser Ser Gln Val Phe Asn Val
            260                 265                 270 tac tgt gac acc caa tca gga gaa ttc tgg ttg ggc cta gag aag atc     864
Tyr Cys Asp Thr Gln Ser Gly Glu Phe Trp Leu Gly Leu Glu Lys Ile
        275                 280                 285 tac gct ata gtc aaa cag tct aac tac atc tta cga ctg gag cta caa     912
Tyr Ala Ile Val Lys Gln Ser Asn Tyr Ile Leu Arg Leu Glu Leu Gln
    290                 295                 300 gac tgg aag gac agc aag cac tat gct gaa tat tcc ttt cat ctg ggc     960
Asp Trp Lys Asp Ser Lys His Tyr Ala Glu Tyr Ser Phe His Leu Gly
305                 310                 315                 320 aat cat gaa acc aac tac acg cta cat gtg gct gag att gct gcc aat    1008
Asn His Glu Thr Asn Tyr Thr Leu His Val Ala Glu Ile Ala Ala Asn
                325                 330                 335 atc cct gag gcc cta cca gaa cac aga gac ctg atg ttt tct aca tgg    1056
Ile Pro Glu Ala Leu Pro Glu His Arg Asp Leu Met Phe Ser Thr Trp
            340                 345                 350 gat cac aga gca aag gga cag ctc tac tgt cca gaa agt tat tca ggt    1104
Asp His Arg Ala Lys Gly Gln Leu Tyr Cys Pro Glu Ser Tyr Ser Gly
        355                 360                 365 ggc tgg tgg ttc agt gac atg tgt gga gaa aac aac cta aat ggt aaa    1152
Gly Trp Trp Phe Ser Asp Met Cys Gly Glu Asn Asn Leu Asn Gly Lys
    370                 375                 380 tac aac aaa ccc aga gcc aaa tcc aaa cca gag cgg aga aga ggg atc    1200
Tyr Asn Lys Pro Arg Ala Lys Ser Lys Pro Glu Arg Arg Arg Gly Ile
385                 390                 395                 400 tcc tgg agg cct cgg ggc gga aag ctc tac tct atc aaa tca tct aaa    1248
Ser Trp Arg Pro Arg Gly Gly Lys Leu Tyr Ser Ile Lys Ser Ser Lys
                405                 410                 415 atg atg ctc cag ccg acc acc taa                                    1272
Met Met Leu Gln Pro Thr Thr
            420
```

MODULATION OF ANGIOPOIETIN-LIKE 3 EXPRESSION

CROSS REFERENCED TO RELATED APPLICATIONS

This application is a divisional of U.S. application Ser. No. 13/520,997 filed Oct. 4, 2012 (now U.S. Pat. No. 8,653,047), which is a U.S. National Phase filing under 35 U.S.C. 371 claiming priority to International Serial No. PCT/US2011/020606 filed Jan. 7, 2011, which is the non-provisional application of U.S. Provisional Application No. 61/293,604, filed Jan. 8, 2010, each of which is incorporated herein by reference in its entirety.

SEQUENCE LISTING

The present application is being filed along with a Sequence Listing in electronic format. The Sequence Listing is provided as a file entitled BIOL0120USD1SEQ.txt, created on Jan. 3, 2012 which is 56 Kb in size. The information in the electronic format of the sequence listing is incorporated herein by reference in its entirety.

1. Field of the Invention

Provided herein are methods, compounds, and compositions for reducing expression of angiopoietin-like 3 (ANGPTL3) mRNA and protein in an animal. Also, provided herein are methods, compounds, and compositions having an ANGPTL3 inhibitor for reducing ANGPTL3 related diseases or conditions in an animal. Such methods, compounds, and compositions are useful, for example, to treat, prevent, delay or ameliorate any one or more of cardiovascular disease or metabolic syndrome, or a symptom thereof, in an animal.

2. Background

Diabetes and obesity (sometimes collectively referred to as "diabesity") are interrelated in that obesity is known to exacerbate the pathology of diabetes and greater than 60% of diabetics are obese. Most human obesity is associated with insulin resistance and leptin resistance. In fact, it has been suggested that obesity may have an even greater impact on insulin action than diabetes itself (Sindelka et al., *Physiol Res.*, 2002, 51, 85-91). Additionally, several compounds on the market for the treatment of diabetes are known to induce weight gain, a very undesirable side effect to the treatment of this disease.

Cardiovascular disease is also interrelated to obesity and diabetes. Cardiovascular disease encompasses a wide variety of etiologies and has an equally wide variety of causative agents and interrelated players. Many causative agents contribute to symptoms such as elevated plasma levels of cholesterol, including non-HDL cholesterol, as well as other lipid-related disorders. Such lipid-related disorders, generally referred to as dyslipidemia, include hyperlipidemia, hypercholesterolemia and hypertriglyceridemia among other indications. Elevated non-HDL cholesterol is associated with atherogenesis and its sequelae, including cardiovascular diseases such as arteriosclerosis, coronary artery disease, myocardial infarction, ischemic stroke, and other forms of heart disease. These rank as the most prevalent types of illnesses in industrialized countries. Indeed, an estimated 12 million people in the United States suffer with coronary artery disease and about 36 million require treatment for elevated cholesterol levels.

Epidemiological and experimental evidence has shown that high levels of circulating triglyceride (TG) can contribute to cardiovascular disease and a myriad of metabolic disorders (Valdivielso et al., 2009, *Atherosclerosis.* 207(2):573-8; Zhang et al., 2008, *Circ Res.* 1; 102(2):250-6). TG derived from either exogenous or endogenous sources is incorporated and secreted in chylomicrons from the intestine or in very low density lipoproteins (VLDL) from the liver. Once in circulation, TG is hydrolyzed by lipoprotein lipase (LpL) and the resulting free fatty acids can then be taken up by local tissues and used as an energy source. Due to the profound effect LpL has on plasma TG and metabolism in general, discovering and developing compounds that affect LpL activity are of great interest.

Metabolic syndrome is a combination of medical disorders that increase one's risk for cardiovascular disease and diabetes. The symptoms, including high blood pressure, high triglycerides, decreased HDL and obesity, tend to appear together in some individuals. It affects a large number of people in a clustered fashion. In some studies, the prevalence in the USA is calculated as being up to 25% of the population. Metabolic syndrome is known under various other names, such as (metabolic) syndrome X, insulin resistance syndrome, Reaven's syndrome or CHAOS. With the high prevalence of cardiovascular disorders and metabolic disorders there remains a need for improved approaches to treat these conditions The angiopoietins are a family of secreted growth factors. Together with their respective endothelium-specific receptors, the angiopoietins play important roles in angiogenesis. One family member, angiopoietin-like 3 (also known as ANGPT5, ANGPTL3, or angiopoietin 5), is predominantly expressed in the liver, and is thought to play a role in regulating lipid metabolism (Kaplan et al., *J. Lipid Res.*, 2003, 44, 136-143).

The human gene for angiopoietin-like 3 was identified and cloned as a result of searches of assembled EST databases. The full-length human cDNA codes for a polypeptide of 460 amino acids which has the characteristic structural features of angiopoietins: a signal peptide, an extended helical domain, a short linker peptide, and a globular fibrinogen homology domain (FHD). The mouse angiopoietin-like 3 cDNA was found to encode a 455 amino acid polypeptide with 76% identity to the human polypeptide. An alignment of angiopoietins showed that angiopoietin-like 3, unlike other family members, does not contain the motif of acidic residues determining a calcium binding site. Northern blot analysis revealed expression principally in the liver of adult tissues, with murine embryo Northern blots showing the presence of transcripts as early as day 15, suggesting that angiopoietin-like 3 is expressed early during liver development and that expression is maintained in adult liver. The mouse gene maps to chromosome 4, and the human gene was mapped to the 1p31 region (Conklin et al., *Genomics*, 1999, 62, 477-482).

KK obese mice have a multigenic syndrome of moderate obesity and a diabetic phenotype that resembles human hereditary type 2 diabetes. These mice show signs of hyperinsulinemia, hyperglycemia, and hyperlipidemia. A strain of KK mice called KK/San has significantly low plasma lipid levels despite signs of hyperinsulinemia and hyperglycemia. The mutant phenotype is inherited recessively, and the locus was named hypolipidemia (hypl). The locus maps to the middle of chromosome 4, and the gene was identified as angiopoietin-like 3 through positional cloning. Injection of recombinant adenoviruses containing the full-length mouse or human angiopoietin-like 3 cDNA in the mutant KK/San mice caused an increase in plasma levels of triglyceride, total cholesterol and non-esterified fatty acides (NEFA). Similarly, injection of recombinant angiopoietin-like 3 protein into the mutant mice increased levels of triglycerides and non-esterified fatty acids. (Koichi et al., *Nat. Genet.*, 2002, 30, 151-157).

In another study focusing on the metabolic pathways of triglycerides in KK/San mice, overexpression of angiopoietin-like 3 resulted in a marked increase of triglyceride-enriched very low density lipoportien (VLDL). Differences in the hepatic VLDL triglyceride secretion rate were not significant between wild-type KK and KK/San mice. However, studies with labeled VLDL suggested that the low plasma triglyceride levels in KK/San mice were primarily due to enhanced lipolysis of VLDL triglycerides rather than to enhanced whole particle uptake. The plasma apoB100 and apoB48 levels of KK/San mice were similar to wild-type KK mice. ApoCIII-deficient mice have a similar phenotype to KK/San mice, and ApoCIII is thought to modulate VLDL triglyceride metabolism through the inhibition of lipase-mediated hydrolysis of VLDL triglycerides. In vitro analysis of recombinant protein revealed that angiopoietin-like 3 directly inhibits lipoprotein lipase (LPL) activity (Shimizugawa et al., *J. Biol. Chem.*, 2002, 277, 33742-33748).

Consistent with a role in lipid metabolism, angiopoietin-like 3 mRNA was found to be upregulated in C57BL/6J mice fed normal chow diets with 4% cholesterol and in mice treated with the liver X receptor (LXR) agonist T0901317. LXRs are ligand-activated transcription factors which play a role in the regulation of genes that govern cholesterol homeostasis in the liver and peripheral tissues. In addition to cholesterol metabolism, LXRs may also play a role in regulation of fatty acid metabolism. Treatment of HepG2 cells with natural or synthetic agents which activate LXR caused increased angiopoietin-like 3 expression. The promoter of the human angiopoietin-like 3 gene was found to contain an LXR response element. In addition, the promoter contained several potential binding sites for other transcription factors including HNF-1, HNF-4, and C/EBP. (Kaplan et al., *J. Lipid Res.*, 2003, 44, 136-143).

Treatment of rodents with T0901317 is associated with triglyceride accumulation in the liver and plasma. The liver triglyceride accumulation has been explained by increased expression of the sterol regulatory element binding protein-1c (SREBP1c) and fatty acid synthase (FAS), both of which are targets of LXR. T0901317 failed to increase plasma triglyceride concentration in angiopoietin-like 3 deficient mice, while the stimulated accumulation of hepatic triglyceride was similar to that observed in treated wild type mice. The rise in plasma triglyceride in wild-type mice treated with T0901317 parallels an induction of angiopoietin-like 3 mRNA in the liver and an increase in plasma concentration of the protein. (Inaba et al., *J. Biol. Chem.*, 2003, 278, 21344-21351).

Further studies addressed the mechanism of the increase in plasma free fatty acid (FFA) levels observed in KK/Snk mice treated with exogenous angiopoietin-like 3. Probe of fixed human tissues with a fluorescence-labeled angiopoietin-like 3 protein demonstrated strong binding only on adipose tissue. Furthermore, radio labeled protein binding was examined in 3T3-L1 adipocytes and was found to be saturable and specific. Incubation of 3T3-L1 adipocytes with angiopoietin-like 3 led to enhanced release of FFA and glycerol into the culture medium. (Shimamura et al., *Biochem. Biophys. Res. Commun.*, 2003, 301, 604-609).

In a study using streptozotocin-treated mice (STZ) to model the insulin-deficient state and db/db mice to model the insulin-resistant diabetic state, larger amounts of hepatic angiopoietin-like 3 were observed in diabetic mice as compared to control animals. Both models of diabetes showed hypertriglyceridemia, and the hyperlipidemia observed was explained at least partially by the increased expression of angiopoietin-like 3. These results suggested that angiopoietin-like 3 is a link between diabetes and dyslipidemia, with elevation promoting hyperlipidemia (Inukai et al., *Biochem. Biophys. Res. Commun.*, 2004, 317, 1075-1079).

A subsequent study examined the regulation of angiopoietin-like 3 by leptin and insulin, both of which are key players in the metabolic syndrome. Angiopoietin-like 3 expression and plasma protein levels were increased in leptin-resistant db/db and leptin-deficient ob/ob mice relative to controls. Supplementation of ob/ob mice with leptin decreased angiopoietin-like 3 levels. The alterations in expression were associated with alterations in plasma triglyceride and free fatty acid levels. Gene expression and plasma protein levels were also increased in insulin-deficient STZ-treated mice. (Shimamura et al., *Biochem Biophys Res Commun*, 2004, 322, 1080-1085).

In accord with its membership in the angiopoietin family, recombinant angiopoietin-like 3 protein was found to bind to $\alpha_v\beta_3$ integrin and induced integrin $\alpha_v\beta_3$-dependent haptotactic endothelial cell adhesion and migration. It also stimulated signal transduction pathways characteristic for integrin activation. Angiopoietin-like 3 strongly induced angiogenesis in the rat corneal angiogenesis assay. (Camenisch et al., *J. Biol. Chem.*, 2002, 277, 17281-17290).

Genome-wide association scans (GWAS) surveying the genome for common variants associated with plasma concentrations of HDL, LDL and triglyceride were undertaken by several groups. The GWAS studies found an association between triglycerides and single-nucleotide polymorphisms (SNPs) near ANGPTL3 (Willer et al., Nature Genetics, 2008, 40(2):161-169).

U.S. Pat. No. 7,267,819, application U.S. Ser. No. 12/128,545, and application U.S. Ser. No. 12/001,012 generally describe angiopoietin-like 3 agonists and antagonists.

PCT publications WO/02101039 (EP02733390) and WO/0142499 (U.S. Ser. No. 10/164,030) disclose a nucleic acid sequence complementary to mouse angiopoietin-like 3 (Ryuta, 2002; Ryuta, 2001).

There is a currently a lack of acceptable options for treating cardiovascular and metabolic disorders. It is therefore an object herein to provide compounds and methods for the treatment of such diseases and disorder.

The potential role of angiopoietin-like 3 in lipid metabolism makes it an attractive target for investigation. Antisense technology is emerging as an effective means for reducing the expression of certain gene products and may therefore prove to be uniquely useful in a number of therapeutic, diagnostic, and research applications for the modulation of angiopoietin-like 3.

SUMMARY OF THE INVENTION

Provided herein are antisense compounds useful for modulating gene expression and associated pathways via antisense mechanisms of action such as RNaseH, RNAi and dsRNA enzymes, as well as other antisense mechanisms based on target degradation or target occupancy.

Provided herein are methods, compounds, and compositions for inhibiting expression of ANGPTL3 and treating, preventing, delaying or ameliorating a ANGPTL3 related disease, condition or a symptom thereof. In certain embodiments, the ANGPTL3 related disease or condition is cardiovascular disease or metabolic disease.

In certain embodiments, the compounds or compositions of the invention comprise a modified oligonucleotide 10 to 30 linked nucleosides in length targeted to ANGPTL3. The ANGPTL target can have a sequence selected from any one of SEQ ID NOs: 1-5. The modified oligonucleotide targeting ANGPTL3 can have a nucleobase sequence comprising at least 8 contiguous nucleobases complementary to an equal length portion of SEQ ID NOs: 1-5. The modified oligonucleotide targeting ANGPTL3 can have a nucleobase sequence comprising at least 8 contiguous nucleobases of a nucleobase sequence selected from any of SEQ ID NO: 34-182. The modified oligonucleotide can have a nucleobase sequence comprising at least 8, 9, 10, 11, 12, 13, 14, 15, 16, 17, 18, 19 or 20 contiguous nucleobases of a nucleobase sequence selected from a sequence recited in any one of SEQ ID NOs: 34-182. The contiguous nucleobase portion of the modified oligonucleotide can be complementary to an equal length portion of an ANGPTL3 region selected from any one of SEQ ID NOs: 1-5. The ANGPTL3 region can be chosen from one or more of the following regions: 22-52, 116-145, 637-720, 953-983, 1333-1469 and 1463-1489.

Certain embodiments provide a method of reducing ANGPTL3 expression in an animal comprising administering to the animal a compound comprising the modified oligonucleotide targeting ANGPTL3 described herein.

Certain embodiments provide a method of reducing apoC-III expression, triglyceride levels, cholesterol levels, low-density lipoprotein (LDL) or glucose levels in an animal comprising administering to the animal a compound comprising the modified oligonucleotide targeted to ANGPTL3 described herein, wherein the modified oligonucleotide reduces ANGPTL3 expression in the animal.

Certain embodiments provide a method of ameliorating cardiovascular disease or metabolic disease in an animal comprising administering to the animal a compound comprising a modified oligonucleotide targeted to ANGPTL3 described herein, wherein the modified oligonucleotide reduces ANGPTL3 expression in the animal.

Certain embodiments provide a method for treating an animal with cardiovascular disease or metabolic disease comprising: 1) identifying the animal with cardiovascular disease or metabolic disease, and 2) administering to the animal a therapeutically effective amount of a compound comprising a modified oligonucleotide consisting of 20 linked nucleosides and having a nucleobase sequence at least 90% complementary to SEQ ID NO: 1-5 as measured over the entirety of said modified oligonucleotide, thereby treating the animal with cardiovascular disease or metabolic disease. In certain embodiments, the therapeutically effective amount of the compound administered to the animal reduces cardiovascular disease or metabolic disease in the animal.

Certain embodiments provide a method for decreasing one or more of ANGPTL3 levels, LDL levels, apoC-III levels, triglyceride levels, cholesterol levels, glucose levels, fat pad weight, cardiovascular disease and metabolic disease in a human by administering an ANGPTL3 inhibitor comprising a modified oligonucleotide as described herein.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques can be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5' position. A 5-methylcytosine is a modified nucleobase.

"About" means within ±10% of a value. For example, if it is stated, "a marker may be increased by about 50%", it is implied that the marker may be increased between 45%-55%

"Active pharmaceutical agent" means the substance or substances in a pharmaceutical composition that provide a therapeutic benefit when administered to an individual. For example, in certain embodiments an antisense oligonucleotide targeted to ANGPTL3 is an active pharmaceutical agent.

"Active target region" or "target region" means a region to which one or more active antisense compounds is targeted.

"Active antisense compounds" means antisense compounds that reduce target nucleic acid levels or protein levels.

"Adipogenesis" means the development of fat cells from preadipocytes. "Lipogenesis" means the production or formation of fat, either fatty degeneration or fatty infiltration.

"Adiposity" or "Obesity" refers to the state of being obese or an excessively high amount of body fat or adipose tissue in relation to lean body mass. The amount of body fat includes concern for both the distribution of fat throughout the body and the size and mass of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese. The term "Obesity" as used herein includes conditions where there is an increase in body fat beyond the physical requirement as a result of excess accumulation of adipose tissue in the body. The term "obesity" includes, but is not limited to, the following conditions: adult-onset obesity; alimentary obesity; endogenous or metabolic obesity; endocrine obesity; familial obesity; hyperinsulinar obesity; hyperplastic-hypertrophic obesity; hypogonadal obesity; hypothyroid obesity; lifelong obesity; morbid obesity and exogenous obesity.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing an agent to an animal, and includes, but is not limited to, administering by a medical professional and self-administering.

"Agent" means an active substance that can provide a therapeutic benefit when administered to an animal. "First Agent" means a therapeutic compound of the invention. For example, a first agent can be an antisense oligonucleotide targeting ANGPTL3. "Second agent" means a second therapeutic compound of the invention (e.g. a second antisense oligonucleotide targeting ANGPTL3) and/or a non-ANGPTL3 therapeutic compound.

"Amelioration" refers to a lessening of at least one indicator, sign, or symptom of an associated disease, disorder, or condition. The severity of indicators can be determined by subjective or objective measures, which are known to those skilled in the art.

"ANGPTL3" means any nucleic acid or protein of ANGPTL3.

"ANGPTL3 expression" means the level of mRNA transcribed from the gene encoding ANGPTL3 or the level of protein translated from the mRNA. ANGPTL3 expression can be determined by art known methods such as a Northern or Western blot.

"ANGPTL3 nucleic acid" means any nucleic acid encoding ANGPTL3. For example, in certain embodiments, a ANGPTL3 nucleic acid includes a DNA sequence encoding ANGPTL3, a RNA sequence transcribed from DNA encoding ANGPTL3 (including genomic DNA comprising introns and exons), and a mRNA sequence encoding ANGPTL3. "ANGPTL3 mRNA" means a mRNA encoding an ANGPTL3 protein.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"ApoB-containing lipoprotein" means any lipoprotein that has apolipoprotein B as its protein component, and is understood to include LDL, VLDL, IDL, and lipoprotein(a) and can be generally targeted by lipid lowering agent and therapies. "ApoB-100-containing LDL" means ApoB-100 isoform containing LDL.

"Atherosclerosis" means a hardening of the arteries affecting large and medium-sized arteries and is characterized by the presence of fatty deposits. The fatty deposits are called "atheromas" or "plaques," which consist mainly of cholesterol and other fats, calcium and scar tissue, and damage the lining of arteries.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Cardiovascular disease" or "cardiovascular disorder" refers to a group of conditions related to the heart, blood vessels, or the circulation. Examples of cardiovascular diseases or disorders include, but are not limited to, aneurysm, angina, arrhythmia, atherosclerosis, cerebrovascular disease (stroke), coronary heart disease, hypertension, dyslipidemia, hyperlipidemia, and hypercholesterolemia.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more agents to an individual. The two or more agents can be in a single pharmaceutical composition, or can be in separate pharmaceutical compositions. Each of the two or more agents can be administered through the same or different routes of administration. Co-administration encompasses parallel or sequential administration.

"Cholesterol" is a sterol molecule found in the cell membranes of all animal tissues. Cholesterol must be transported in an animal's blood plasma by lipoproteins including very low density lipoprotein (VLDL), intermediate density lipoprotein (IDL), low density lipoprotein (LDL), and high density lipoprotein (HDL). "Plasma cholesterol" refers to the sum of all lipoproteins (VDL, IDL, LDL, HDL) esterified and/or non-estrified cholesterol present in the plasma or serum.

"Cholesterol absorption inhibitor" means an agent that inhibits the absorption of exogenous cholesterol obtained from diet.

"Complementarity" means the capacity for pairing between nucleobases of a first nucleic acid and a second nucleic acid. In certain embodiments, complementarity between the first and second nucleic acid may be between two DNA strands, between two RNA strands, or between a DNA and an RNA strand. In certain embodiments, some of the nucleobases on one strand are matched to a complementary hydrogen bonding base on the other strand. In certain embodiments, all of the nucleobases on one strand are matched to a complementary hydrogen bonding base on the other strand. In certain embodiments, a first nucleic acid is an antisense compound and a second nucleic acid is a target nucleic acid. In certain such embodiments, an antisense oligonucleotide is a first nucleic acid and a target nucleic acid is a second nucleic acid.

"Contiguous nucleobases" means nucleobases immediately adjacent to each other.

"Coronary heart disease (CHD)" means a narrowing of the small blood vessels that supply blood and oxygen to the heart, which is often a result of atherosclerosis.

"Deoxyribonucleotide" means a nucleotide having a hydrogen at the 2' position of the sugar portion of the nucleotide. Deoxyribonucleotides may be modified with any of a variety of substituents.

"Diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

"Diabetic dyslipidemia" or "type 2 diabetes with dyslipidemia" means a condition characterized by Type 2 diabetes, reduced HDL-C, elevated triglycerides, and elevated small, dense LDL particles.

"Diluent" means an ingredient in a composition that lacks pharmacological activity, but is pharmaceutically necessary or desirable. For example, the diluent in an injected composition can be a liquid, e.g. saline solution.

"Dyslipidemia" refers to a disorder of lipid and/or lipoprotein metabolism, including lipid and/or lipoprotein overproduction or deficiency. Dyslipidemias may be manifested by elevation of lipids such as cholesterol and triglycerides as well as lipoproteins such as low-density lipoprotein (LDL) cholesterol.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month. Doses can be expressed as mg/kg or g/kg.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region can be referred to as a "gap segment" and the external regions can be referred to as "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Glucose" is a monosaccharide used by cells as a source of energy and metabolic intermediate. "Plasma glucose" refers to glucose present in the plasma.

"High density lipoprotein-C (HDL-C)" means cholesterol associated with high density lipoprotein particles. Concentration of HDL-C in serum (or plasma) is typically quantified in mg/dL or nmol/L. "serum HDL-C" and "plasma HDL-C" mean HDL-C in serum and plasma, respectively.

"HMG-CoA reductase inhibitor" means an agent that acts through the inhibition of the enzyme HMG-CoA reductase, such as atorvastatin, rosuvastatin, fluvastatin, lovastatin, pravastatin, and simvastatin.

"Hybridization" means the annealing of complementary nucleic acid molecules. In certain embodiments, complementary nucleic acid molecules include an antisense compound and a target nucleic acid.

"Hypercholesterolemia" means a condition characterized by elevated cholesterol or circulating (plasma) cholesterol, LDL-cholesterol and VLDL-cholesterol, as per the guidelines of the Expert Panel Report of the National Cholesterol Educational Program (NCEP) of Detection, Evaluation of Treatment of high cholesterol in adults (see, Arch. Int. Med. (1988) 148, 36-39).

"Hyperlipidemia" or "hyperlipemia" is a condition characterized by elevated serum lipids or circulating (plasma) lipids. This condition manifests an abnormally high concentration of fats. The lipid fractions in the circulating blood are cholesterol, low density lipoproteins, very low density lipoproteins and triglycerides.

"Hypertriglyceridemia" means a condition characterized by elevated triglyceride levels.

"Identifying" or "selecting a subject having a metabolic or cardiovascular disease" means identifying or selecting a subject having been diagnosed with a metabolic disease, a cardiovascular disease, or a metabolic syndrome; or, identifying or selecting a subject having any symptom of a metabolic disease, cardiovascular disease, or metabolic syndrome including, but not limited to, hypercholesterolemia, hyperglycemia, hyperlipidemia, hypertriglyceridemia, hypertension increased insulin resistance, decreased insulin sensitivity, above normal body weight, and/or above normal body fat content or any combination thereof. Such identification may be accomplished by any method, including but not limited to, standard clinical tests or assessments, such as measuring serum or circulating (plasma) cholesterol, measuring serum or circulating (plasma) blood-glucose, measuring serum or circulating (plasma) triglycerides, measuring blood-pressure, measuring body fat content, measuring body weight, and the like.

"Identifying" or "selecting a diabetic subject" means identifying or selecting a subject having been identified as diabetic or identifying or selecting a subject having any symptom of diabetes (type 1 or type 2) such as, but not limited to, having a fasting glucose of at least 110 mg/dL, glycosuria, polyuria, polydipsia, increased insulin resistance, and/or decreased insulin sensitivity.

"Identifying" or "selecting an obese subject" means identifying or selecting a subject having been diagnosed as obese or identifying or selecting a subject with a BMI over 30 and/or a waist circumference of greater than 102 cm in men or greater than 88 cm in women.

"Identifying" or "selecting a subject having dyslipidemia" means identifying or selecting a subject diagnosed with a disorder of lipid and/or lipoprotein metabolism, including lipid and/or lipoprotein overproduction or deficiency. Dyslipidemias may be manifested by elevation of lipids such as cholesterol and triglycerides as well as lipoproteins such as low-density lipoprotein (LDL) cholesterol.

"Identifying" or "selecting" a subject having increased adiposity" means identifying or selecting a subject having an increased amount of body fat (or adiposity) that includes concern for one or both the distribution of fat throughout the body and the size and mass of the adipose tissue deposits. Body fat distribution can be estimated by skin-fold measures, waist-to-hip circumference ratios, or techniques such as ultrasound, computer tomography, or magnetic resonance imaging. According to the Center for Disease Control and Prevention, individuals with a body mass index (BMI) of 30 or more are considered obese.

"Improved cardiovascular outcome" means a reduction in the occurrence of adverse cardiovascular events, or the risk thereof. Examples of adverse cardiovascular events include, without limitation, death, reinfarction, stroke, cardiogenic shock, pulmonary edema, cardiac arrest, and atrial dysrhythmia.

"Immediately adjacent" means there are no intervening elements between the immediately adjacent elements.

"Individual" or "subject" or "animal" means a human or non-human animal selected for treatment or therapy.

"Inhibiting the expression or activity" refers to a reduction or blockade of the expression or activity and does not necessarily indicate a total elimination of expression or activity.

"Insulin resistance" is defined as the condition in which normal amounts of insulin are inadequate to produce a normal insulin response from cells, e.g., fat, muscle and/or liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

"Insulin sensitivity" is a measure of how effectively an individual processes glucose. An individual having high insulin sensitivity effectively processes glucose whereas an individual with low insulin sensitivity does not effectively process glucose.

"Internucleoside linkage" refers to the chemical bond between nucleosides.

"Intravenous administration" means administration into a vein.

"Linked nucleosides" means adjacent nucleosides which are bonded together.

"Lipid-lowering" means a reduction in one or more lipids in a subject. Lipid-lowering can occur with one or more doses over time.

"Lipid-lowering agent" means an agent, for example, an ANGPTL3-specific modulator, provided to a subject to achieve a lowering of lipids in the subject. For example, in certain embodiments, a lipid-lowering agent is provided to a subject to reduce one or more of apoB, apoC3, total cholesterol, LDL-C, VLDL-C, IDL-C, non-HDL-C, triglycerides, small dense LDL particles, and Lp(a) in a subject. "Lipid-lowering therapy" means a therapeutic regimen provided to a subject to reduce one or more lipids in a subject. In certain embodiments, a lipid-lowering therapy is provided to reduce one or more of apoB, apoC-III, total cholesterol, LDL-C, VLDL-C, IDL-C, non-HDL-C, triglycerides, small dense LDL particles, and Lp(a) in a subject.

"Lipoprotein", such as VLDL, LDL and HDL, refers to a group of proteins found in the serum, plasma and lymph and are important for lipid transport. The chemical composition of each lipoprotein differs in that the HDL has a higher proportion of protein versus lipid, whereas the VLDL has a lower proportion of protein versus lipid.

"Low density lipoprotein-cholesterol (LDL-C)" means cholesterol carried in low density lipoprotein particles. Concentration of LDL-C in serum (or plasma) is typically quantified in mg/dL or nmol/L. "Serum LDL-C" and "plasma LDL-C" mean LDL-C in the serum and plasma, respectively.

"Major risk factors" refers to factors that contribute to a high risk for a particular disease or condition. In certain embodiments, major risk factors for coronary heart disease include, without limitation, cigarette smoking, hypertension, low HDL-C, family history of coronary heart disease, age, and other factors disclosed herein.

"Metabolic disorder" or "metabolic disease" refers to a condition characterized by an alteration or disturbance in metabolic function. "Metabolic" and "metabolism" are terms well known in the art and generally include the whole range of biochemical processes that occur within a living organism. Metabolic disorders include, but are not limited to, hyperglycemia, prediabetes, diabetes (type I and type 2), obesity, insulin resistance, metabolic syndrome and dyslipidemia due to type 2 diabetes.

"Metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Mismatch" or "non-complementary nucleobase" refers to the case when a nucleobase of a first nucleic acid is not capable of pairing with the corresponding nucleobase of a second or target nucleic acid.

"Mixed dyslipidemia" means a condition characterized by elevated cholesterol and elevated triglycerides.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleoside" means a nucleoside having, independently, one or more modified sugar moiety or modified nucleobase.

"Modified nucleotide" means a nucleotide having, independently, one or more modified sugar moiety, modified internucleoside linkage, or modified nucleobase. A "modified nucleoside" means a nucleoside having, independently, one or more modified sugar moiety or modified nucleobase.

"Modified oligonucleotide" means an oligonucleotide comprising at least one modified nucleotide.

"Modified sugar" refers to a substitution or change from a natural sugar.

"Motif" means the pattern of chemically distinct regions in an antisense compound.

"MTP inhibitor" means an agent inhibits the enzyme microsomal triglyceride transfer protein.

"Naturally occurring internucleoside linkage" means a 3' to 5' phosphodiester linkage.

"Natural sugar moiety" means a sugar found in DNA (2'-H) or RNA (2'-OH).

"Non-alcoholic fatty liver disease" or "NAFLD" means a condition characterized by fatty inflammation of the liver that is not due to excessive alcohol use (for example, alcohol consumption of over 20 g/day). In certain embodiments, NAFLD is related to insulin resistance and metabolic syndrome. NAFLD encompasses a disease spectrum ranging from simple triglyceride accumulation in hepatocytes (hepatic steatosis) to hepatic steatosis with inflammation (steatohepatitis), fibrosis, and cirrhosis.

"Nonalcoholic steatohepatitis" (NASH) occurs from progression of NAFLD beyond deposition of triglycerides. A "second hit" capable of inducing necrosis, inflammation, and fibrosis is required for development of NASH. Candidates for the second-hit can be grouped into broad categories: factors causing an increase in oxidative stress and factors promoting expression of proinflammatory cytokines. It has been suggested that increased liver triglycerides lead to increased oxidative stress in hepatocytes of animals and humans, indicating a potential cause-and-effect relationship between hepatic triglyceride accumulation, oxidative stress, and the progression of hepatic steatosis to NASH (Browning and Horton, *J Clin Invest*, 2004, 114, 147-152). Hypertriglyceridemia and hyperfattyacidemia can cause triglyceride accumulation in peripheral tissues (Shimamura et al., *Biochem Biophys Res Commun*, 2004, 322, 1080-1085).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA). A nucleic acid can also comprise a combination of these elements in a single molecule.

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics e.g. non furanose sugar units.

"Nucleotide" means a nucleoside having a phosphate group covalently linked to the sugar portion of the nucleoside.

"Nucleotide mimetic" includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

"Oligomeric compound" or "oligomer" refers to a polymeric structure comprising two or more sub-structures and capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

"Oligonucleotide" means a polymer of linked nucleosides each of which can be modified or unmodified, independent one from another.

"Parenteral administration" means administration by a manner other than through the digestive tract. Parenteral administration includes topical administration, subcutaneous administration, intravenous administration, intramuscular administration, intraarterial administration, intraperitoneal administration, or intracranial administration, e.g. intrathecal or intracerebroventricular administration. Administration can be continuous, or chronic, or short or intermittent.

"Peptide" means a molecule formed by linking at least two amino acids by amide bonds. Peptide refers to polypeptides and proteins.

"Pharmaceutical agent" means a substance that provides a therapeutic benefit when administered to an individual. For example, in certain embodiments, an antisense oligonucleotide targeted to ANGPTL3 is pharmaceutical agent.

"Pharmaceutical composition" means a mixture of substances suitable for administering to an individual. For example, a pharmaceutical composition can comprise one or more active agents and a sterile aqueous solution.

"Pharmaceutically acceptable carrier" means a medium or diluent that does not interfere with the structure or function of the oligonucleotide. Certain, of such carries enable pharmaceutical compositions to be formulated as, for example, tablets, pills, dragees, capsules, liquids, gels, syrups, slurries, suspension and lozenges for the oral ingestion by a subject. Certain of such carriers enable pharmaceutical compositions to be formulated for injection or infusion. For example, a pharmaceutically acceptable carrier can be a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum can indicate liver toxicity or liver function abnormality. For example, increased bilirubin can indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity with a target nucleic acid to induce a desired effect, while exhibiting minimal or no effects on non-target nucleic acids under conditions in which specific binding is desired, i.e. under physiological conditions in the case of in vivo assays and therapeutic treatments.

"Statin" means an agent that inhibits the activity of HMG-CoA reductase.

"Subcutaneous administration" means administration just below the skin.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target region" is defined as a portion of the target nucleic acid having at least one identifiable structure, function, or characteristic.

"Target segment" means the sequence of nucleotides of a target nucleic acid to which one or more antisense compound is targeted. "5' target site" refers to the 5'-most nucleotide of a target segment. "3' target site" refers to the 3'-most nucleotide of a target segment.

"Therapeutically effective amount" means an amount of an agent that provides a therapeutic benefit to an individual.

"Therapeutic lifestyle change" means dietary and lifestyle changes intended to lower fat/adipose tissue mass and/or cholesterol. Such change can reduce the risk of developing heart disease, and may include recommendations for dietary intake of total daily calories, total fat, saturated fat, polyunsaturated fat, monounsaturated fat, carbohydrate, protein, cholesterol, insoluble fiber, as well as recommendations for physical activity.

"Triglyceride" means a lipid or neutral fat consisting of glycerol combined with three fatty acid molecules.

"Type 2 diabetes," (also known as "type 2 diabetes mellitus" or "diabetes mellitus, type 2", and formerly called "diabetes mellitus type 2", "non-insulin-dependent diabetes (NIDDM)", "obesity related diabetes", or "adult-onset diabetes") is a metabolic disorder that is primarily characterized by insulin resistance, relative insulin deficiency, and hyperglycemia.

"Treat" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is a RNA nucleotide (i.e. β-D-ribonucleosides) or a DNA nucleotide (i.e. β-D-deoxyribonucleoside).

Certain Embodiments

In certain embodiments, the compounds or compositions of the invention comprise a modified oligonucleotide 10 to 30 linked nucleosides in length targeted to ANGPTL3. The ANGPTL target can have a sequence selected from any one of SEQ ID NOs: 1-5.

In certain embodiments, the compounds or compositions of the invention comprise a modified oligonucleotide consisting of 10 to 30 nucleosides having a nucleobase sequence comprising at least 8 contiguous nucleobases complementary to an equal length portion of SEQ ID NOs: 1-5.

In certain embodiments, the compounds or compositions of the invention comprise a modified oligonucleotide consisting of 10 to 30 nucleosides having a nucleobase sequence comprising at least 8 contiguous nucleobases of a nucleobase sequence selected from any of SEQ ID NO: 34-182.

In certain embodiments, the compounds or compositions of the invention comprise a modified oligonucleotide consisting of 10 to 30 linked nucleosides and having a nucleobase sequence comprising at least 8, 9, 10, 11, 12, 13, 14, 15, 16, 17, 18, 19 or 20 contiguous nucleobases of a nucleobase sequence selected from a sequence recited in any one of SEQ ID NOs: 34-182.

In certain embodiments, the compounds or compositions of the invention comprise a salt of the modified oligonucleotide.

In certain embodiments, the compounds or compositions of the invention further comprise a pharmaceutically acceptable carrier or diluent.

In certain embodiments, the nucleobase sequence of the modified oligonucleotide is at least 70%, 80%, 90%, 95% or 100% complementary to any one of SEQ ID NO: 1-5 as measured over the entirety of the modified oligonucleotide.

In certain embodiments, the compound of the invention consists of a single-stranded modified oligonucleotide.

In certain embodiments, the modified oligonucleotide consists of 8, 9, 10, 11, 12, 13, 14, 15, 16, 17, 18, 19, 20, 21, 22, 23, 24, 25, 26, 27, 28, 29 or 30 linked nucleosides. In certain embodiments, the modified oligonucleotide consists of 20 linked nucleosides.

In certain embodiments, at least one internucleoside linkage of said modified oligonucleotide is a modified internucleoside linkage. In certain embodiments, each internucleoside linkage is a phosphorothioate internucleoside linkage.

In certain embodiments, at least one nucleoside of the modified oligonucleotide comprises a modified sugar. In certain embodiments the modified oligonucleotide comprises at least one tetrahydropyran modified nucleoside wherein a tetrahydropyran ring replaces a furanose ring. In certain embodiments each of the tetrahydropyran modified nucleoside has the structure:

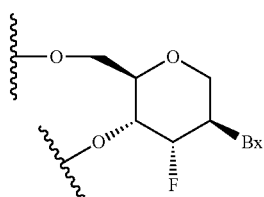

wherein Bx is an optionally protected heterocyclic base moiety. In certain embodiments, at least one modified sugar is a bicyclic sugar. In certain embodiments, at least one modified sugar comprises a 2'-O-methoxyethyl or a 4'-(CH$_2$)$_n$—O-2' bridge, wherein n is 1 or 2.

In certain embodiments, at least one nucleoside of said modified oligonucleotide comprises a modified nucleobase. In certain embodiments, the modified nucleobase is a 5-methylcytosine.

In certain embodiments, the modified oligonucleotide comprises: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar. In certain embodiments, the modified oligonucleotide consists of 20 linked nucleosides, the gap segment consisting often linked deoxynucleosides, the 5' wing segment consisting of five linked nucleosides, the 3' wing segment consisting of five linked nucleosides, each nucleoside of each wing segment comprises a 2'-O-methoxyethyl sugar and each internucleoside linkage is a phosphorothioate linkage.

In certain embodiments, the compounds or compositions of the invention comprise a modified oligonucleotide consisting of 20 linked nucleosides having a nucleobase sequence comprising at least 8 contiguous nucleobases complementary to an equal length portion of SEQ ID NO: 1-5, wherein the modified oligonucleotide comprises: a) a gap segment consisting often linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

In certain embodiments, the compounds or compositions of the invention comprise a modified oligonucleotide consisting of 20 linked nucleosides having a nucleobase sequence comprising at least 8 contiguous nucleobases of a nucleobase sequence selected from any of SEQ ID NO: 34-182, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

Certain embodiments provide methods, compounds, and compositions for inhibiting ANGPTL3 expression.

Certain embodiments provide a method of reducing ANGPTL3 expression in an animal comprising administering to the animal a compound comprising a modified oligonucleotide 10 to 30 linked nucleosides in length targeted to ANGPTL3.

Certain embodiments provide a method of reducing ApoC-III expression in an animal comprising administering to the animal a compound comprising a modified oligonucleotide 10 to 30 linked nucleosides in length targeted to ANGPTL3, thereby reducing the expression of ApoC-III in the animal.

Certain embodiments provide a method of reducing triglyceride levels in an animal comprising administering to the animal a compound comprising a modified oligonucleotide 10 to 30 linked nucleosides in length targeted to ANGPTL3, thereby reducing the level of triglyceride in the animal.

Certain embodiments provide a method of reducing cholesterol levels in an animal comprising administering to the animal a compound comprising a modified oligonucleotide 10 to 30 linked nucleosides in length targeted to ANGPTL3, thereby reducing the level of cholesterol in the animal.

Certain embodiments provide a method of reducing low-density lipoprotein (LDL) levels in an animal comprising administering to the animal a compound comprising a modified oligonucleotide 10 to 30 linked nucleosides in length targeted to ANGPTL3, thereby reducing the level of low-density lipoprotein (LDL) in the animal.

Certain embodiments provide a method of reducing glucose levels in an animal comprising administering to the animal a compound comprising a modified oligonucleotide 10 to 30 linked nucleosides in length targeted to ANGPTL3, thereby reducing the level of glucose in the animal.

Certain embodiments provide a method of ameliorating metabolic or cardiovascular disease in an animal comprising administering to the animal a compound comprising a modified oligonucleotide 10 to 30 linked nucleosides in length targeted to ANGPTL3, thereby ameliorating the metabolic or cardiovascular disease in the animal.

Certain embodiments provide a method for treating an animal with an ANGPTL3 related disease or condition comprising: a) identifying said animal with the ANGPTL3 related disease or conditon, and b) administering to said animal a therapeutically effective amount of a compound comprising a modified oligonucleotide 10 to 30 linked nucleosides in length targeted to ANGPTL3. In certain embodiments, the therapeutically effective amount of the compound administered to the animal reduces the ANGPTL3 related disease or conditon in the animal.

Certain embodiments provide a method for treating an animal with metabolic or cardiovascular disease comprising: a) identifying said animal with metabolic or cardiovascular disease, and b) administering to said animal a therapeutically effective amount of a compound comprising a modified oligonucleotide consisting of 20 linked nucleosides and having a nucleobase sequence at least 90% complementary to SEQ ID NO: 1-5 as measured over the entirety of said modified oligonucleotide, thereby treating the animal with metabolic or cardiovascular disease. In certain embodiments, the therapeutically effective amount of the compound administered to the animal reduces the metabolic or cardiovascular disease in the animal.

Certain embodiments provide a method of decreasing one or more of ANGPTL3 levels, LDL levels, apoC-III levels, triglyceride levels, cholesterol levels, glucose levels, fat pad weight, cardiovascular disease and metabolic disease in a human by administering an ANGPTL3 inhibitor comprising a modified oligonucleotide consisting of 20 linked nucleosides and having a nucleobase sequence at least 90% complementary to SEQ ID NO: 1-5 as measured over the entirety of said modified oligonucleotide.

Certain embodiments provide uses of the compounds and compositions described herein for inhibiting ANGPTL3 expression.

Certain embodiments provide use of the compounds and compositions described herein for reducing ANGPTL3 expression in an animal. Certain embodiments include administering to the animal a compound comprising a modified oligonucleotide 10 to 30 linked nucleosides in length targeted to ANGPTL3.

Certain embodiments provide use of the compounds and compositions described herein for reducing ApoC-III expression in an animal. Certain embodiments include administering to the animal a compound comprising a modified oligonucleotide 10 to 30 linked nucleosides in length targeted to ANGPTL3, thereby reducing the expression of ApoC-III in the animal.

Certain embodiments provide use of the compounds and compositions described herein for reducing triglyceride levels in an animal. Certain embodiments include administering to the animal a compound comprising a modified oligonucleotide 10 to 30 linked nucleosides in length targeted to ANGPTL3, thereby reducing the level of triglyceride in the animal.

Certain embodiments provide use of the compounds and compositions described herein for reducing cholesterol levels in an animal. Certain embodiments include administering to the animal a compound comprising a modified oligonucleotide 10 to 30 linked nucleosides in length targeted to ANGPTL3, thereby reducing the level of cholesterol in the animal.

Certain embodiments provide use of the compounds and compositions described herein for reducing low-density lipoprotein (LDL) levels in an animal. Certain embodiments include administering to the animal a compound comprising a modified oligonucleotide 10 to 30 linked nucleosides in length targeted to ANGPTL3, thereby reducing the level of low-density lipoprotein (LDL) in the animal.

Certain embodiments provide use of the compounds and compositions described herein for reducing glucose levels in an animal. Certain embodiments include administering to the animal a compound comprising a modified oligonucleotide 10 to 30 linked nucleosides in length targeted to ANGPTL3, thereby reducing the level of glucose in the animal.

Certain embodiments provide use of the compounds and compositions described herein for ameliorating metabolic or cardiovascular disease in an animal. Certain embodiments include administering to the animal a compound comprising a modified oligonucleotide 10 to 30 linked nucleosides in length targeted to ANGPTL3, thereby ameliorating the metabolic or cardiovascular disease in the animal.

Certain embodiments provide use of the compounds and compositions described herein for treatment. Certain embodiments provide use of the compounds and compositions described herein for treating an animal with an ANGPTL3 related disease or condition. In certan embodiments, the ANGPTL3 related disease or condition is metabolic or cardiovascular disease. Certain embodiments include: a) identifying said animal with the ANGPTL3 related disease or conditon, and b) administering to said animal a therapeutically effective amount of a compound comprising a modified oligonucleotide 10 to 30 linked nucleosides in length targeted to ANGPTL3. In certain embodiments, the therapeutically effective amount of the compound administered to the animal reduces the ANGPTL3 related disease or conditon in the animal.

Certain embodiments provide use of the compounds and compositions described herein for treating an animal with metabolic or cardiovascular disease. comprising: a) identifying said animal with metabolic or cardiovascular disease, and b) administering to said animal a therapeutically effective amount of a compound comprising a modified oligonucleotide consisting of 20 linked nucleosides and having a nucleobase sequence at least 90% complementary to SEQ ID NO: 1-5 as measured over the entirety of said modified oligonucleotide, thereby treating the animal with metabolic or cardiovascular disease. In certain embodiments, the therapeutically effective amount of the compound administered to the animal reduces the metabolic or cardiovascular disease in the animal.

Certain embodiments provide use of the compounds and compositions described herein for decreasing one or more of ANGPTL3 levels, LDL levels, apoC-III levels, triglyceride levels, cholesterol levels, glucose levels, fat pad weight, cardiovascular disease and metabolic disease in a human by administering an ANGPTL3 inhibitor comprising a modified oligonucleotide consisting of 20 linked nucleosides and having a nucleobase sequence at least 90% complementary to SEQ ID NO: 1-5 as measured over the entirety of said modified oligonucleotide.

In certain embodiments, ANGPTL3 has the sequence as set forth in GenBank Accession No. BG400407.1 (incorporated herein as SEQ ID NO: 1). In certain embodiments, ANGPTL3 has the sequence as set forth in GenBank Accession No. BG562555.1 (incorporated herein as SEQ ID NO: 2). In certain embodiments, ANGPTL3 has the sequence as set forth in GenBank Accession No. BG562798.1 (incorporated herein as SEQ ID NO: 3). In certain embodiments, ANGPTL3 has the sequence as set forth in GenBank Accession No. NM_014495.1 (incorporated herein as SEQ ID NO: 4). In certain embodiments, ANGPTL3 has the sequence as set forth in GenBank Accession No. NT_032977.5 nucleotides 15511702 to 15521082 (incorporated herein as SEQ ID NO: 5). In certain embodiments, ANGPTL3 has the sequence as set forth in GenBank Accession No. AF162224.1 (incorporated herein as SEQ ID NO: 6). In certain embodiments, ANGPTL3 has the sequence as set forth in GenBank Accession No. AI195524.1 (incorporated herein as SEQ ID NO: 7). In certain embodiments, ANGPTL3 has the sequence as set forth in GenBank Accession No. BB717501.1 (incorporated herein as SEQ ID NO: 8).

TABLE 1

Gene Target Names and Sequences

| Target Name | Species | Genbank # | SEQ ID NO |
|---|---|---|---|
| angiopoietin-like 3 | Human | BG400407.1 | 1 |
| angiopoietin-like 3 | Human | BG562555.1 | 2 |
| angiopoietin-like 3 | Human | BG562798.1 | 3 |
| angiopoietin-like 3 | Human | NM_014495.1 | 4 |
| angiopoietin-like 3 | Human | nucleotides 15511702 to 15521082 of NT_032977.5 | 5 |
| angiopoietin-like 3 | Mouse | AF162224.1 | 6 |
| angiopoietin-like 3 | Mouse | AI195524.1 | 7 |
| angiopoietin-like 3 | Mouse | BB717501.1 | 8 |

In certain embodiments, the animal is a human.

In certain embodiments, the compounds or compositions of the invention are designated as a first agent and the methods or uses of the invention further comprise administering a second agent. In certain embodiments, the first agent and the second agent are co-administered. In certain embodiments the first agent and the second agent are co-administered sequentially or concomitantly.

In certain embodiments, the second agent is a glucose-lowering agent. The glucose lowering agent can include, but is not limited to, a therapeutic lifestyle change, PPAR agonist, a dipeptidyl peptidase (IV) inhibitor, a GLP-1 analog, insulin or an insulin analog, an insulin secretagogue, a SGLT2 inhibitor, a human amylin analog, a biguanide, an alpha-glucosidase inhibitor, or a combination thereof. The glucose-lowering agent can include, but is not limited to metformin, sulfonylurea, rosiglitazone, meglitinide, thiazolidinedione, alpha-glucosidase inhibitor or a combination thereof. The sulfonylurea can be acetohexamide, chlorpropamide, tolbutamide, tolazamide, glimepiride, a glipizide, a glyburide, or a gliclazide. The meglitinide can be nateglinide or repaglinide. The thiazolidinedione can be pioglitazone or rosiglitazone. The alpha-glucosidase can be acarbose or miglitol.

In certain embodiments, the second agent is a lipid-lowering therapy. In certain embodiments the lipid lowering therapy can include, but is not limited to, a therapeutic lifestyle change, HMG-CoA reductase inhibitor, cholesterol absorption inhibitor, MTP inhibitor, antisense compound targeted to ApoB or any combination thereof. The HMG-CoA reductase inhibitor can be atorvastatin, rosuvastatin, fluvastatin, lovastatin, pravastatin, or simvastatin. The cholesterol absorption inhibitor can be ezetimibe.

In certain embodiments, administration comprises parenteral administration.

In certain embodiments, the metabolic or cardiovascular disease includes, but is not limited to, obesity, diabetes, atherosclerosis, dyslipidemia, coronary heart disease, non-alcoholic fatty liver disease (NAFLD), hyperfattyacidemia or metabolic syndrome, or a combination thereof. The dyslipidemia can be hyperlipidemia. The hyperlipidemia can be hypercholesterolemia, hypertriglyceridemia, or both hypercholesterolemia and hypertriglyceridemia. The NAFLD can be hepatic steatosis or steatohepatitis. The diabetes can be type 2 diabetes or type 2 diabetes with dyslipidemia.

In certain embodiments, administering the compound of the invention results in a reduction of lipid levels, including triglyceride levels, cholesterol levels, insulin resistance, glucose levels or a combination thereof. One or more of the levels can be independently reduced by 5%, 10%, 20%, 30%, 35%, or 40%. Administering the compound of the invention can result in improved insulin sensitivity or hepatic insulin sensitivity. Administering the compound of the invention can result in a reduction in atherosclerotic plaques, obesity, glucose, lipids, glucose resistance, cholesterol, or improvement in insulin sensitivity or any combination thereof.

Certain embodiments provide the use of a compound as described herein in the manufacture of a medicament for treating, ameliorating, delaying or preventing one or more of a metabolic disease or a cardiovascular disease.

Certain embodiments provide a kit for treating, preventing, or ameliorating one or more of a metabolic disease or a cardiovascular disease as described herein wherein the kit comprises: a) a compound as described herein; and optionally b) an additional agent or therapy as described herein. The kit can further include instructions or a label for using the kit to treat, prevent, or ameliorate one or more of a metabolic disease or a cardiovascular disease.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound can be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to ANGPTL3 nucleic acid is 10 to 30 nucleotides in length. In other words, antisense compounds are from 10 to 30 linked nucleobases. In other embodiments, the antisense compound comprises a modified oligonucleotide consisting of 8 to 80, 10-80, 12 to 50, 15 to 30, 18 to 24, 19 to 22, or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values.

In certain embodiments, the antisense compound comprises a shortened or truncated modified oligonucleotide. The shortened or truncated modified oligonucleotide can have a single nucleoside deleted from the 5' end (5' truncation), or alternatively from the 3' end (3' truncation). A shortened or truncated oligonucleotide can have two or more nucleosides deleted from the 5' end, or alternatively can have two or more nucleosides deleted from the 3' end. Alternatively, the deleted nucleosides can be dispersed throughout the modified oligonucleotide, for example, in an antisense compound having one or more nucleoside deleted from the 5' end and one or more nucleoside deleted from the 3' end.

When a single additional nucleoside is present in a lengthened oligonucleotide, the additional nucleoside can be located at the 5', 3' end or central portion of the oligonucleotide. When two or more additional nucleosides are present, the added nucleosides can be adjacent to each other, for example, in an oligonucleotide having two nucleosides added to the 5' end (5' addition), or alternatively to the 3' end (3' addition) or the central portion, of the oligonucleotide. Alternatively, the added nucleoside can be dispersed throughout the antisense compound, for example, in an oligonucleotide having one or more nucleoside added to the 5' end, one or more nucleoside added to the 3' end, and/or one or more nucleoside added to the central portion.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to an ANGPTL3 nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound can optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer can in some embodiments include β-D-ribonucleosides, β-D-deoxyribonucleosides, 2'-modified nucleosides (such 2'-modified nucleosides can include 2'-MOE, and 2'-O—CH$_3$, among others), and bicyclic sugar modified nucleosides (such bicyclic sugar modified nucleosides can include those having a 4'-(CH2)n-O-2' bridge, where n=1 or n=2). Preferably, each distinct region comprises uniform sugar moieties. The wing-gap-wing motif is frequently described as "X—Y—Z", where "X" represents the length of the 5' wing region, "Y" represents the length of the gap region, and "Z" represents the length of the 3' wing region. As used herein, a gapmer described as "X—Y—Z" has a configuration such that the gap segment is positioned immediately adjacent each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more nucleotides. Thus, gapmers include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 6-8-6, 5-8-5, 1-8-1, 2-6-2, 6-8-6, 5-8-5, 1-8-1, 2-6-2, 2-13-2, 1-8-2, 2-8-3, 3-10-2, 1-18-2, or 2-18-2.

In certain embodiments, the antisense compound as a "wingmer" motif, having a wing-gap or gap-wing configuration, i.e. an X—Y or Y—Z configuration as described above for the gapmer configuration. Thus, wingmer configurations include, but are not limited to, for example 5-10, 8-4, 4-12, 12-4, 3-14, 16-2, 18-1, 10-3, 2-10, 1-10, 8-2, 2-13, or 5-13.

In certain embodiments, antisense compounds targeted to an ANGPTL3 nucleic acid possess a 5-10-5 gapmer motif.

In certain embodiments, an antisense compound targeted to an ANGPTL3 nucleic acid has a gap-widened motif.

Target Nucleic Acids, Target Regions and Nucleotide Sequences

Nucleotide sequences that encode ANGPTL3 include, without limitation, the following: the human sequence as set forth in GenBank Accession No. BG400407.1 (incorporated herein as SEQ ID NO: 1), GenBank Accession No. BG562555.1 (incorporated herein as SEQ ID NO: 2), GenBank Accession No. BG562798.1 (incorporated herein as SEQ ID NO: 3), GenBank Accession No. NM_014495.1 (incorporated herein as SEQ ID NO: 4), GenBank Accession No. NT_032977.5 nucleotides 15511702 to 15521082 (incorporated herein as SEQ ID NO: 5), GenBank Accession No. AF162224.1 (incorporated herein as SEQ ID NO: 6), GenBank Accession No. AI195524.1 (incorporated herein as SEQ ID NO: 7) and GenBank Accession No. BB717501.1 (incorporated herein as SEQ ID NO: 8). It is understood that the sequence set forth in each SEQ ID NO in the Examples contained herein is independent of any modification to a sugar moiety, an internucleoside linkage, or a nucleobase. As such, antisense compounds defined by a SEQ ID NO can comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region can encompass a 3' UTR, a 5' UTR, an exon, an intron, an exon/intron junction, a coding region, a translation initiation region, translation termination region, or other defined nucleic acid region. The structurally defined regions for ANGPTL3 can be obtained by accession number from sequence databases such as NCBI and such information is incorporated herein by reference. In certain embodiments, a target region can encompass the sequence from a 5' target site of one target segment within the target region to a 3' target site of another target segment within the target region.

In certain embodiments, a "target segment" is a smaller, sub-portion of a target region within a nucleic acid. For example, a target segment can be the sequence of nucleotides of a target nucleic acid to which one or more antisense compound is targeted. "5' target site" refers to the 5'-most nucleotide of a target segment. "3' target site" refers to the 3'-most nucleotide of a target segment.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region can contain one or more target segments. Multiple target segments within a target region can be overlapping. Alternatively, they can be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments can be found within a 5' UTR, a coding region, a 3' UTR, an intron, an exon, or an exon/intron junction. Target segments containing a start codon or a stop codon are also suitable target segments. A suitable target segment can specifically exclude a certain structurally defined region such as the start codon or stop codon.

The determination of suitable target segments can include a comparison of the sequence of a target nucleic acid to other sequences throughout the genome. For example, the BLAST algorithm can be used to identify regions of similarity amongst different nucleic acids. This comparison can prevent the selection of antisense compound sequences that can hybridize in a non-specific manner to sequences other than a selected target nucleic acid (i.e., non-target or off-target sequences).

There can be variation in activity (e.g., as defined by percent reduction of target nucleic acid levels) of the antisense compounds within an active target region. In certain embodiments, reductions in ANGPTL3 mRNA levels are indicative of inhibition of ANGPTL3 protein expression. Reductions in levels of an ANGPTL3 protein are also indicative of inhibition of target mRNA expression. Further, phenotypic changes, such as a reduction of the level of cholesterol, LDL, triglyceride, or glucose, can be indicative of inhibition of ANGPTL3 mRNA and/or protein expression.

Hybridization

In some embodiments, hybridization occurs between an antisense compound disclosed herein and a ANGPTL3 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art (Sambrooke and Russell, Molecular Cloning: A Laboratory Manual, $3^{rd}$ Ed., 2001). In certain embodiments, the antisense compounds provided herein are specifically hybridizable with an ANGPTL3 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an ANGPTL3 nucleic acid).

An antisense compound can hybridize over one or more segments of an ANGPTL3 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 75%, 80%, 85%, 86%, 87%, 88%, 89%, 90%, 91%, 92%, 93%, 94%, 95%, 96%, 97%, 98%, 99%, or 100% complementary to an ANGPTL3 nucleic acid, a target region, target segment, or specified portion thereof. In certain embodiments, the antisense compounds provided herein, or a specified portion thereof, are, or are at least, 70%, 75%, 80%, 85%, 86%, 87%, 88%, 89%, 90%, 91%, 92%, 93%, 94%, 95%, 96%, 97%, 98%, 99%, or 100% complementary to the sequence of one or more of SEQ ID NOs: 1-5. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases can be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound can be fully complementary to an ANGPTL3 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound can be fully complementary to the target sequence, depending on whether the remaining 10 nucleobases of the antisense compound are also complementary to the target sequence.

The location of a non-complementary nucleobase can be at the 5' end or 3' end of the antisense compound. Alternatively, the non-complementary nucleobase or nucleobases can be at an internal position of the antisense compound. When two or more non-complementary nucleobases are present, they can be either contiguous (i.e. linked) or non-contiguous. In one embodiment, a non-complementary nucleobase is located in the wing segment of a gapmer antisense oligonucleotide.

In certain embodiments, antisense compounds that are, or are up to 10, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an ANGPTL3 nucleic acid, or specified portion thereof.

In certain embodiments, antisense compounds that are, or are up to 10, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an ANGPTL3 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 10 nucleobase portion of a target segment. In certain embodiments, the antisense compounds are complementary to at least a 15 nucleobase portion of a target segment. Also contemplated are antisense compounds that are complementary to at least an 8, 9, 10, 11, 12, 13, 14, 15, 16, 17, 18, 19, 20, or more nucleobase portion of a target segment, or a range defined by any two of these values.

Identity

The antisense compounds provided herein can also have a defined percent identity to a particular nucleotide sequence, SEQ ID NO, or the sequence of a compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases can be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides can also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an ANGPTL3 nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides can impart enhanced nuclease stability, increased binding affinity or some other beneficial biological property to the antisense compounds. In certain embodiments, nucleosides comprise a chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R1)(R)2$ (R=H, C1-C12 alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH3 and 2'-O(CH2)2OCH3 substituent groups. The substituent at the 2' position can also be selected from allyl, amino, azido, thio, O-allyl, O—C1-C10 alkyl, OCF3, O(CH2)2SCH3, O(CH2)2-O—N(Rm)(Rn), and O—CH2-C(=O)—N(Rm)(Rn), where each Rm and Rn is, independently, H or substituted or unsubstituted C1-C10 alkyl.

Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-(CH2)-O-2' (LNA); 4'-(CH2)-S-2; 4'-(CH2)2-O-2' (ENA); 4'-C(CH3)2-O-2' (see PCT/US2008/068922); 4'-CH(CH3)¬-O-2' and 4'-C¬H(CH2OCH3)¬-O-2' (see U.S. Pat. No. 7,399,845, issued on Jul. 15, 2008); 4'-CH2-N(OCH3)-2' (see PCT/US2008/064591); 4'-CH2-O—N(CH3)-2' (see published U.S. Patent Application US2004-0171570, published Sep. 2, 2004); 4'-CH2-N(R)—O-2' (see U.S. Pat. No. 7,427,672, issued on Sep. 23, 2008); 4'-CH2-CH (see Chattopadhyaya et al., *J. Org. Chem*, 2009, 74, 118-134) (CH3)-2' and 4'-CH2-C¬ (═CH2)-2' (see PCT/US2008/066154); and wherein R is, independently, H, C1-C12 alkyl, or a protecting group. Each of the foregoing BNAs include various stereochemical sugar configurations including for example α-L-ribofuranose and β-D-ribofuranose (see PCT international application PCT/DK98/00393, published on Mar. 25, 1999 as WO 99/14226). Previously, α-L-methyleneoxy (4'-CH$_2$-O-2') BNA's have also been incorporated into antisense oligonucleotides that showed antisense activity (Frieden et al., *Nucleic Acids Research*, 2003, 21, 6365-6372).

Further reports related to bicyclic nucleosides can be found in published literature (see for example: Srivastava et al., *J. Am. Chem. Soc.*, 2007, 129, 8362-8379; U.S. Pat. Nos. 7,053, 207; 6,268,490; 6,770,748; 6,794,499; 7,034,133; and 6,525, 191; Elayadi et al., *Curr. Opinion Invens. Drugs*, 2001, 2, 558-561; Braasch et al., *Chem. Biol.*, 2001, 8, 1-7; and Orum et al., *Curr. Opinion Mol. Ther.*, 2001, 3, 239-243; and U.S. Pat. No. 6,670,461; International applications WO 2004/106356; WO 94/14226; WO 2005/021570; U.S. Patent Publication Nos. US2004-0171570; US2007-0287831; US2008-0039618; U.S. Pat. No. 7,399,845; U.S. patent Ser. Nos. 12/129,154; 60/989,574; 61/026,995; 61/026,998; 61/056, 564; 61/086,231; 61/097,787; 61/099,844; PCT International Applications Nos. PCT/US2008/064591; PCT/US2008/066154; PCT/US2008/068922; and Published PCT International Applications WO 2007/134181).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C(R$_a$)(R$_b$)]$_n$—, —C(R$_a$)═C(R$_b$)—, —C(R$_a$)═N—, —C(═O)—, —C(═NR$_a$)—, —C(═S)—, —O—, —Si(R$_a$)$_2$—, —S(═O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(═O)—H), substituted acyl, CN, sulfonyl (S(═O)$_2$-J$_1$), or sulfoxyl (S(═O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(═O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is, —[C(R$_a$)(R$_b$)]$_n$—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$-2',4'-(CH$_2$)$_2$-2',4'-(CH$_2$)$_3$-2',4'-CH$_2$—O-2',4'-(CH$_2$)$_2$—O-2', 4'-CH$_2$—O—N(R)-2' and 4'-CH$_2$—N(R)—O-2'- wherein each R is, independently, H, a protecting group or C$_1$-C$_{12}$ alkyl.

In certain embodiments, bicyclic nucleosides include, but are not limited to, (A) α-L-Methyleneoxy (4'-CH$_2$—O-2) BNA, (B) β-D-Methyleneoxy (4'-CH$_2$—O-2) BNA, (C) Ethyleneoxy (4'-(CH$_2$)$_2$—O-2') BNA, (D) Aminooxy (4'-CH$_2$—O—N(R)-2) BNA, (E) Oxyamino (4'-CH$_2$—N(R)—O-2') BNA, and (F) Methyl(methyleneoxy) (4'-CH(CH$_3$)—O-2') BNA, (G) Methylene-thio (4'-CH$_2$—S-2') BNA, (H) Methylene-amino (4'-CH$_2$—N(R)-2') BNA, (I) Methyl carbocyclic (4'-CH$_2$—CH(CH$_3$)-2') BNA, and (J) Propylene carbocyclic (4'-(CH$_2$)$_3$-2') BNA as depicted below.

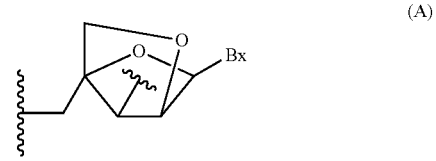

(A)

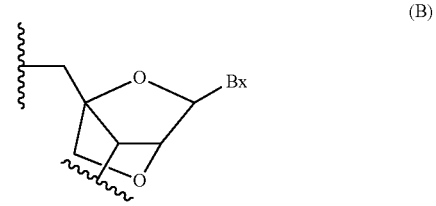

(B)

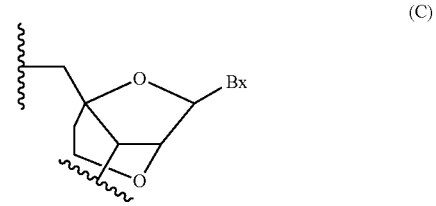

(C)

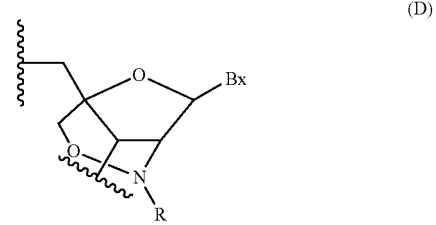

(D)

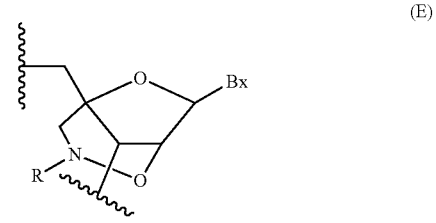

(E)

-continued

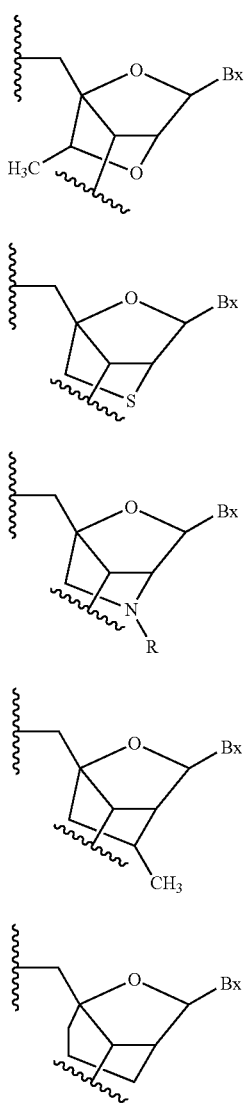

(F)

(G)

(H)

(I)

(J)

wherein Bx is the base moiety and R is independently H, a protecting group or $C_1$-$C_{12}$ alkyl.

In certain embodiments, bicyclic nucleoside having Formula I:

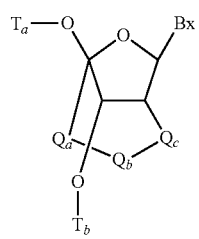

I wherein:
Bx is a heterocyclic base moiety;
-$Q_a$-$Q_b$-$Q_c$- is —$CH_2$—N($R_c$)—$CH_2$—, —C(=O)—N($R_c$)—$CH_2$—, —$CH_2$—O—N($R_c$)—, —$CH_2$—N($R_c$)—O— or —N($R_c$)—O—$CH_2$;
$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleoside having Formula II:

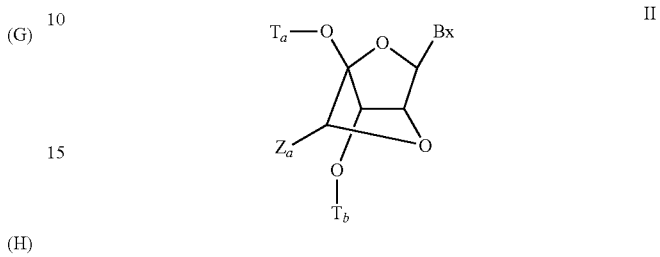

II wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, OC(=X)$J_c$, and $NJ_eC$(=X)$NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleoside having Formula III:

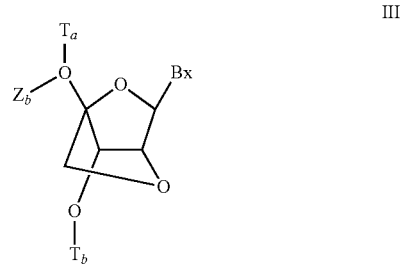

III wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleoside having Formula IV:

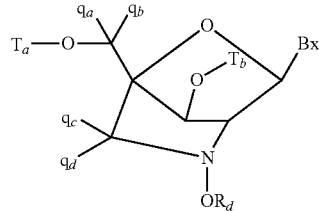

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleoside having Formula V:

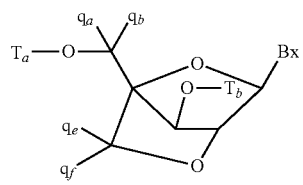

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;
or $q_e$ and $q_f$ together are =C($q_g$)($q_h$);
$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleoside having Formula VI:

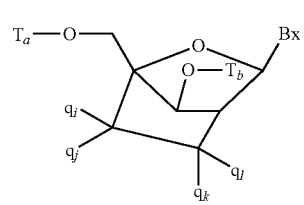

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and
$q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH$_2$)$_3$-2' bridge and the alkenyl analog bridge 4'-CH=CH—CH$_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

In certain embodiments, nucleosides are modified by replacement of the ribosyl ring with a sugar surrogate. Such modification includes without limitation, replacement of the ribosyl ring with a surrogate ring system (sometimes referred to as DNA analogs) such as a morpholino ring, a cyclohexenyl ring, a cyclohexyl ring or a tetrahydropyranyl ring such as one having one of the formula:

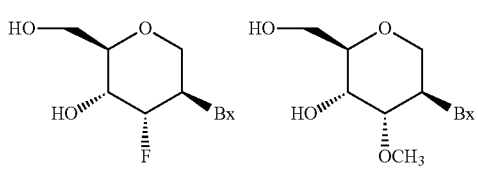

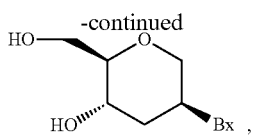

Many other bicyclo and tricyclo sugar surrogate ring systems are also know in the art that can be used to modify nucleosides for incorporation into antisense compounds (see for example review article: Leumann, Christian J., Bioorganic & Medicinal Chemistry, 2002, 10, 841-854). Such ring systems can undergo various additional substitutions to enhance activity. See for example compounds having Formula VII:

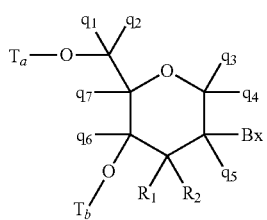

wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, subsituted or unsubstituted alkoxy, $NJ_1J_2$, $SJ_1$, $N_3$, OC(=X)$J_1$, OC(=X)$NJ_1J_2$, $NJ_3$C(=X)$NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H (M). In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro (K). In certain embodiments, THP nucleosides of Formula VII are provided wherein one of $R_1$ and $R_2$ is methoxyethoxy. In certain embodiments, $R_1$ is fluoro and $R_2$ is H; $R_1$ is H and $R_2$ is fluoro; $R_1$ is methoxy and $R_2$ is H, and $R_1$ is H and $R_2$ is methoxyethoxy. Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds targeted to an ANGPTL3 nucleic acid comprise one or more nucleotides having modified sugar moieties. In certain embodiments, the modified sugar moiety is 2'-MOE. In certain embodiments, the 2'-MOE modified nucleotides are arranged in a gapmer motif. In certain embodiments, the modified sugar moiety is a bicyclic nucleoside having a (4'-CH(CH₃)—O-2') bridging group. In certain embodiments, the (4'-CH(CH₃)—O-2') modified nucleotides are arranged throughout the wings of a gapmer motif.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds targeted to an ANGPTL3 nucleic acid comprise one or more nucleotides having modified sugar moieties. In certain embodiments, the modified sugar moiety is 2'-MOE. In certain embodiments, the 2'-MOE modified nucleotides are arranged in a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties can also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to an ANGPTL3 nucleic acid comprise one or more modified nucleobases. In certain embodiments, shortened or gap-widened antisense oligonucleotides targeted to an ANGPTL3 nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides can be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to an ANGPTL3 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to an ANGPTL3 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds can be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acids from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of ANGPTL3 nucleic acids can be tested in vitro in a variety of cell types. Cell types used for such analyses are available from commercial vendors (e.g. American Type Culture Collection, Manassus, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells, Hep3B cells, Huh7 (hepatocellular carcinoma) cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another reagent used to introduce antisense oligonucleotides into cultured cells includes Oligofectamine™ (Invitrogen Life Technologies, Carlsbad, Calif.). Antisense oligonucleotide is mixed with Oligofectamine™ in Opti-MEM™-1 reduced serum medium (Invitrogen Life Technologies, Carlsbad, Calif.) to achieve the desired concentration of oligonucleotide with an Oligofectamine™ to oligonucleotide ratio of approximately 0.2 to 0.8 µL per 100 nM.

Another reagent used to introduce antisense oligonucleotides into cultured cells includes FuGENE 6 (Roche Diagnostics Corp., Indianapolis, Ind.). Antisense oligomeric compound was mixed with FuGENE 6 in 1 mL of serum-free RPMI to achieve the desired concentration of oligonucleotide with a FuGENE 6 to oligomeric compound ratio of 1 to 4 µL of FuGENE 6 per 100 nM.

Another technique used to introduce antisense oligonucleotides into cultured cells includes electroporation (Sambrooke and Russell, Molecular Cloning: A Laboratory Manual, 3$^{rd}$ Ed., 2001).

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE2000®, Lipofectin or Cytofectin. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art (Sambrooke and Russell, Molecular Cloning: A Laboratory Manual, 3$^{rd}$ Ed., 2001). RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of an ANGPTL3 nucleic acid can be assayed in a variety of ways known in the art (Sambrooke and Russell, Molecular Cloning: A Laboratory Manual, 3$^{rd}$ Ed., 2001). For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels can be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, and real-time-PCR reactions are carried out by methods well known to those skilled in the art.

Gene (or RNA) target quantities obtained by real time PCR can be normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invitrogen, Inc. Carlsbad, Calif.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to an ANGPTL3 nucleic acid. Methods for designing real-time PCR probes and primers are well known in the art, and can include the use of software such as PRIMER EXPRESS® Software (Applied Biosystems, Foster City, Calif.).

Gene target quantities obtained by RT, real-time PCR can be normalized using either the expression level of GAPDH, a gene whose expression is constant, or by quantifying total RNA using RiboGreen™ (Molecular Probes, Inc. Eugene, Oreg.). GAPDH expression was quantified by RT, real-time PCR, by being run simultaneously with the target, multiplexing, or separately. Total RNA was quantified using RiboGreen™ RNA quantification reagent (Molecular Probes, Inc. Eugene, Oreg.).

Presented in Table 2 are primers and probes used to measure GAPDH expression in the cell types described herein. The GAPDH PCR probes have JOE covalently linked to the 5' end and TAMRA or MGB covalently linked to the 3' end, where JOE is the fluorescent reporter dye and TAMRA or MGB is the quencher dye. In some cell types, primers and probe designed to a GAPDH sequence from a different species are used to measure GAPDH expression. For example, a human GAPDH primer and probe set is used to measure GAPDH expression in monkey-derived cells and cell lines.

TABLE 2

GAPDH primers and probes for use in real-time PCR

| Target Name | Species | Sequence Description | Sequence (5' to 3') | SEQ ID NO |
|---|---|---|---|---|
| GAPDH | Human | Forward Primer | CAACGGATTTGGTCGT ATTGG | 15 |
| GAPDH | Human | Reverse Primer | GGCAACAATATCCACT TTACCAGAGT | 16 |
| GAPDH | Human | Probe | CGCCTGGTCACCAGGG CTGCT | 17 |
| GAPDH | Human | Forward Primer | GAAGGTGAAGGTCGGA GTC | 18 |
| GAPDH | Human | Reverse Primer | GAAGATGGTGATGGGA TTTC | 19 |
| GAPDH | Human | Probe | CAAGCTTCCCGTTCTC AGCC | 20 |
| GAPDH | Human | Forward Primer | GAAGGTGAAGGTCGGA GTC | 18 |
| GAPDH | Human | Reverse Primer | GAAGATGGTGATGGGA TTTC | 19 |
| GAPDH | Human | Probe | TGGAATCATATTGGAA CATG | 21 |
| GAPDH | Mouse | Forward Primer | GGCAAATTCAACGGCA CAGT | 22 |
| GAPDH | Mouse | Reverse Primer | GGGTCTCGCTCCTGGA AGAT | 23 |
| GAPDH | Mouse | Probe | AAGGCCGAGAATGGGA AGCTTGTCATC | 24 |
| GAPDH | Rat | Forward Primer | TGTTCTAGAGACAGCC GCATCTT | 25 |
| GAPDH | Rat | Reverse Primer | CACCGACCTTCACCAT CTTGT | 26 |
| GAPDH | Rat | Probe | TTGTGCAGTGCCAGCC TCGTCTCA | 27 |

Probes and primers for use in real-time PCR were designed to hybridize to target-specific sequences. The primers and probes and the target nucleic acid sequences to which they hybridize are presented in Table 3. The target-specific PCR probes have FAM covalently linked to the 5' end and TAMRA or MGB covalently linked to the 3' end, where FAM is the fluorescent dye and TAMRA or MGB is the quencher dye.

TABLE 3

Gene target-specific primers and probes for use in real-time PCR

| Species | Target SEQ ID NO | Sequence Description | Sequence (5' to 3') | SEQ ID NO |
|---|---|---|---|---|
| Human | 4 | Forward Primer | CTTCAATGAAACGTGG GAGAACT | 28 |
| Human | 4 | Reverse Primer | TCTCTAGGCCCAACCA AAATTC | 29 |
| Human | 4 | Probe | AAATATGGTTTTGGGA GGCTTGAT | 30 |
| Mouse | 6 | Forward Primer | CAGAAGTAACATCACT CAAAAGTTTTGTAG | 31 |
| Mouse | 6 | Reverse Primer | GACTTAATTGTTTATA TCTGTCTTCCACACT | 32 |
| Mouse | 6 | Probe | CAGCAAGACAACAGCA TAAGAGAACTCCTCCA | 33 |

Analysis of Protein Levels

Antisense inhibition of ANGPTL3 nucleic acids can be assessed by measuring ANGPTL3 protein levels. Protein levels of ANGPTL3 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS) (Sambrooke and Russell, Molecular Cloning: A Laboratory Manual, $3^{rd}$ Ed., 2001). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

In Vivo Testing of Antisense Compounds

Antisense compounds, for example, antisense oligonucleotides, are tested in animals to assess their ability to inhibit expression of ANGPTL3 and produce phenotypic changes. Testing can be performed in normal animals, or in experimental disease models. For administration to animals, antisense oligonucleotides are formulated in a pharmaceutically acceptable diluent, such as phosphate-buffered saline. Administration includes parenteral routes of administration. Following a period of treatment with antisense oligonucleotides, RNA is isolated from tissue and changes in ANGPTL3 nucleic acid expression are measured. Changes in ANGPTL3 protein levels are also measured.

Certain Indications

In certain embodiments, provided herein are methods of treating an individual comprising administering one or more pharmaceutical compositions as described herein. In certain embodiments, the individual has a metabolic disease and/or cardiovascular disease. In certain embodiments, the individual has atherosclerosis, hepatic steatosis or hyperlipidemia.

Accordingly, provided herein are methods for ameliorating a symptom associated with a metabolic disease or cardiovascular disease. Also provided herein are methods for ameliorating a symptom associated with atherosclerosis, hepatic steatosis or hyperlipidemia in a subject in need thereof. In certain embodiments, provided is a method for reducing the rate of onset of a symptom associated with a metabolic disease or cardiovascular disease. In certain embodiments, provided is a method for reducing the rate of onset of a symptom associated atherosclerosis, hepatic steatosis or hyperlipidemia. In certain embodiments, provided is a method for reducing the severity of a symptom associated with a metabolic disease or cardiovascular disease. In certain embodiments, provided is a method for reducing the severity of a symptom associated with atherosclerosis, hepatic steatosis or hyperlipidemia. In such embodiments, the methods comprise administering to an individual in need thereof a therapeutically effective amount of a compound targeted to an ANGPTL3 nucleic acid.

In certain embodiments, administration of an antisense compound targeted to an ANGPTL3 nucleic acid results in reduction of ANGPTL3 expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to ANGPTL3 are used for the preparation of a medicament for treating a patient suffering from, or susceptible to, a metabolic disease or cardiovascular disease. In certain embodiments, pharmaceutical compositions comprising an antisense compound targeted to ANGPTL3 are used for the preparation of a medicament for treating a patient suffering from, or susceptible to, atherosclerosis, hepatic steatosis or hyperlipidemia.

In certain embodiments, the methods described herein include administering a compound comprising a modified oligonucleotide having an 8, 9, 10, 11, 12, 13, 14, 15, 16, 17, 18, 19 or 20 contiguous nucleobase portion as described herein of a sequence recited in SEQ ID NO: 34-182.

Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump.

In certain embodiments, parenteral administration is by injection. The injection can be delivered with a syringe or a pump. In certain embodiments, the injection is a bolus injection. In certain embodiments, the injection is administered directly to a tissue or organ.

Certain Combination Therapies

In certain embodiments, a first agent comprising the modified oligonucleotide of the invention is co-administered with one or more secondary agents. In certain embodiments, such second agents are designed to treat the same disease, disorder or condition as the first agent described herein. In certain embodiments, such second agents are designed to treat a different disease, disorder, or condition as the first agent described herein. In certain embodiments, such second agents are designed to treat an undesired side effect of one or more pharmaceutical compositions as described herein. In certain embodiments, second agents are co-administered with the first agent to treat an undesired effect of the first agent. In certain embodiments, second agents are co-administered with the first agent to produce a combinational effect. In certain embodiments, second agents are co-administered with the first agent to produce a synergistic effect.

In certain embodiments, a first agent and one or more second agents are administered at the same time. In certain embodiments, the first agent and one or more second agents are administered at different times. In certain embodiments, the first agent and one or more second agents are prepared together in a single pharmaceutical formulation. In certain embodiments, the first agent and one or more second agents are prepared separately.

In certain embodiments, second agents include, but are not limited to ascorbic acid.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Inhibition of Human Angiopoietin-like 3 by Oligomeric Compounds

A series of oligomeric compounds was designed to target different regions of human angiopoietin-like 3, using published sequences cited in Table 1. The compounds are shown in Table 4. All compounds in Table 4 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytosine residues are 5-methylcytosines. The oligomeric compounds in Table 4 specifically hybridize to a target nucleic acid molecule encoding angiopoietin-like 3 and are comprised of regions that increase binding affinity, these regions being the "wings" of the oligomeric compounds. The oligomeric compounds each comprise a region that elicits RNase H activity, this regions being the "gap" region.

The compounds were analyzed for their effect on gene target mRNA levels by quantitative real-time PCR as described in other examples herein, using the target-specific primers and probe shown in Table 3 (SEQ ID NO: 28, SEQ ID NO: 29, and SEQ ID NO: 30). Data are averages from experiments in which Huh7 cells were treated with 150 nM of the disclosed oligomeric compounds using OLIGO-FECTAMINE™. Shown in Table 4 is the SEQ ID NO of the sequence to which each oligomeric compound is targeted.

A reduction in expression is expressed as percent inhibition in Table 4. If present, "N.D." indicates "not determined". The target regions to which these oligomeric compounds are inhibitory are herein referred to as "validated target segments."

TABLE 4

Inhibition of human angiopoietin-like 3 mRNA levels by chimeric oligonucleotides having 2'-MOE wings and deoxy gap

| ISIS # | Target SEQ ID NO | Target Site | Sequence (5' to 3') | % Inhib | SEQ NO ID |
|---|---|---|---|---|---|
| 337529 | 1 | 548 | ATCTGTTGTGATGTCGATAA | 66 | 34 |
| 337527 | 2 | 336 | GTATTTAGTCAAGTTTAGAG | 39 | 35 |
| 337528 | 2 | 429 | TATTACAGATTTTTACACAT | 21 | 36 |
| 337526 | 3 | 33 | CGTGGAACTGTTTTCTTCTG | 63 | 37 |
| 337459 | 4 | 22 | AGCTTAATTGTGAACATTTT | 73 | 38 |
| 337460 | 4 | 61 | ATTCTGGAGGAAATAACTAG | 34 | 39 |
| 233675 | 4 | 116 | AAATCTTGATTTTGGCTCTG | 61 | 40 |
| 233676 | 4 | 121 | ATAGCAAATCTTGATTTTGG | 52 | 41 |
| 337461 | 4 | 126 | CTAACATAGCAAATCTTGAT | 53 | 42 |
| 337462 | 4 | 131 | ATCGTCTAACATAGCAAATC | 43 | 43 |
| 337463 | 4 | 154 | AGGCCATTGGCTAAAATTTT | 37 | 44 |
| 337464 | 4 | 171 | CATGTCCCAACTGAAGGAGG | 41 | 45 |
| 337465 | 4 | 180 | CTTTAAGACCATGTCCCAAC | 0 | 46 |
| 337466 | 4 | 203 | GCCCTTCGTCTTATGGACAA | 28 | 47 |
| 337467 | 4 | 214 | TCATTAATTTGGCCCTTCGT | 38 | 48 |
| 337468 | 4 | 223 | TGAAATATGTCATTAATTTG | 0 | 49 |
| 233690 | 4 | 247 | GACTGATCAAATATGTTGAG | 53 | 50 |
| 337469 | 4 | 271 | GTTTGCAGCGATAGATCATA | 56 | 51 |
| 337470 | 4 | 277 | TCACTGGTTTGCAGCGATAG | 62 | 52 |

TABLE 4 -continued

Inhibition of human angiopoietin-like 3 mRNA levels by chimeric oligonucleotides having 2'-MOE wings and deoxy gap

| ISIS # | Target SEQ ID NO | Target Site | Sequence (5' to 3') | % Inhib | SEQ NO ID |
|---|---|---|---|---|---|
| 337471 | 4 | 364 | AGTTCAAGTGACATATTCTT | 52 | 53 |
| 337472 | 4 | 496 | AGTGAAGTTACTTCTGGGTG | 59 | 54 |
| 337473 | 4 | 502 | GTTTTAAGTGAAGTTACTTC | 50 | 55 |
| 337474 | 4 | 510 | CTACAAAAGTTTTAAGTGAA | 25 | 56 |
| 337475 | 4 | 558 | GGTCTTCCACGGTCTGGAGA | 70 | 57 |
| 337476 | 4 | 624 | TAGTCCTTCTGAGCTGATTT | 66 | 58 |
| 337477 | 4 | 637 | GGTTCTTGAATACTAGTCCT | 80 | 59 |
| 337478 | 4 | 648 | AAATTTCTGTGGGTTCTTGA | 74 | 60 |
| 337479 | 4 | 665 | TGGCTTGGAAGATAGAGAAA | 77 | 61 |
| 233710 | 4 | 683 | AGTAGTTCTTGGTGCTCTTG | 82 | 62 |
| 337480 | 4 | 694 | TGAAGAAAGGGAGTAGTTCT | 60 | 63 |
| 337481 | 4 | 701 | ATTCAACTGAAGAAAGGGAG | 59 | 64 |
| 337482 | 4 | 710 | TCTTATTTCATTCAACTGAA | 32 | 65 |
| 337483 | 4 | 734 | AGGAATGCCATCATGTTTTA | 39 | 66 |
| 337484 | 4 | 762 | CTCTGTTATAAATGGTGGTA | 65 | 67 |
| 337485 | 4 | 767 | TTCACCTCTGTTATAAATGG | 31 | 68 |
| 337486 | 4 | 772 | GTATGTTCACCTCTGTTATA | 47 | 69 |
| 337487 | 4 | 777 | CACTTGTATGTTCACCTCTG | 75 | 70 |
| 337488 | 4 | 782 | CATGCCACTTGTATGTTCAC | 44 | 71 |
| 337489 | 4 | 806 | AGAGTTGCTGGGTCTGATGG | 52 | 72 |
| 337490 | 4 | 840 | CTGATATAACATCACAGTAG | 54 | 73 |
| 337491 | 4 | 850 | CATGGACTACCTGATATAAC | 60 | 74 |
| 233717 | 4 | 862 | TGAATTAATGTCCATGGACT | 85 | 75 |
| 337492 | 4 | 874 | TCTATTCGATGTTGAATTAA | 13 | 76 |
| 337493 | 4 | 909 | AGTTCTCCCACGTTTCATTG | 80 | 77 |
| 337494 | 4 | 918 | CATATTTGTAGTTCTCCCAC | 62 | 78 |
| 337495 | 4 | 923 | AAAACCATATTTGTAGTTCT | 25 | 79 |
| 337496 | 4 | 930 | GCCTCCCAAAACCATATTTG | 35 | 80 |
| 337497 | 4 | 953 | GCCCAACCAAAATTCTCCAT | 70 | 81 |
| 233721 | 4 | 959 | CTCTAGGCCCAACCAAAATT | 73 | 82 |
| 233722 | 4 | 964 | ATCTTCTCTAGGCCCAACCA | 91 | 83 |
| 337498 | 4 | 995 | AACATAATTAGATTGCTTCA | 26 | 84 |
| 337499 | 4 | 1016 | GTCTTCCAACTCAATTCGTA | 56 | 85 |
| 337500 | 4 | 1023 | CTTTCCAGTCTTCCAACTCA | 38 | 86 |
| 337501 | 4 | 1094 | AACTAGATGTAGCGTATAGT | 65 | 87 |
| 337502 | 4 | 1162 | TGATCCCAAGTAGAAAACAC | 33 | 88 |
| 337503 | 4 | 1213 | CACCAGCCTCCTGAATAACC | 32 | 89 |

TABLE 4 -continued

Inhibition of human angiopoietin-like 3 mRNA levels by chimeric oligonucleotides having 2'-MOE wings and deoxy gap

| ISIS # | Target SEQ ID NO | Target Site | Sequence (5' to 3') | % Inhib | SEQ NO ID |
|---|---|---|---|---|---|
| 337504 | 4 | 1245 | TTAGGTTGTTTTCTCCACAC | 68 | 90 |
| 337505 | 4 | 1301 | TAATCCTCTTCTCCTCTCTG | 32 | 91 |
| 337506 | 4 | 1315 | TGAGACTTCCAAGATAATCC | 63 | 92 |
| 337507 | 4 | 1320 | CATTTTGAGACTTCCAAGAT | 48 | 93 |
| 337508 | 4 | 1333 | GAGTATAACCTTCCATTTTG | 54 | 94 |
| 337509 | 4 | 1364 | TGGATGGATCAACATTTTGG | 67 | 95 |
| 337510 | 4 | 1385 | TTCAAAGCTTTCTGAATCTG | 62 | 96 |
| 337511 | 4 | 1397 | TGCCTCAGTTCATTCAAAGC | 58 | 97 |
| 337512 | 4 | 1410 | TGCCTTTTAAATTTGCCTCA | 64 | 98 |
| 337513 | 4 | 1443 | ATTAACTTGGAATGAGGTTA | 65 | 99 |
| 337514 | 4 | 1450 | AGACCACATTAACTTGGAAT | 62 | 100 |
| 337515 | 4 | 1458 | AGATTATTAGACCACATTAA | 44 | 101 |
| 337516 | 4 | 1463 | ATACCAGATTATTAGACCAC | 65 | 102 |
| 337517 | 4 | 1470 | GGATTTAATACCAGATTATT | 64 | 103 |
| 337518 | 5 | 1678 | ACTGACTTACCTGATTTTCT | 0 | 104 |
| 337519 | 5 | 2294 | ACCTTGTAAGTCTTCATTGG | 52 | 105 |
| 337520 | 5 | 3809 | CAGTGTTATTCAGATTGTAC | 56 | 106 |
| 337521 | 5 | 4068 | AGTGTCTTACCATCATGTTT | 56 | 107 |
| 337522 | 5 | 5100 | ACAGATGTAAATAACACTTT | 19 | 108 |
| 337523 | 5 | 5252 | GTCCCCTTACCATCAAGCCT | 49 | 109 |
| 337524 | 5 | 7150 | GGGAAGATACTTTGAAGATA | 50 | 110 |
| 337525 | 5 | 7504 | CACCAGCCTCCTAAAGGAGA | 27 | 111 |

Example 2

Antisense Inhibition of Mouse Angiopoietin-like 3 by Oligomeric Compounds

A series of oligomeric compounds was designed to target different regions of mouse angiopoietin-like 3, using published sequences cited in Table 1. The compounds are shown in Table 5. All compounds in Table 5 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytosine residues are 5-methylcytosines. The oligomeric compounds in Table 5 specifically hybridize to a target nucleic acid molecule encoding angiopoietin-like 3 and are comprised of regions that increase binding affinity, these regions being the "wings" of the oligomeric compounds. The oligomeric compounds each comprise a region that elicits RNase H activity, this region being the "gap" region.

The compounds were analyzed for their effect on gene target mRNA levels by quantitative real-time PCR as described in other examples herein, using the target-specific primers and probe shown in Table 3 (SEQ ID NO: 31, SEQ ID NO: 32, and SEQ ID NO: 33). Data are averages from experiments in which mouse primary hepatocytes were treated with 150 nM of the disclosed oligomeric compounds using LIPO-FECTIN™. The control oligomeric compounds used were SEQ ID NOs: 9 and 10. Shown in Table 5 is the SEQ ID NO of the sequence to which each oligomeric compound is targeted.

A reduction in expression is expressed as percent inhibition in Table 5. If present, "N.D." indicates "not determined". The target regions to which these oligomeric compounds are inhibitory are herein referred to as "validated target segments". The antisense oligonucleotides of Table 5 may also be cross reactive with the human ANGPTL3 mRNA (GENBANK Accession NM_014495.1, incorporated herein as SEQ ID NO: 4), depending on the number of mismatched nucleobases the murine oligonucleotide has with the human ANGPTL3 sequence. "Human Target Start Site" indicates the 5'-most nucleotide in the human mRNA to which the antisense oligonucleotide is targeted. "Human Target Stop Site"

indicates the 3'-most nucleotide in the human mRNA to which the antisense oligonucleotide is targeted. 'Mismatches' indicates the number of nucleobases by which the murine oligonucleotide is mismatched with the human gene sequence. The designation "n/a" indicates that there was greater than 3 mismatches between the murine oligonucleotide and the human gene sequence. The greater the complementarity between the murine oligonucleotide and the human gene sequence, the more likely the murine oligonucleotide can cross-react with the human gene sequence.

TABLE 5

Inhibition of mouse angiopoietin-like 3 mRNA levels by chimeric oligonucleotides having 2'-MOE wings and deoxy gap

| ISIS # | Target SEQ ID NO | Target Site | Sequence (5' to 3') | % Inhib | SEQ ID NO | Human Target Start Site | Mismatches with human target |
|---|---|---|---|---|---|---|---|
| 233671 | 6 | 19 | AATAATTTAATTGTGTGCAT | 13 | 112 | n/a | n/a |
| 233672 | 6 | 56 | CACTCTGGATGCAATTACTA | 66 | 113 | n/a | n/a |
| 233673 | 6 | 68 | AAGGTCTGGATCCACTCTGG | 74 | 114 | n/a | n/a |
| 233674 | 6 | 100 | TTTGGCTCTGAAGGTGCAGA | 66 | 115 | n/a | n/a |
| 233675 | 6 | 110 | AAATCTTGATTTTGGCTCTG | 80 | 40 | 116 | 0 |
| 233676 | 6 | 115 | ATAGCAAATCTTGATTTTGG | 49 | 41 | 121 | 0 |
| 233677 | 6 | 124 | TCATCCAACATAGCAAATCT | 24 | 116 | 130 | 2 |
| 233678 | 6 | 129 | TGACATCATCCAACATAGCA | 66 | 117 | 135 | 3 |
| 233679 | 6 | 134 | AATTTTGACATCATCCAACA | 76 | 118 | 140 | 3 |
| 233680 | 6 | 139 | GCTAAAATTTTGACATCATC | 72 | 119 | 145 | 2 |
| 233681 | 6 | 148 | AGGCCATTCGCTAAAATTTT | 52 | 120 | 154 | 1 |
| 233682 | 6 | 160 | CCCAGCTGCAGGAGGCCATT | 77 | 121 | 166 | 2 |
| 233683 | 6 | 165 | CATGACCCAGCTGCAGGAGG | 51 | 122 | 171 | 3 |
| 233684 | 6 | 172 | TTAAGTCCATGACCCAGCTG | 71 | 123 | 178 | 3 |
| 233685 | 6 | 182 | GACAAAATCTTTAAGTCCAT | 27 | 124 | 188 | 2 |
| 233686 | 6 | 187 | TTATGGACAAAATCTTTAAG | 29 | 125 | 193 | 1 |
| 233687 | 6 | 226 | TTGAGCTTCTGAAATATGTC | 56 | 126 | 232 | 2 |
| 233688 | 6 | 231 | ATATGTTGAGCTTCTGAAAT | 53 | 127 | 237 | 2 |
| 233689 | 6 | 236 | ATCAAATATGTTGAGCTTCT | 47 | 128 | 242 | 2 |
| 233690 | 6 | 241 | GACTGATCAAATATGTTGAG | 73 | 50 | 247 | 0 |
| 233691 | 6 | 266 | GGTTCGAAGTGATAGGTCAT | 63 | 129 | n/a | n/a |
| 233692 | 6 | 317 | TAGTGTAGATGTAGTTCTTC | 44 | 130 | 323 | 2 |
| 233693 | 6 | 349 | GACATGTTCTTCACCTCCTC | 80 | 131 | 355 | 3 |
| 233694 | 6 | 365 | TGAGTTCAGTTCTACTGACA | 78 | 132 | 371 | 3 |
| 233695 | 6 | 373 | TCAAGCTTTGAGTTCAGTTC | 71 | 133 | 379 | 2 |
| 233696 | 6 | 394 | GTCTTCTCTTCCAGCAGACT | 71 | 134 | n/a | n/a |
| 233697 | 6 | 405 | GTTGAAGGGCTGTCTTCTCT | 75 | 135 | n/a | n/a |
| 233698 | 6 | 415 | CTGACCTTGTGTTGAAGGGC | 92 | 136 | n/a | n/a |
| 233699 | 6 | 423 | CCAAAGCCCTGACCTTGTGT | 60 | 137 | n/a | n/a |
| 233700 | 6 | 435 | TTAGCTGCTCCTCCAAAGCC | 68 | 138 | n/a | n/a |
| 233701 | 6 | 451 | CTTAGAATTAAGTTGGTTAG | 49 | 139 | 457 | 3 |
| 233702 | 6 | 474 | GGTGCTCCTGAGCCCCAGCT | 82 | 140 | n/a | n/a |
| 233703 | 6 | 488 | TGATGTTACTTCTGGGTGCT | 63 | 141 | 494 | 2 |

TABLE 5 -continued

Inhibition of mouse angiopoietin-like 3 mRNA levels by chimeric oligonucleotides having 2'-MOE wings and deoxy gap

| ISIS # | Target SEQ ID NO | Target Site | Sequence (5' to 3') | % Inhib | SEQ ID NO | Human Target Start Site | Mismatches with human target |
|---|---|---|---|---|---|---|---|
| 233704 | 6 | 511 | TGCTGTTCTACAAAACTTTT | 79 | 142 | 517 | 3 |
| 233705 | 6 | 535 | AGGAGTTCTCTTATGCTGTT | 86 | 143 | n/a | n/a |
| 233706 | 6 | 540 | TCTGGAGGAGTTCTCTTATG | 58 | 144 | n/a | n/a |
| 233707 | 6 | 545 | CACACTCTGGAGGAGTTCTC | 77 | 145 | n/a | n/a |
| 233708 | 6 | 632 | GGGTTCTTGAATACCAGTCT | 58 | 146 | 638 | 2 |
| 233709 | 6 | 649 | GAAAGAGAATTTTCTGAGGG | 29 | 147 | 655 | 3 |
| 233710 | 6 | 677 | AGTAGTTCTTGGTGCTCTTG | 68 | 62 | 683 | 0 |
| 233711 | 6 | 730 | GCAGGAAGGTCATCTTGTTC | 62 | 148 | n/a | n/a |
| 233712 | 6 | 739 | GAGCAGTCGGCAGGAAGGTC | 62 | 149 | n/a | n/a |
| 233713 | 6 | 778 | TACACGCCACTTGTATGTTC | 55 | 150 | 784 | 1 |
| 233714 | 6 | 787 | TTAATAGTGTACACGCCACT | 62 | 151 | n/a | n/a |
| 233715 | 6 | 816 | AGACATTAAACCCTTGGGAG | 47 | 152 | n/a | n/a |
| 233716 | 6 | 838 | CTGCCTGATTGGGTATCACA | 76 | 153 | n/a | n/a |
| 233717 | 6 | 856 | TGAATTAATGTCCATGGACT | 61 | 75 | 862 | 0 |
| 233718 | 6 | 871 | CCATCTTTCCGGTGTTGAAT | 64 | 154 | 877 | 3 |
| 233719 | 6 | 884 | GAAGTCCTGTGAGCCATCTT | 69 | 155 | n/a | n/a |
| 233720 | 6 | 935 | TTCTCCATCGAGCCTCCCAA | 56 | 156 | 941 | 1 |
| 233721 | 6 | 953 | CTCTAGGCCCAACCAAAATT | 67 | 82 | 959 | 0 |
| 233722 | 6 | 958 | ATCTTCTCTAGGCCCAACCA | 63 | 83 | 964 | 0 |
| 233723 | 6 | 975 | GTTGGACTATAGCATAGATC | 70 | 157 | n/a | n/a |
| 233724 | 6 | 988 | ATGTAGTTAGACTGTTGGAC | 57 | 158 | n/a | n/a |
| 233725 | 6 | 1033 | ACGTAGTGCTTGCTGTCTTT | 81 | 159 | n/a | n/a |
| 233726 | 6 | 1055 | GCCCAGGTGAAAGGAGTATT | 70 | 160 | n/a | n/a |
| 233727 | 6 | 1081 | TGTAGCGTGTAGTTGGTTTC | 38 | 161 | 1087 | 1 |
| 233728 | 6 | 1086 | CCACATGTAGCGTGTAGTTG | 59 | 162 | 1092 | 3 |
| 233729 | 6 | 1091 | CTCAGCCACATGTAGCGTGT | 57 | 163 | n/a | n/a |
| 233730 | 6 | 1096 | GCAATCTCAGCCACATGTAG | 62 | 164 | n/a | n/a |
| 233731 | 6 | 1138 | ATCAGGTCTGTGTGCTCTGG | 75 | 165 | n/a | n/a |
| 233732 | 6 | 1149 | ATGTAGAAAACATCAGGTCT | 66 | 166 | n/a | n/a |
| 233733 | 6 | 1160 | TCTGTGATTCCATGTAGAAA | 61 | 167 | 1166 | 3 |
| 233734 | 6 | 1186 | TCTGGACAGTAGAGCTGTCC | 46 | 168 | 1192 | 3 |
| 233735 | 6 | 1191 | AACTTTCTGGACAGTAGAGC | 58 | 169 | n/a | n/a |
| 233736 | 6 | 1209 | ACCACCAGCCACCTGAGTAA | 60 | 170 | 1215 | 2 |
| 233737 | 6 | 1229 | TTCTCCACATATGTCATTCC | 56 | 171 | n/a | n/a |
| 233738 | 6 | 1236 | GGTTGTTTTCTCCACATATG | 70 | 172 | n/a | n/a |
| 233739 | 6 | 1277 | TGGTCTGGATTTGGTTCTGG | 71 | 173 | n/a | n/a |

TABLE 5 -continued

Inhibition of mouse angiopoietin-like 3 mRNA levels by chimeric
oligonucleotides having 2'-MOE wings and deoxy gap

| ISIS # | Target SEQ ID NO | Target Site | Sequence (5' to 3') | % Inhib | SEQ ID NO | Human Target Start Site | Mismatches with human target |
|---|---|---|---|---|---|---|---|
| 233740 | 6 | 1283 | TCTCTCTGGTCTGGATTTGG | 73 | 174 | n/a | n/a |
| 233741 | 6 | 1324 | TAGAGCTTTCTGCTCTGAGG | 64 | 175 | n/a | n/a |
| 233742 | 6 | 1363 | GTGGTGGGCTGGAGCATCAT | 57 | 176 | n/a | n/a |
| 233743 | 6 | 1376 | TGAAGCTTCTTAGGTGGTGG | 55 | 177 | n/a | n/a |
| 233744 | 6 | 1390 | TGTCTCAGTTCAGTTGAAGC | 60 | 178 | n/a | n/a |
| 233745 | 6 | 1430 | TCGGGAGGACTTTAATATTT | 50 | 179 | n/a | n/a |
| 233746 | 7 | 13 | GGAACTTCTCCCTCCTGTCC | 49 | 180 | n/a | n/a |
| 233747 | 8 | 202 | TAACAATGAGTTTAAACCTA | 17 | 181 | n/a | n/a |
| 233748 | 8 | 210 | TCTGATCTTAACAATGAGTT | 0 | 182 | n/a | n/a |

Example 3

Design and Screening of Duplexed Oligomeric Compounds Targeting Angiopoietin-like 3

In accordance with the invention, a series of duplexes, including dsRNA and mimetics thereof, comprising oligomeric compounds of the invention and their complements can be designed to target angiopoietin-like 3. The nucleobase sequence of the antisense strand of the duplex comprises at least a portion of an oligonucleotide targeted to angiopoietin-like 3 as disclosed herein. The ends of the strands may be modified by the addition of one or more natural or modified nucleobases to form an overhang. The sense strand of the nucleic acid duplex is then designed and synthesized as the complement of the antisense strand and may also contain modifications or additions to either terminus. The antisense and sense strands of the duplex comprise from about 17 to 25 nucleotides, or from about 19 to 23 nucleotides. Alternatively, the antisense and sense strands comprise 20, 21 or 22 nucleotides.

For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (incorporated herein as SEQ ID NO: 183) and having a two-nucleobase overhang of deoxythymidine(dT) would have the following structure:

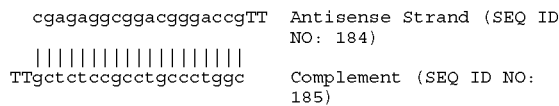

Antisense Strand (SEQ ID NO: 184)

Complement (SEQ ID NO: 185)

Overhangs can range from 2 to 6 nucleobases and these nucleobases may or may not be complementary to the target nucleic acid. In another embodiment, the duplexes can have an overhang on only one terminus.

In another embodiment, a duplex comprising an antisense strand having the same sequence, for example CGAGAG-GCGGACGGGACCG (SEQ ID NO: 183), can be prepared with blunt ends (no single stranded overhang) as shown:

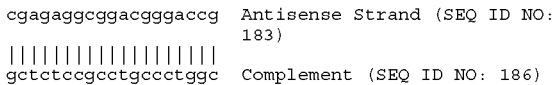

Antisense Strand (SEQ ID NO: 183)

Complement (SEQ ID NO: 186)

The RNA duplex can be unimolecular or bimolecular; i.e, the two strands can be part of a single molecule or may be separate molecules.

RNA strands of the duplex can be synthesized by methods routine to the skilled artisan or purchased from Dharmacon Research Inc. (Lafayette, Colo.). Once synthesized, the complementary strands are annealed. The single strands are aliquoted and diluted to a concentration of 50 µM. Once diluted, 30 µL, of each strand is combined with 15 µL of a 5× solution of annealing buffer. The final concentration of said buffer is 100 mM potassium acetate, 30 mM HEPES-KOH pH 7.4, and 2 mM magnesium acetate. The final volume is 75 µL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 µM.

Once prepared, the duplexed compounds are evaluated for their ability to modulate angiopoietin-like 3. When cells reached 80% confluency, they are treated with duplexed compounds of the invention. For cells grown in 96-well plates, wells are washed once with 200 µL, OPTI-MEM-1™ reduced-serum medium (Gibco BRL) and then treated with 130 µL, of OPTI-MEM-1™ containing 12 µg/mL LIPOFECTIN™ (Gibco BRL) and the desired duplex antisense compound at a final concentration of 200 nM (a ratio of 6 µg/mL LIPOFECTIN™ per 100 nM duplex antisense compound). After 5 hours of treatment, the medium is replaced with fresh medium. Cells are harvested 16 hours after treatment, at which time RNA is isolated and target reduction measured by RT-PCR.

Example 4

Antisense Inhibition of Mouse Angiopoietin-like 3 by Oligomeric Compounds: Dose Response Studies In a further embodiment of the present invention, three oligonucleotides were selected for additional dose-response studies. Mouse primary hepatocytes were treated with 6.25, 25, 100, or 400 nM of ISIS 233693 (SEQ ID NO: 131), ISIS 233698 (SEQ ID NO: 136), or ISIS 233725 (SEQ ID NO: 159), or the scrambled control oligonucleotide ISIS 113529 (5-10-5 gapmer, CTCTTACTGTGCTGTGGACA, incorporated herein as SEQ ID NO: 11) and mRNA levels were measured as described in other examples herein. Untreated cells served as the control to which the data were normalized.

Results of these studies are shown in Table 6. Data are averages from three experiments and are expressed as percent inhibition relative to untreated control.

TABLE 6

Inhibition of angiopoietin-like 3 mRNA expression in mouse primary hepatocytes

| Treatment | % Inhibition Dose (nM) | | | |
|---|---|---|---|---|
| | 6.25 | 25 | 100 | 400 |
| ISIS 233693 | 45 | 77 | 87 | 87 |
| ISIS 233698 | 0 | 13 | 33 | 52 |
| ISIS 233725 | 28 | 65 | 66 | 79 |
| ISIS 113529 | 0 | 0 | 0 | 0 |

As shown in Table 6, ISIS 233693, 233698, and 233725 reduced angiopoietin-like 3 mRNA levels in a dose-dependent manner.

Example 5

Effects of Antisense Inhibition of Angiopoietin-like 3: In Vivo Studies in C57BL/6 Mice In accordance with the present invention, two oligonucleotides targeting mouse angiopoietin-like 3 were chosen for in vivo studies. Male C57BL/6 mice fed normal chow were injected twice weekly with 50 mg/kg doses of either ISIS 233693 (SEQ ID NO: 131) or ISIS 233698 (SEQ ID NO: 136) for two weeks. Each treatment group was comprised of 5 animals. A group of animals received injections of saline twice weekly for 2 weeks. This saline-injected group served as the control group to which the oligonucleotide-treated groups were compared.

After the 2 week treatment period, the mice were sacrificed and angiopoietin-like 3 mRNA levels were evaluated in liver. mRNA expression levels were quantitated by real-time PCR as described in other examples herein. Relative to saline-treated mice, ISIS 233693 caused a 44% decrease in angiopoietin-like 3 mRNA levels. ISIS 233698 caused a 41% decrease in angiopoietin-like 3 mRNA levels. The data demonstrate that angiopoietin-like 3 antisense oligonucleotide treatment can effectively inhibit target mRNA expression in liver.

Spleen weight, body weight, and liver weight were measured at the end of the study. Average tissue and body weights measured (in grams) at the end of the treatment period are shown in Table 7. As shown in Table 7, body weight, liver weight and spleen weight were not affected by oligonucleotide treatment.

TABLE 7

Effect of antisense inhibition of angiopoietin-like 3 expression on tissue and body weights in lean mice

| Treatment | Body Weight | Liver Weight | Spleen Weight |
|---|---|---|---|
| Saline | 24 | 1.1 | 0.1 |
| ISIS 233693 | 23 | 1.1 | 0.1 |
| ISIS 233698 | 22 | 1.0 | 0.1 |

At study termination, the animals were evaluated for serum cholesterol, HDL, LDL, triglyceride and glucose levels by routine analysis using an Olympus Clinical Analyzer (Olympus America Inc., Melville, N.Y.). The serum transaminases ALT and AST, increases in which can indicate hepatotoxicity, were also measured. Levels of AST or ALT associated with liver toxicity were not observed. The levels of serum glucose (GLUC), cholesterol (CHOL), LDL, HDL, and triglycerides (TRIG) measured are presented in Table 8 as the average result from each treatment group in mg/dL.

TABLE 8

Effect of antisense inhibition of angiopoietin-like 3 expression on serum glucose, lipids, and transaminases in lean mice

| Treatment | CHOL | GLU | HDL | TG | LDL |
|---|---|---|---|---|---|
| Saline | 80 | 172 | 58 | 109 | 14 |
| ISIS 233693 | 70 | 251 | 53 | 72 | 10 |
| ISIS 233698 | 87 | 266 | 67 | 84 | 12 |

As shown in Table 8, treatment with ISIS 233693 and ISIS 233698 reduced serum triglycerides. Treatment with ISIS 233693 reduced total cholesterol.

Example 6

Effects of Antisense Inhibition of Angiopoietin-like 3: In Vivo Dose-Response Studies in High-Fat Fed Mice The C57BL/6 mouse strain is reported to be susceptible to hyperlipidemia-induced atherosclerotic plaque formation. Accordingly, these mice were fed a high-fat diet and used in the following studies to evaluate the effects of angiopoietin-like 3 antisense oligonucleotides on mRNA expression.

Male C57BL/6 mice were placed on a high-fat diet containing 60% calories from fat (for example, Research Diet D12492, Research Diets Inc., New Brunswick, N.J.). Mice receiving the high-fat diet were divided into treatment groups. Three groups received twice-weekly injections of ISIS 233693 (SEQ ID No: 131) at doses of 10 mg/kg, 25 mg/kg or 50 mg/kg, for 6 weeks. Three additional groups received twice-weekly injections of ISIS 233698 (SEQ ID No: 136) at doses of 10 mg/kg, 25 mg/kg or 50 mg/kg, for 6 weeks.

A group of high-fat fed animals received injections of saline twice weekly for 6 weeks. This saline-injected group served as the control group to which the oligonucleotide-treated groups were compared.

After the 6 week treatment period, the mice were sacrificed and angiopoietin-like 3 mRNA levels were evaluated in liver. mRNA expression levels were quantitated by real-time PCR as described in other examples herein. Results are presented in Table 9 as the average percentage inhibition relative to saline-treated control.

TABLE 9

Antisense inhibition of angiopoietin-like 3 expression in liver from high-fat fed mice: dose-response study

| Treatment | % Inhibition |
|---|---|
| ISIS 233693, 10 mg/kg | 73 |
| ISIS 233693, 25 mg/kg | 88 |
| ISIS 233693, 50 mg/kg | 93 |
| ISIS 233698, 10 mg/kg | 17 |
| ISIS 233698, 25 mg/kg | 39 |
| ISIS 233698, 50 mg/kg | 55 |

These data show that antisense oligonucleotides targeted to angiopoietin-like 3 mRNA effectively reduce target mRNA expression in liver in a dose-dependent manner.

Body weight was monitored throughout the study. Spleen weight, fat pad weight, and liver weight were measured at the end of the study. Average tissue and body weights measured at the end of the treatment period are shown in Table 10.

TABLE 10

Antisense inhibition of angiopoietin-like 3 expression on tissue and body weights in high-fat fed mice: dose-response study

| Treatment | Body Weight | Liver | Spleen | Fat Pad |
|---|---|---|---|---|
| Saline | 36 | 1.2 | 0.1 | 2.1 |
| ISIS 233693, 10 mg/kg | 37 | 1.5 | 0.1 | 2.0 |
| ISIS 233693, 25 mg/kg | 34 | 1.4 | 0.1 | 1.3 |
| ISIS 233693, 50 mg/kg | 32 | 1.5 | 0.1 | 1.1 |
| ISIS 233698, 10 mg/kg | 38 | 1.4 | 0.1 | 1.8 |
| ISIS 233698, 25 mg/kg | 33 | 1.2 | 0.1 | 1.5 |
| ISIS 233698, 50 mg/kg | 33 | 1.5 | 0.1 | 1.5 |

These data demonstrate that body weight, spleen weight and liver weight were not affected. Fat pad weight was reduced in a dose-dependent manner by treatment with ISIS 233698. Treatment with ISIS 233698 also reduced fat pad weight.

At study termination, the animals were evaluated for serum cholesterol, triglyceride and glucose levels by routine analysis using an Olympus Clinical Analyzer (Olympus America Inc., Melville, N.Y.). The serum transaminases ALT and AST, increases which can indicate hepatotoxicity, were also measured using an Olympus Clinical Analyzer (Olympus America Inc., Melville, N.Y.). The levels of serum cholesterol (CHOL) and triglycerides (TRIG) measured are presented in Table 11 as the average result from each treatment group in mg/dL. Also shown are the average levels of HDL and LDL as well as average glucose levels (GLUC). ALT and AST, also shown in Table 11, are likewise shown as the average result from each treatment group, in international units/L (IU/L).

TABLE 11

Effects of antisense inhibition of angiopoietin-like 3 on serum glucose, cholesterol, triglycerides, and liver transaminases in high-fat fed mice

| Treatment | ALT | AST | CHOL | HDL | LDL | TRIG | GLUC |
|---|---|---|---|---|---|---|---|
| Saline | 22 | 47 | 177 | 143 | 31 | 120 | 244 |
| ISIS 233693, 10 mg/kg | 23 | 60 | 151 | 127 | 23 | 81 | 263 |
| ISIS 233693, 25 mg/kg | 21 | 62 | 125 | 106 | 18 | 57 | 254 |
| ISIS 233693, 50 mg/kg | 52 | 79 | 147 | 125 | 22 | 44 | 206 |
| ISIS 233698, 10 mg/kg | 28 | 55 | 151 | 120 | 27 | 101 | 285 |
| ISIS 233698, 25 mg/kg | 16 | 53 | 135 | 110 | 23 | 89 | 248 |
| ISIS 233698, 50 mg/kg | 192 | 175 | 158 | 126 | 31 | 77 | 215 |

As shown in Table 11, as compared to saline-treatment, treatment with ISIS 233693 or ISIS 233698 resulted in decreased cholesterol levels and dose-dependent decreases in serum triglycerides. ISIS 233693 and ISIS 233698 also resulted in a slight decrease in HDL which is commonly observed in mice when hypolipidemic agents are tested due to the fact that mice, unlike humans and other species, carry 90% of their serum cholesterol as HDL particles. Furthermore, treatment with ISIS 233693 decreased LDL.

Example 7

Effects of Antisense Inhibition of Angiopoietin-like 3 Levels In Vivo: Liver Triglycerides Hepatic steatosis refers to the accumulation of lipids in the liver, or "fatty liver", which is frequently caused by alcohol consumption, diabetes and hyperlipidemia and can progress to end-stage liver damage. Given the deleterious consequences of a fatty liver condition, it is of use to identify compounds that prevent or ameliorate hepatic steatosis. Hepatic steatosis may be evaluated both by measurement of tissue triglyceride content and by histologic examination of liver tissue.

In a further embodiment, liver tissue triglyceride content was assessed in the animals described in Example 6. Liver tissue triglyceride content was measured using the Triglyceride GPO assay (Roche Diagnostics, Indianapolis, Ind.). Results for each treatment group were normalized to saline-treated control and are presented in Table 12.

TABLE 12

Effects of antisense inhibition of angiopoietin-like 3 on liver triglycerides in high-fat fed mice

| Treatment | % Control |
|---|---|
| ISIS 233693, 10 mg/kg | 82 |
| ISIS 233693, 25 mg/kg | 54 |
| ISIS 233693, 50 mg/kg | 31 |
| ISIS 233698, 10 mg/kg | 55 |
| ISIS 233698, 25 mg/kg | 41 |
| ISIS 233698, 50 mg/kg | 47 |

As shown in Table 12, treatment with antisense oligonucleotides targeted to angiopoietin-like 3 results in dose-dependent reduction in liver triglycerides.

Example 8

Effects of Antisense Inhibition of Angiopoietin-like 3: In Vivo Studies with ISIS 233693 in High-Fat Fed Mice In a study similar to that described in Example 6, male C57BL/6 mice were placed on a high-fat diet containing 60% calories from fat (for example, Research Diet D12492, Research Diets Inc., New Brunswick, N.J.). Mice receiving the high-fat diet were divided into treatment groups. One group received twice-weekly injections of ISIS 233693 (SEQ ID No: 131) at doses of 50 mg/kg, for 6 weeks.

Oligonucleotides were dissolved in saline for injection. A group of high-fat fed animals received injections of saline twice weekly for 6 weeks. This saline-injected group served as the control group to which the oligonucleotide-treated groups were compared.

After the 6 week treatment period, the mice were sacrificed and angiopoietin-like 3 mRNA levels were evaluated in liver. mRNA expression levels were quantitated by real-time PCR as described in other examples herein. ISIS 233693 caused an 88% reduction in target mRNA levels.

Body weight was monitored throughout the study. Spleen weight, fat pad weight, and liver weight were measured at the end of the study. The average body weight, liver weight, spleen weight, and fat pad weight for animals treated with saline alone were 33 g, 1.2 g, 0.1 g, 0.7 g, respectively. The average body weight, liver weight, spleen weight, and fat pad weight for animals treated with ISIS 233693 were 31 g, 1.6 g, 0.2 g, and 0.2 g, respectively. Treatment with ISIS 233693 reduced fat pad weight by 71%.

At study termination, the animals were evaluated for serum cholesterol, triglyceride and glucose levels by routine clinical analyses (for example at a clinical testing facility such as BTS, a division of Lab Corp, San Diego, Calif.). The serum transaminases ALT and AST, and serum protein, increases in which can indicate hepatotoxicity, and levels of bilirubin, increases in which can indicate kidney toxicity, were also measured. Toxic increases as indicators of aberrant kidney or liver function were not observed with ISIS 233693 treatment. ISIS 233693 caused a reduction in serum triglyceride and glucose levels, but did not alter serum cholesterol, LDL, or HDL levels.

Hepatic steatosis refers to the accumulation of lipids in the liver, or "fatty liver", which is frequently caused by alcohol consumption, diabetes and hyperlipidemia and can progress to end-stage liver damage. Given the deleterious consequences of a fatty liver condition, it is of use to identify compounds that prevent or ameliorate hepatic steatosis. Hepatic steatosis may be evaluated both by measurement of tissue triglyceride content and by histologic examination of liver tissue.

Liver tissue triglyceride content was measured using the Triglyceride GPO assay (Roche Diagnostics, Indianapolis, Ind.). Average results for the ISIS 233693 treatment group were normalized to saline-treated control. Treatment with ISIS 233693 caused a 75% reduction in liver triglyceride levels.

Histological analysis was conducted by routine procedures. Briefly, liver samples were procured, fixed in 10% neutral buffered formalin and processed for H&E staining and evaluation of liver morphology. Alternatively, liver tissue was procured, frozen, sectioned, and subsequently stained with oil red O stain to visualize lipid deposits and counterstained with eosin to mark cytoplasm. The prepared samples were evaluated by light microscopy.

As assessed by oil-red O stain and histological analysis, livers from animals treated with ISIS 233693 presented with reduced fat content as compared to saline-treated control livers.

Therefore, oligomeric compounds targeted to angiopoietin-like 3 ameliorate hepatic steatosis as evaluated both by measurement of tissue triglyceride content and by histologic examination of liver tissue.

Taken together, the in vivo studies shown herein indicate that antisense oligonucleotide reduction of angiopoietin-like 3 results in dose dependent reductions in liver target mRNA, as well as reductions in serum and liver triglyceride levels. In addition, antisense oligonucleotides targeted to angiopoietin-like 3 caused decreases in serum cholesterol levels in both lean and high-fat fed mice. Furthermore, reduction in fat pad weight was observed without similar reductions in body or organ weight, indicating target-specific reduction in fat content. Therefore, another aspect of the invention is a method of reducing serum cholesterol, serum triglycerides, liver triglycerides or fat pad weight for conditions such as hyperlipidemia.

Example 9

Effects of Antisense Inhibition of Angiopoietin-like 3 on Atherosclerosis: Treatment with ISIS 233693 in LDLr$^{-/-}$ Mice The effect of ISIS 233693 as an anti-atherosclerotic agent was evaluated in LDL receptor knockout mice fed on a hypercholesterolemic diet; a model used for studying atherosclerosis (Ishibashi et al, *J Clin. Invest.* 1994 May; 93:1885-93).

Treatment

C57Bl/6 mice with LDL receptor gene knockout (Jackson Labs, #2207) were fed a Harlan Tekland diet, TD 94059 (37% kCal fat, half from cocoa butter, 1.25% cholesterol). Four weeks after the initiation of the diet, the mice were divided into two groups consisting of 6-8 mice each for treatment. The first group received twice-weekly subcutaneous injections of ISIS 233693 (SEQ ID No: 131) at doses of 25 mg/kg, for 16 weeks. The second group received twice-weekly subcutaneous injections of mismatched control oligonucleotide, ISIS 141923 (CCTTCCCTGAAGGTTCCTCC, incorporated herein as SEQ ID NO: 187) at doses of 25 mg/kg, for 16 weeks.

Oligonucleotides were dissolved in saline for injection. A group of high-fat fed animals received injections of saline twice weekly for 16 weeks. This saline-injected group served as the control group to which the oligonucleotide-treated groups were compared.

Blood samples were taken every 4 weeks. At the end of the treatment period, the mice were euthanized and liver and aorta were collected for further analysis.

RNA Analysis

RNA was extracted from liver tissue for real-time PCR analysis of ANGPTL3 using an ANGPTL3 primer probe set (forward sequence CACCTGGGCAGTCACGAAA, designated herein as SEQ ID NO: 188; reverse sequence GGAGGGCCCCAGGGATAT, designated herein as SEQ ID NO: 189; probe sequence CACGCTACATGTGGCTGAGATTCGTGG, designated herein as SEQ ID NO: 190). Results are presented as percent inhibition of murine ANGPTL3, relative to PBS control. As shown in Table 13, treatment with ISIS 233693 resulted in significant reduction of ANGPTL3 mRNA in comparison to the PBS control. Treatment with the control oligonucleotide, ISIS 141923 did not result in significant reduction of ANGPTL3, as expected.

TABLE 13

Inhibition of ANGPTL3 mRNA in LDLr$^{-/-}$ mouse liver relative to the PBS control

|  | % inhibition |
|---|---|
| ISIS 141923 | 13 |
| ISIS 233693 | 90 |

Cholesterol and Lipid Levels

Plasma and liver triglycerides, and cholesterol were extracted by the method of Bligh and Dyer (Bligh, E and Dyer, W, *Can J Biochem Physiol,* 37, 911-917, 1959) and measured with the use of a commercially available triglyceride kit (DCL Triglyceride Reagent; Diagnostic Chemicals Ltd.). The results are presented in Tables 14-17. Table 14 demonstrates that treatment with ISIS 233693 resulted in significant decrease in cholesterol levels by 58% on week 16 compared to the PBS control. The decrease in total cholesterol levels was the result of significant decrease in LDL cholesterol levels by 58% compared to the control, as presented in Table 15. Table 16 shows a decrease in HDL that is likely mouse model dependent, as detailed previously. Similarly, Table 17 demonstrates that treatment with ISIS 233693 decreased triglyceride levels by 75% on week 16 compared to the PBS control.

TABLE 14

Effect on total cholesterol levels (mg/dL) in LDLr$^{-/-}$ mice

|  | Week 0 | Week 4 | Week 8 | Week 12 | Week 16 |
|---|---|---|---|---|---|
| PBS | 1,313 | 1,618 | 1,398 | 1,083 | 1,629 |
| ISIS 141923 | 1262 | 1710 | 1624 | 1102 | 1167 |
| ISIS 233693 | 1353 | 1070 | 930 | 558 | 683 |

TABLE 15

Effect on LDL cholesterol levels (mg/dL) in LDLr$^{-/-}$ mice

|  | Week 0 | Week 4 | Week 8 | Week 12 | Week 16 |
|---|---|---|---|---|---|
| PBS | 1,031 | 1,120 | 1,001 | 909 | 1,204 |
| ISIS 141923 | 1022 | 1185 | 1116 | 902 | 843 |
| ISIS 233693 | 1075 | 731 | 648 | 453 | 511 |

TABLE 16

Effect on HDL cholesterol levels (mg/dL) in LDLr$^{-/-}$ mice

|  | Week 0 | Week 4 | Week 8 | Week 12 | Week 16 |
|---|---|---|---|---|---|
| PBS | 154 | 166 | 169 | 145 | 300 |
| ISIS 141923 | 139 | 171 | 179 | 171 | 278 |
| ISIS 233693 | 153 | 116 | 103 | 97 | 159 |

TABLE 17

Effect on triglyceride levels (mg/dL) in LDLr$^{-/-}$ mice

|  | Week 0 | Week 4 | Week 8 | Week 12 | Week 16 |
|---|---|---|---|---|---|
| PBS | 230 | 177 | 134 | 140 | 268 |
| ISIS 141923 | 180 | 154 | 164 | 156 | 159 |
| ISIS 233693 | 191 | 68 | 61 | 72 | 67 |

Atherosclerotic Lesion Assessment

Atherosclerotic lesion severity was assessed in the aortae harvested from mice after perfusion with PBS, followed by formalin PBS solution (5% formalin in PBS). The entire mouse aorta was dissected from the proximal ascending aorta to the bifurcation of the iliac artery by using a dissecting microscope. Adventitial fat was removed, and the aorta was opened longitudinally, pinned flat onto black dissecting wax, stained with Sudan IV, and photographed at a fixed magnification. The photographs were digitized, and total aortic areas and lesion areas were calculated by using Adobe Photoshop version 7.0 and NIH Scion Image software (http://rsb.info.nih.gov/nih-image/Default.html). The results, presented in Table 18, are reported as a percentage of the total aortic area that contained lesions. As presented, treatment with ISIS 233693 resulted in a significant decrease in aortic lesions and improvement of the atherosclerotic condition.

TABLE 18

Effect on lesion area (% of total aortic area) in LDLr$^{-/-}$ mice

|  | lesion area (%) |
|---|---|
| PBS | 44 |
| ISIS 141923 | 40 |
| ISIS 233693 | 18 |

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Plasma concentrations of ALT (alanine transaminase) and AST (aspartate transaminase) were measured and the results are presented in Tables 19 and 20 expressed in IU/L. The measurements were conducted every four weeks. Week 0 is at the start of treatment and four weeks after the initiation of the high fat diet.

TABLE 19

Effect on liver ALT (IU/L) of LDLr$^{-/-}$ mice

|  | Week 0 | Week 4 | Week 8 | Week 12 | Week 16 |
|---|---|---|---|---|---|
| PBS | 29 | 35 | 39 | 36 | 36 |
| ISIS 141923 | 30 | 32 | 32 | 33 | 60 |
| ISIS 233693 | 20 | 48 | 70 | 83 | 91 |

TABLE 20

Effect on liver AST (IU/L) of LDLr$^{-/-}$ mice

|  | Week 0 | Week 4 | Week 8 | Week 12 | Week 16 |
|---|---|---|---|---|---|
| PBS | 49 | 63 | 61 | 82 | 73 |
| ISIS 141923 | 57 | 57 | 61 | 60 | 81 |
| ISIS 233693 | 51 | 60 | 90 | 95 | 108 |

Example 10

Effect of Antisense Inhibition of Angiopoietin-like 3 on Human apoB100 Transgenic LDLr$^{-/-}$ Mice The effect of ISIS 233693 as a lipid lowering agent was evaluated in human apoB-100 transgenic LDL receptor knockout mice fed on a hypercholesterolemic diet. The mice used in these studies have been described in a previous publication Sanan et al, Proc. Natl. Acad. Sci. USA. 95: 4544-4549). In brief, this mouse strain is a hybrid cross between the LDLr$^{-/-}$ mouse described originally by Ishibashi et al. (J. Clin. Invest. 92: 883-893), which is a hybrid of the 129sv and C57BL/6 strains, and the human apoB-100 transgenic mouse (Linton et al, J. Clin. Invest. 92: 3029-3037), which is a hybrid of the SJL and C57BL/6B strains. Breeding indicated that the LDLr$^{-/-}$ and apoB overexpression traits were homozygous, and the mice exhibited a massive increase in apoB-100-containing LDL.

Treatment

The mice were fed a Harlan Tekland diet, TD 88137 or 'Western diet' (21% anhydrous milkfat (butterfat), 34% sucrose, and a total of 0.2% cholesterol). One week after the initiation of the diet, the mice were divided into groups consisting of 5 mice each for treatment. The first cohort received twice-weekly subcutaneous injections of ISIS 233693 (SEQ ID No: 131) at doses of 12.5 mg/kg, 25 mg/kg or 50 mg/kg for 4 weeks. The second cohort received twice-weekly subcutaneous injections of control oligonucleotide, ISIS 141923 (SEQ ID NO: 187) at doses of 12.5 mg/kg or 50 mg/kg, for 4 weeks.

Oligonucleotides were dissolved in saline for injection. A group of high-fat fed animals received injections of saline twice weekly for 4 weeks. This saline-injected group served as the control group to which the oligonucleotide-treated groups were compared.

The mice were weighed weekly. At the end of the treatment period, the mice were euthanized and blood samples, liver, kidney, spleen and fat pads were collected for further analysis.

RNA Analysis

RNA was extracted from liver tissue for real-time PCR analysis of ANGPTL3 using an ANGPTL3 primer probe set (forward sequence CACCTGGGCAGTCACGAAA, designated herein as SEQ ID NO: 187; reverse sequence GGAGGGCCCCAGGGATAT, designated herein as SEQ ID NO: 188; probe sequence CACGCTACATGTGGCTGAGATTCGTGG, designated herein as SEQ ID NO: 189) and of ApoCIII mRNA using an ApoCIII primer probe set (Forward: TGCAGGGCTACATGGAACAA, incorporated herein as SEQ ID NO: 12; Reverse: CGGACTCCTGCACGCTACTT, incorporated herein as SEQ ID NO: 13; Probe: CTCCAAGACGGTCCAGGATGCGC, incorporated herein as SEQ ID NO: 14). Results are presented as percent inhibition of murine ANGPTL3 and murine ApoCIII, relative to PBS control. As shown in Table 21, treatment with ISIS 233693 and ISIS 233725 resulted in significant dose-dependent reduction of ANGPTL3 mRNA in comparison to the PBS control. Treatment with ISIS 233693 also resulted in inhibition of ApoCIII mRNA at 50 mg/kg/week.

RNA levels of liver fatty acid binding protein (LFABP) were also measured by real-time PCR. The results are presented in Table 21, and demonstrate that inhibition of ANGPTL3 by ISIS oligonucleotides also influences the transport of fatty acids in the liver, by inhibiting LFABP. Treatment with the control oligonucleotide, ISIS 141923 did not result in significant reduction of ANGPTL3, LFABP or apoCIII, as expected.

TABLE 21

Percent inhibition of ANGPTL3 and LFABP mRNA in mouse liver relative to the PBS control

| ISIS No | Dose (mg/kg) | ANGPTL3 | ApoCIII | LFABP |
|---|---|---|---|---|
| 233693 | 50 | 95 | 39 | 53 |
|  | 25 | 90 | 25 | 12 |
|  | 12.5 | 77 | 8 | 10 |
| 233725 | 50 | 91 | 27 | 80 |
|  | 25 | 79 | 27 | 51 |
|  | 12.5 | 62 | 12 | 11 |

Cholesterol and Lipid Levels

Plasma and liver triglycerides, and cholesterol were extracted by the method of Bligh and Dyer (Bligh, E and Dyer, W, *Can J Biochem Physiol,* 37, 911-917, 1959) and measured with the use of a commercially available triglyceride kit (DCL Triglyceride Reagent; Diagnostic Chemicals Ltd.). The results are presented in Table 22. The study demonstrates that treatment with ISIS 233693 and ISIS 233725 decreased cholesterol levels by 63% and 37% respectively, at 25 mg/kg/week compared to the PBS control. The decrease in total cholesterol levels was mainly the result of significant decreases in LDL cholesterol levels by 63% and 34% respectively, compared to the control, as presented. The slight decrease in HDL may be mouse model dependent as detailed previously as HDL lowering is commonly observed in mice when hypolipidemic agents are tested in mice. The study demonstrates that treatment with ISIS 233693 and ISIS 233725 decreased triglyceride levels by 82% and 70% respectively, at 25 mg/kg/week compared to the PBS control.

Therefore, treatment with ISIS oligonucleotides targeting ANGPTL3 causes significant improvements of plasma lipid profile in this mouse model.

TABLE 22

Effect on plasma lipid levels (mg/dL)

|  | Dose (mg/kg) | Total cholesterol | HDL | LDL | Triglycerides |
|---|---|---|---|---|---|
| PBS |  | 2534 | 430 | 1591 | 1022 |
| ISIS 141923 | 50 | 1730 | 347 | 998 | 945 |
|  | 12.5 | 2489 | 412 | 1512 | 1168 |
| ISIS 233693 | 50 | 982 | 256 | 585 | 243 |
|  | 25 | 944 | 245 | 596 | 184 |
|  | 12.5 | 1480 | 307 | 990 | 281 |
| ISIS 233725 | 50 | 1407 | 325 | 862 | 403 |
|  | 25 | 1587 | 312 | 1052 | 309 |
|  | 12.5 | 2060 | 370 | 1366 | 522 |

Glucose

To evaluate the effect of ISIS oligonucleotides on glucose production, plasma glucose values were determined using a Beckman Glucose Analyzer II (Beckman Coulter) by a glucose oxidase method. The results are presented in Table 23 and demonstrate that treatment with ISIS 233693 and ISIS 233725 resulted in decrease of plasma glucose levels both by 40% at 50 mg/kg/week compared to the PBS control.

TABLE 23

Effect on plasma glucose levels (mg/dL)

| | Dose (mg/kg) | Glucose |
|---|---|---|
| PBS | | 341 |
| ISIS 141923 | 50 | 334 |
| | 12.5 | 315 |
| ISIS 233693 | 50 | 203 |
| | 25 | 261 |
| | 12.5 | 255 |
| ISIS 233725 | 50 | 203 |
| | 25 | 280 |
| | 12.5 | 284 |

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Plasma concentrations of ALT (alanine transaminase) and AST (aspartate transaminase) were measured and the results are presented in Table 24 expressed in IU/L.

As demonstrated by this study, treatment with ISIS 233693 did not cause any significant increase in transaminase levels and therefore, did not result in any adverse effect on liver function. This assay as well as the RNA analysis establishes ISIS 233693 to be a potent and tolerable antisense oligonucleotide targeting ANGPTL3.

TABLE 24

Effect on plasma transaminases (IU/L)

| | Dose (mg/kg) | ALT | AST |
|---|---|---|---|
| PBS | | 57 | 80 |
| ISIS 141923 | 50 | 61 | 88 |
| | 12.5 | 43 | 79 |
| ISIS 233693 | 50 | 138 | 152 |
| | 25 | 43 | 70 |
| | 12.5 | 45 | 87 |
| ISIS 233725 | 50 | 1443 | 736 |
| | 25 | 217 | 194 |
| | 12.5 | 88 | 138 |

Body and Organ Weights

To evaluate the effect of ISIS oligonucleotides on organ weight, organs were harvested and weight taken after termination of the study. The results are presented in Table 25 and demonstrate that treatment with ISIS oligonucleotides has no effect on liver, spleen or kidney weights. Treatment with ISIS 233693 did decrease fat pad weights of the mice by 77% at 50 mg/kg/week compared to the PBS control.

TABLE 25

Effect on organ weights (g)

| | Dose mg/kg/wk | Liver | Kidney | Spleen | Fat |
|---|---|---|---|---|---|
| PBS | | 1.45 | 0.35 | 0.09 | 1.49 |
| ISIS 141923 | 50 | 1.42 | 0.33 | 0.11 | 0.70 |
| | 12.5 | 1.39 | 0.32 | 0.09 | 0.95 |
| ISIS 233693 | 50 | 1.65 | 0.33 | 0.15 | 0.35 |
| | 25 | 1.42 | 0.32 | 0.13 | 0.51 |
| | 12.5 | 1.49 | 0.35 | 0.11 | 0.89 |

Example 11

Effects of Antisense Inhibition of ANGPTL3 Compared to Fenofibrate Inhibition in C57BL/6 Mice ISIS 233693 targeting mouse ANGPTL3 in comparison to fenofibrate was evaluated in naïve C57BL/6 mice. Fenofibrate is a commercially available treatment for hypercholesterolemia and hypertriglyceridemia in subjects and is known to reduce cholesterol, low-density lipoprotein (LDL), very low density lipoprotein (VLDL) and tryglycerides levels, as well as increase high-density lipoprotein (HDL) levels.

A group of five male C57BL/6 mice fed normal chow were injected twice weekly with 50 mg/kg doses of ISIS 233693 (SEQ ID NO: 131) for six weeks. A second group of mice was treated with fenofibrate, administered as a daily gavage of 50 mg/kg/week. A group of animals received injections of PBS twice weekly for 6 weeks. This PBS-injected group served as the control group to which the oligonucleotide-treated groups were compared.

After the 6 week treatment period, the mice were sacrificed and ANGPTL3 mRNA levels were evaluated in liver. The mRNA expression levels were quantitated by real-time PCR, as described in other examples herein. Relative to PBS-treated mice, ISIS 233693 caused an 85% decrease in ANGPTL3 mRNA levels. The data demonstrate that ANGPTL3 antisense oligonucleotide treatment can effectively inhibit target mRNA expression in liver.

Cholesterol and Lipid Levels

Plasma and liver triglycerides and cholesterol were extracted by the method of Bligh and Dyer (Bligh, E and Dyer, W, *Can J Biochem Physiol*, 37, 911-917, 1959) and measured with the use of a commercially available triglyceride kit (DCL Triglyceride Reagent; Diagnostic Chemicals Ltd.). The results are presented in Table 26. The study demonstrates that treatment with ISIS 233693 decreased cholesterol levels by 23% at 50 mg/kg/week compared to the PBS control. The study demonstrates that treatment with ISIS 233693 decreased triglyceride levels by 38% at 50 mg/kg/week compared to the PBS control. Treatment with fenofibrate had no effect on cholesterol or triglyceride levels.

Therefore, treatment with ISIS oligonucleotides targeting ANGPTL3 causes significant improvements of plasma lipid profile in this mouse model.

TABLE 26

Effect on plasma lipid levels (mg/dL)

| | Total cholesterol | HDL | LDL | Triglycerides |
|---|---|---|---|---|
| PBS | 87 | 75 | 17 | 90 |
| ISIS 233693 | 67 | 54 | 16 | 56 |
| Fenofibrate | 96 | 85 | 16 | 94 |

Glucose

To evaluate the effect of ISIS oligonucleotides on glucose production, plasma glucose values were determined using a Beckman Glucose Analyzer II (Beckman Coulter) by a glucose oxidase method. The results are presented in Table 27 and demonstrate that treatment with ISIS 233693 resulted in decrease of plasma glucose levels by 19% at 50 mg/kg/week compared to the PBS control. Treatment with fenofibrate had no effect on glucose levels.

TABLE 27

Effect on plasma glucose levels (mg/dL)

|  | Glucose |
|---|---|
| PBS | 242 |
| ISIS 233693 | 196 |
| Fenofibrate | 228 |

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Plasma concentrations of ALT (alanine transaminase) and AST (aspartate transaminase) were measured and the results are presented in Table 28 expressed in IU/L.

As demonstrated by this study, treatment with either ISIS 2336393 or fenofibrate did not cause any significant increase in transaminase levels and therefore, did not result in any adverse effect on liver function.

TABLE 28

Effect on plasma transaminases (IU/L)

|  | ALT | AST |
|---|---|---|
| PBS | 23 | 83 |
| ISIS 233693 | 38 | 70 |
| Fenofibrate | 34 | 70 |

Effect on Plasma NEFA and 3HB Levels

NEFA and 3-HB levels were assayed in the mice groups and are shown in Table 29. NEFA and 3-HB levels, as indicators of fat oxidation, were not significantly affected by treatment with ISIS oligonucleotides. Treatment with fenofibrate increased fat oxidation, as indicated by increases in the levels of both NEFA and 3HB.

TABLE 29

Effect on NEFA and 3HB levels

|  | NEFA | 3HB |
|---|---|---|
| PBS | 0.90 | 393 |
| ISIS 233693 | 0.98 | 447 |
| Fenofibrate | 1.20 | 641 |

Organ Weights

To evaluate the effect of ISIS oligonucleotides on organ weight, organs were harvested and weight taken after termination of the study. The results are presented in Table 30 and demonstrate that treatment with ISIS 233693 has no effect on liver, spleen or kidney weights. Treatment with ISIS 233693 did decrease white adipose tissue weight of the mice by 45% at 50 mg/kg/week compared to the PBS control.

TABLE 30

Effect on organ weights (g)

|  | Liver | Spleen | Kidney | White adipose tissue |
|---|---|---|---|---|
| PBS | 1.1 | 0.12 | 0.35 | 0.53 |
| ISIS 233693 | 1.3 | 0.1 | 0.35 | 0.29 |
| Fenofibrate | 1.3 | 0.08 | 0.37 | 0.39 |

Example 12

Effects of Antisense Inhibition of ANGPTL3 in Sprague-Dawley Rats

ISIS 360363 (GTGACATATTCTTCACCTCT; SEQ ID NO: 191) and ISIS 360382 (TTTAAGTGACGTTAC-CTCTG; SEQ ID NO: 192), both 5-10-5 MOE gapmers targeting rat mRNA sequence SEQ ID NO: 193 (Genbank Accession No. XM_233218.1) at start positions 333 and 476, respectively, were evaluated in Sprague Dawley rats.

Two groups of Sprague Dawley rats fed normal chow were injected weekly with 50 mg/kg doses of ISIS 360363 or ISIS 360382 for six weeks. A group of animals received injections of PBS twice weekly for 6 weeks. This PBS-injected group served as the control group to which the oligonucleotide-treated groups were compared.

RNA Analysis

RNA was extracted from liver tissue for real-time PCR analysis of ANGPTL3. Results are presented as percent inhibition of rat ANGPTL3, relative to PBS control. As shown in Table 31, treatment with ISIS 360363 and ISIS 360382 resulted in significant reduction of ANGPTL3 mRNA in comparison to the PBS control.

TABLE 31

Inhibition of ANGPTL3 mRNA in Sprague Dawley rat liver relative to the PBS control

| ISIS No | % inhibition |
|---|---|
| 360363 | 70 |
| 360382 | 89 |

Cholesterol and Lipid Levels

Plasma triglycerides and cholesterol were extracted by the method of Bligh and Dyer (Bligh, E and Dyer, W, *Can J Biochem Physiol*, 37, 911-917, 1959) and measured with the use of a commercially available triglyceride kit (DCL Triglyceride Reagent; Diagnostic Chemicals Ltd.). The results are presented in Table 26. The study demonstrates that treatment with ISIS 360363 and 360382 decreased triglyceride levels by 67% and 81% respectively, compared to the PBS control. Therefore, treatment with ISIS oligonucleotides targeting ANGPTL3 causes significant improvements of plasma triglyceride profile in this rat model. Treatment with ISIS oligonucleotides in this model had no effect on total cholesterol or LDL levels.

TABLE 32

Effect on plasma triglyceride levels (mg/dL)

| PBS | 136 |
|---|---|
| ISIS 360363 | 45 |
| ISIS 360382 | 26 |

What is claimed is:

1. A compound comprising a modified antisense oligonucleotide 10 to 30 linked nucleosides in length targeted to angiopoietin-like 3 (ANGPTL3), wherein
the modified antisense oligonucleotide is targeted to a target region consisting of nucleotides 1094 to 1264 of SEQ ID NO: 4.

2. The compound of claim 1, wherein the modified antisense oligonucleotide has a nucleobase sequence comprising at least 8 contiguous nucleobases of a sequence recited in SEQ ID NO: 87 or SEQ ID NO: 90.

3. The compound of claim 1, wherein at least one internucleoside linkage of said modified antisense oligonucleotide is a modified internucleoside linkage.

4. The compound of claim 3, wherein each internucleoside linkage is a phosphorothioate internucleoside linkage.

5. The compound of claim 1, wherein at least one nucleoside of said modified antisense oligonucleotide comprises a modified nucleobase.

6. The compound of claim 5, wherein the modified nucleobase is a 5-methylcytosine.

7. The compound of claim 1, wherein the modified antisense oligonucleotide consists of 20 linked nucleosides.

8. The compound of claim 1, wherein the modified antisense oligonucleotide comprises:
a) a gap segment consisting of linked deoxynucleosides;
b) a 5' wing segment consisting of linked nucleosides;
c) a 3' wing segment consisting of linked nucleosides;
wherein the gap segment is positioned between the 5' wing segment and the 3' wing segment and wherein each nucleoside of each wing segment comprises a modified sugar.

9. The compound of claim 1, which reduces ANGPTL3 expression in an animal and thereby:
a) reduces apoC-III expression levels;
b) reduces triglyceride levels;
c) reduces cholesterol levels;
d) reduces LDL levels;
e) reduces glucose levels;
f) improves insulin sensitivity;
g) ameliorates a metabolic and/or cardiovascular disease; and/or
h) reduces insulin resistance.

10. A kit for decreasing angiopoietin-like 3 (ANGPTL3), wherein the kit comprises:
(a) a compound comprising a modified antisense oligonucleotide 10 to 30 linked nucleosides in length targeted to ANGPTL3, wherein
the modified antisense oligonucleotide is targeted to a target region consisting of nucleotides 1094 to 1264 of SEQ ID NO: 4, and
(b) a label.

11. The kit of claim 10, wherein the kit further comprises a second agent.

12. The kit of claim 11, wherein the second agent is selected from among a glucose lowering agent, a lipid lowering agent and ascorbic acid.

13. The compound of claim 9, wherein the metabolic and/or cardiovascular disease is selected from among obesity, diabetes, atherosclerosis, dyslipidemia, coronary heart disease, non-alcoholic fatty liver disease (NAFLD), hyperfattyacidemia and metabolic syndrome.

14. The compound of claim 1, further comprising a conjugate.

15. The compound of claim 14, wherein the conjugate is a carbohydrate group.

16. The compound of claim 1, wherein:
at least one modified sugar comprises a (4'—CH(CH$_3$)—O-2') bridge, a (4'—CH$_2$—O-2') bridge, or a 4' (CH$_2$)$_n$—O-2' bridge, and
n is 1 or 2.

17. The compound of claim 1, wherein at least one nucleoside of the modified antisense oligonucleotide comprises a modified sugar.

18. The compound of claim 1, wherein:
at least one modified sugar is a bicyclic sugar or comprises a substituent selected from the group consisting of 5'-methyl, 2'-fluoro, 2'-O—(CH$_2$)$_2$OCH$_3$ and 2'-O—CH$_2$—C(=O)—N(R$_m$)(R$_n$), and
each R$_m$ and R$_n$ independently is hydrogen or substituted or unsubstituted C1-C10 alkyl.

19. The compound of claim 18, wherein the at least one modified sugar is a bicyclic sugar.

20. The compound of claim 18, wherein the at least one modified sugar comprises a 5'-methyl substituent.

21. The compound of claim 18, wherein the at least one modified sugar comprises a 2'-fluoro substituent.

22. The compound of claim 18, wherein the at least one modified sugar comprises a 2'-O—(CH$_2$)$_2$OCH$_3$ substituent.

23. The compound of claim 18, wherein the at least one modified sugar comprises a 2'-O—CH$_2$—C(=O)—N(R$_m$)(R$_n$) substituent, and wherein each R$_m$ and R$_n$ independently is hydrogen or substituted or unsubstituted C1-C10 alkyl.

24. The compound of claim 1, which reduces expression of ANGPTL3 by at least 40%.

25. The kit of claim 10, wherein at least one nucleoside of the modified antisense oligonucleotide comprises a modified sugar.

26. The kit of claim 25, wherein:
at least one modified sugar is a bicyclic sugar or comprises a substituent selected from the group consisting of 5'-methyl, 2'-fluoro, 2'-O—(CH$_2$)$_2$OCH$_3$ and 2'-O—CH$_2$—C(=O)—N(R$_m$)(R$_n$), and
each R$_m$ and R$_n$ independently is hydrogen or substituted or unsubstituted C1-C10 alkyl.

27. The kit of claim 10, wherein the compound reduces expression of ANGPTL3 by at least 40%.

28. A compound comprising a modified antisense oligonucleotide consisting of 20 linked nucleosides and having a nucleobase sequence comprising at least 8 contiguous nucleobases targeted to angiopoietin-like 3 (ANGPTL3), wherein:
the modified antisense oligonucleotide is targeted to a target region consisting of nucleotides 1094 to 1264 of SEQ ID NO: 4;
the modified oligonucleotide comprises:
a gap segment consisting of ten linked deoxynucleosides,
a 5' wing segment consisting of five linked nucleosides, and
a 3' wing segment consisting of five linked nucleosides;
the gap segment is positioned between the 5' wing segment and the 3' wing segment;
each nucleoside of each wing segment comprises a 2'-O-methoxyethyl sugar;
each internucleoside linkage is a phosphorothioate linkage; and
each cytosine residue is a 5-methylcytosine.

29. The compound of claim 28, which reduces expression of ANGPTL3 by at least 40%.

* * * * *